(12) United States Patent
Dossetter et al.

(10) Patent No.: US 8,008,279 B2
(45) Date of Patent: Aug. 30, 2011

(54) COMPOUND—827

(75) Inventors: Alexander Graham Dossetter, Macclesfield (GB); Nicola Murdoch Heron, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 167 days.

(21) Appl. No.: 12/145,855

(22) Filed: Jun. 25, 2008

(65) Prior Publication Data

US 2009/0012077 A1    Jan. 8, 2009

Related U.S. Application Data

(60) Provisional application No. 60/946,178, filed on Jun. 26, 2007, provisional application No. 61/042,840, filed on Apr. 7, 2008.

(51) Int. Cl.
- *A01N 57/00* (2006.01)
- *C07D 401/00* (2006.01)
- *C07D 471/00* (2006.01)
- *C07D 491/00* (2006.01)

(52) U.S. Cl. ............ 514/80; 546/18; 546/65; 546/82; 546/83

(58) Field of Classification Search .............. None
See application file for complete search history.

(56) References Cited

FOREIGN PATENT DOCUMENTS

| | | |
|---|---|---|
| WO | WO01/09110 A1 | 2/2001 |
| WO | WO01/49288 A1 | 7/2001 |
| WO | WO01/68645 | 9/2001 |
| WO | WO02/069901 | 9/2002 |
| WO | WO03/048123 A1 | 6/2003 |
| WO | WO2004/054987 | 7/2004 |
| WO | WO2004/056324 A2 | 7/2004 |

OTHER PUBLICATIONS

Shinozuka et al., Bioorg. Med. Chem. Lett., 2006, 14, 6807-6819.*
Neuropathic, http://www.neurology.org/cgi/content/abstract/70/4/263 (2008).*
Odanacatib, http://www.drugs.com/clinical_trials/odanacatib-merck-s-investigational-cathepsin-k-inhibitor-reduced-markers-bone-turnover-women-breast-4424.html (2011).*
Cai, Jiaqiang et al., "Cathepsin K Inhibitors 2000-2004", Expert Opinion Ther. Patents, vol. 15, No. 1, pp. 33-48, (2005).
Leroy et al. "Cathepsin S inhibitors" Expert Opin. Ther. Patents. 2004 (14) 301-311.
Palermo et al. "Cysteine cathepsin proteases as pharmacological targets in cancer" Trends in Pharmacological Sciences. 2007 (29) 22-28.
Vasiljeva et al. "Emerging Roles of Cysteine Cathepsins in Disease and their Potential as Drug Targets" Current Pharmacological Sciences. 2007 (13) 387-403.
USPTO Office Action in U.S. Appl. No. 10/538,452, mailed May 5, 2008, 14 pages.
Fish & Richardson P.C., Amendment in Reply to Office Action of May 5, 2008 in U.S. Appl. No. 10/538,452, filed Jul. 11, 2008, 10 pages.
USPTO Final Office Action in U.S. Appl. No. 10/538,452, mailed Oct. 27, 2008, 7 pages.
Fish & Richardson P.C., Amendment in Reply to Final Office Action of Oct. 27, 2008 in U.S. Appl. No. 10/538,452, filed Apr. 22, 2009, 9 pages.
Fish & Richardson P.C., RCE in Reply to Final Office Action of Oct. 27, 2008 in U.S. Appl. No. 10/538,452, filed Apr. 27, 2009, 1 page.
USPTO Notice of Allowance in U.S. Appl. No. 10/538,452, mailed May 18, 2009, 6 pages.
Fish & Richardson P.C., RCE/IDS in reply to Notice of Allowance of May 18, 2009 in U.S. Appl. No. 10/538,452, filed Jun. 3, 2009, 5 pages.
USPTO Notice of Allowance in U.S. Appl. No. 10/538,452, mailed Jun. 19, 2009, 8 pages.
Fish & Richardson P.C., Response to Notice of Allowance of Jun. 19, 2009 in U.S. Appl. No. 10/538,452, filed Sep. 19, 2009, 3 pages.
Chen et al. "Novel pycnodysostosis mouse model uncovers cathepsin K function as a potential regulator of osteoclast apoptosis and senescence" Human Molecular Genetics. 2007 16(4) 410-423.
Lindeman et al. "Cathepsin K is the Principal Protease in Giant Cell Tumor of Bone" Am J Pathol. 2004 (165) 593-600.
Lipton "New therapeutic agents for the treatment of bone diseases" Expert Opin. Biol. Ther. 2005 5(6) 817-832.
McIntyre et al. "Relacatib" Drugs of the Future. 2006 31(5) 406-411.
Pearse "New Strategies for the Treatment of Metastatic Bone Disease" Clinical Breast Cancer Supplement. 2007 (8) S-35-S45.
Skoumal et al. "Serum cathepsin K levels of patients with longstanding rheumatoid arthritis: correlation with radiological destruction" Arthritis Res Ther. 2005 (7) R65-R70.
Wang et al. "Cathepsin K inhibitor—polymer conjugates: potential drugs for the treatment of osteoporosis and rheumatoid arthritis" International Journal of Pharmaceutics. 2004 (277) 73-79.
Wang et al. "Drug delivery strategies for cathepsin inhibitors in joint diseases" Expert Opin. Drug Deliv. 2005 2(6) 1015-1028.
Yasuda et al. "The role of cathepsins in osteoporosis and arthritis: Rationale for the design of new therapeutics" Advanced Drug Delivery Reviews. 2005 (57) 973-993.

* cited by examiner

*Primary Examiner* — Sun Jae Loewe

(74) *Attorney, Agent, or Firm* — Fish & Richardson P.C.

(57) ABSTRACT

The present invention relates to compounds and compositions for treating diseases associated with cysteine protease activity. The compounds are reversible inhibitors of cysteine proteases, including cathepsins B, K, C, F, H, L, O, S, W and X. Of particular interest are diseases associated with Cathepsin K.

9 Claims, No Drawings

COMPOUND—827

This application claims the benefit under 35 U.S.C. §119 (e) of Application Ser. No. 60/946,178 (US) filed on 26 Jun. 2007 and Application Ser. No. 61/042,840 (US) filed on 7 Apr. 2008. Each of these two prior applications is incorporated herein by reference in its entirety.

The present invention relates to compounds and compositions for treating diseases associated with cysteine protease activity. The compounds are reversible inhibitors of cysteine proteases, including cathepsins B, K, C, F, H, L, O, S, W and X. Of particular interest are diseases associated with Cathepsin K. In addition this invention also discloses processes for the preparation of such inhibitors.

Cathepsin K is a member of the papain superfamily of cysteine proteases, which also encompasses Cathepsins B, C, F, H, L, O, S, W and X. Cathepsin K is a lysosomal collagenase like enzyme, highly expressed in osteoclast cells and plays a key role in turnover and degradation of the bone organic matrix in skeletal growth and development, but also in diseases. In this respect inhibitors of cathepsin K may be useful agents in the treatment of but not limited to, osteoporosis, osteoarthritis, asthma, rheumatoid arthritis, metastatic bone disease, osteolytic bone cancer and bone related neuropathic pain.

The present invention therefore provides a compound of formula (I)

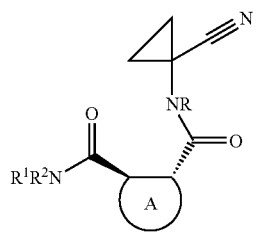

(I)

in which:

A is a 5- to 7-membered aliphatic ring optionally containing a double bond and optionally comprising an oxygen atom as a ring member and optionally being substituted by up to three substituents each independently selected from halogen, $C_{1-2}$alkyl and $C_{3-4}$carbocyclyl;

R is hydrogen or $C_{1-6}$ alkyl $R^1$ and $R^2$ together with the nitrogen atom to which they are attached form a 5- to 7-membered monocyclic saturated or partially unsaturated heterocyclic ring, which ring shares at least one atom with a second monocyclic saturated, partially unsaturated or unsaturated ring so as to form a bicyclic ring system;

which bicyclic ring system shares at least one atom with a third saturated, partially unsaturated or unsaturated ring so as to form a tricyclic ring system comprising up to 19 ring atoms, and wherein the tricyclic ring system optionally comprise up to five heteroatoms each independently selected from O, S or N atoms, and is optionally substituted by up to three substituents each independently selected from phenyl, benzyl, naphthyl, $C_{1-6}$ alkyl, $C_{2-6}$alkenyl, $C_{2-6}$alkynyl, cyano, halogen, $COOR^3$, $COR^3$, $NO_2$, $OR^3$, $CONR^4R^5$, $NR^4R^5$, $C_{1-2}$alkanesulfonyl-, monocyclic heteroaryl comprising up to 7 ring atoms, and bicyclic heteroaryl comprising up to 12 carbon atoms, and the tricyclic ring system is optionally substituted on adjacent carbon atoms by a group —O—C($R^8$)$_2$—O—, wherein each $R^8$ is hydrogen or a halogen atom, so as to form a 1,3-dioxolo group, and wherein (i) phenyl, naphthyl, $C_{1-6}$ alkyl, $C_{2-6}$alkenyl, $C_{2-6}$alkynyl and benzyl are optionally further substituted by up to three substituents each independently selected from halogen, $NR^4R^5$, $SO_2R^3$, $CONR^4R^5$, cyano, $OR^3$, $SO_2NR^4R^5$, $NSO_2R^3$, $NR^4COR^5$, and $C_{1-6}$ alkyl itself optionally substituted with up to three substituents independently selected from halogen, cyano, $SO_2R^3$, $NR^4R^5$, $OR^3$, $SO_2NR^4R^5$, $NSO_2R^3$, $NR^4COR^5$ and $CONR^4R^5$, and (ii) monocyclic or bicyclic heteroaryl are optionally further substituted by up to three substituents each independently selected from halogen, $NR^4R^5$, $SO_2NR^4R^5$, $NSO_2R^3$, $NR^4COR^5$, $CONR^4R^5$, $SO_2R^3$, cyano, $OR^3$, and phenyl itself optionally substituted with up to three halogen groups, $SO_2R^3$, or $C_{1-6}$ alkyl itself optionally substituted with up to three substituents independently selected from halogen, cyano, $SO_2R^3$, $SO_2NR^4R^5$, $NSO_2R^3$, $NR^4COR^5$, $NR^4R^5$, $OR^3$, $C_{3-7}$carbocyclyl and $CONR^4R^5$;

$R^3$ is selected from hydrogen, $C_{1-6}$alkyl, $C_{3-7}$carbocyclyl, phenyl, monocyclic heteroaryl, a 4-7 membered monocyclic saturated heterocyclic ring comprising up to three heteroatoms each independently selected from O, S or N atoms, and wherein $C_{1-6}$ alkyl and phenyl and monocyclic heteroaryl can each be optionally substituted by up to three groups independently selected from halogen, cyano, $CONR^4R^5$, $NR^4R^5$, $SO_2NR^4R^5$, $NSO_2R^3$ and $SO_2R^3$;

$R^4$ and $R^5$ are independently hydrogen, $C_{1-6}$ alkyl, $COR^3$, monocyclic heteroaryl comprising up to 7 ring atoms or bicyclic heteroaryl comprising up to 12 ring atoms or together with the nitrogen to which they are attached form a 5- to 7-membered monocyclic saturated heterocyclic ring optionally comprising up to three additional heteroatoms each independently selected from O, S or N atoms and optionally substituted by $C_{1-6}$ alkyl optionally substituted by $NR^6R^7$;

$R^6$ and $R^7$ are independently hydrogen, $C_{1-6}$ alkyl, or together with the nitrogen to which they are attached form a 5- to 7-membered monocyclic saturated heterocyclic ring optionally comprising up to three additional heteroatoms each independently selected from O, S or N atoms;

and pharmaceutically acceptable salts thereof.

In the context of the present specification, unless otherwise indicated, an alkyl, alkenyl or alkynyl group or an alkyl, alkenyl or alkynyl moiety in a substituent group may be linear or branched. However references to individual alkyl groups such as "propyl" are specific for the straight chain version only and references to individual branched-chain alkyl groups such as t-butyl are specific for the branched chain version only. For example, "$C_{1-3}$alkyl" includes methyl, ethyl, propyl and isopropyl and examples of "$C_{1-6}$alkyl" include the examples of "$C_{1-3}$alkyl" and additionally t-butyl, pentyl, 2,3-dimethylpropyl, 3-methylbutyl and hexyl. Examples of "$C_{1-8}$alkyl" include the examples of "$C_{1-6}$alkyl" and additionally heptyl, 2,3-dimethylpentyl, 1-propylbutyl and octyl. An analogous convention applies to other terms, for example "$C_{2-6}$alkenyl" includes vinyl, allyl, 1-propenyl, 2-butenyl, 3-butenyl, 3-methylbut-1-enyl, 1-pentenyl and 4-hexenyl and examples of "$C_{2-6}$alkynyl" includes ethynyl, 1-propynyl, 3-butynyl, 2-pentynyl and 1-methylpent-2-ynyl.

"$C_{3-4}$carbocyclyl" is a saturated, partially saturated or unsaturated, monocyclic ring containing 3 to 4 carbon ring atoms wherein a —CH$_2$— group can optionally be replaced by a —C(O)—. Suitable examples of "C$_{3-4}$carbocyclyl" are cyclopropyl and cyclobutyl.

"C$_{3-7}$carbocyclyl" is a saturated, partially saturated or unsaturated, monocyclic ring containing 3 to 7 carbon ring atoms wherein a —CH$_2$— group can optionally be replaced by a —C(O)—. Suitable examples of "C$_{3-7}$carbocyclyl" are cyclopropyl, cyclopentyl, cyclobutyl, cyclohexyl, cyclohexenyl, 4-oxocyclohex-1-yl and 3-oxocyclohept-5-en-1-yl.

Aryl groups include phenyl and naphthyl.

"Monocyclic heteroaryl" groups include 5- or 6-membered rings containing one or more heteroatoms selected from N, S, O. Examples include pyridinyl, pyrimidinyl, pyrazinyl, pyrrolyl, pyridazinyl, thiazolyl, oxazolyl, pyrazolyl, imidazolyl, furanyl, thiophenyl and triazolyl. Particular examples of monocyclic heteroaryl groups include pyridinyl and especially pyridin-2-yl and pyridin-6-yl.

Examples of "a 5- to 7-membered monocyclic saturated or partially saturated heterocyclic ring" include pyrrolidinyl, piperidinyl, homopiperidinyl, piperazinyl, morpholinyl, homo-morpholinyl, thiomorpholinyl, 1,1-dioxothiomorpholinyl, 1,4-diazepanyl and homopiperazinyl. Particular examples of a 5-, 6- or 7-membered monocyclic saturated heterocyclic ring optionally containing one or more O, S or N atoms include pyrrolidinyl, piperidinyl, piperazinyl, homopiperazinyl, 1,4-diazepanyl and especially pyrrolidin-1-yl, piperidin-1-yl, piperazin-1-yl, homopiperazin-1-yl and 1,4-diazepan-1-yl.

Examples of "a 4-7 membered monocyclic saturated heterocyclic ring" include azetidinyl pyrrolidinyl, piperidinyl, homopiperidinyl, piperazinyl, morpholinyl, homo-morpholinyl, thiomorpholinyl, 1,1-dioxothiomorpholinyl and homopiperazinyl. Particular examples of a 5-, 6- or 7-membered monocyclic saturated heterocyclic ring optionally containing one or more O, S or N atoms include azetidinyl, pyrrolidinyl, piperidinyl, piperazinyl, homopiperazinyl and especially azetidin-1-yl, pyrrolidin-1-yl, piperidin-1-yl, piperazin-1-yl, homopiperazin-1-yl.

Examples of "a tricyclic ring system" include 1,3,4,5-tetrahydro-2H-pyrido[4,3-b]indolyl, 5,7,8,9-tetrahydro-6H-pyrrolo[2,3-b:4,5-c']dipyridinyl, 1,3,4,5-tetrahydro-2H-pyrrolo[2,3-c:4,5-c']dipyridinyl, 1,3,4,5-tetrahydro-2H-pyrrolo[3,2-c:4,5-c']-dipyridinyl, 5,6,7,9-tetrahydro-8H-pyrido[3',4':4,5]pyrrolo[2,3-b]pyrazinyl, 5,6,7,9-tetrahydro-8H-pyrrolo[3,2-b:4,5-c']dipyridinyl, 5,7,8,9-tetrahydro-6H-pyrido[3',4':4,5]pyrrolo[2,3-c]pyridazinyl, 1,2,3,4-tetrahydro[1]benzofuro[3,2-c]pyridinyl, 6,7,8,9-tetrahydrofuro[3,2-b:4,5-c']dipyridinyl, 5,6,7,8-tetrahydrofuro[2,3-b:4,5-c']dipyridinyl, 5,6,7,8-tetrahydrothieno[2,3-b:4,5-c']dipyridinyl, 1,2,3,4-tetrahydro[1]benzothieno[3,2-c]pyridinyl, 6,7,8,9-tetrahydrothieno[3,2-b:4,5-c']dipyridinyl, 5,6,7,8-tetrahydro-4H-[1,3]thiazolo[4',5':4,5]pyrrolo[3,2-c]pyridinyl, 5,6,7,8-tetrahydro-4H-[1,3]thiazolo[5',4':4,5]pyrrolo[3,2-c]pyridinyl, 5,6,7,8-tetrahydro-4H-thieno[2',3':4,5]pyrrolo[3,2-c]pyridinyl, 5,6,7,8-tetrahydro-4H-thieno[3',2':4,5]pyrrolo[3,2-c]pyridinyl, 5,6,7,8-tetrahydro-4H-furo[2',3':4,5]pyrrolo[3,2-c]pyridinyl, 5,6,7,8-tetrahydro-4H-furo[3',2':4,5]pyrrolo[3,2-c]pyridinyl, 5,6,7,8-tetrahydro-4H-[1,3]oxazolo[4',5':4,5]pyrrolo[3,2-c]pyridinyl, 5,6,7,8-tetrahydro-4H-[1,3]oxazolo[5',4':4,5]pyrrolo[3,2-c]pyridinyl, 1,4,5,6,7,8-hexahydroimidazo[4',5':4,5]pyrrolo[3,2-c]pyridinyl, 3,4,5,6,7,8-hexahydroimidazo[4',5':4,5]pyrrolo[3,2-c]pyridinyl, 2,3,4,5-tetrahydro-1H-pyrido[4,3-b]-7-azaindolyl, 2,3-dihydro-1H-spiro[isoquinoline-4,4'-piperidinyl], benzofuro[3,2-c]-1,2,3,4-tetrahydropyridyl. Particular examples of a tricyclic ring system optionally containing one or more O, S or N atoms include 1,3,4,5-tetrahydro-2H-pyrido[4,3-b]indolyl, 5,7,8,9-tetrahydro-6H-pyrrolo[2,3-b:4,5-c']dipyridinyl, 2,3,4,5-tetrahydro-1H-pyrido[4,3-b]-7azaindolyl, 2,3-dihydro-1H-spiro[isoquinoline-4,4'-piperidinyl], benzofuro[3,2-c]-1,2,3,4-tetrahydropyridyl and especially 1,3,4,5-tetrahydro-2H-pyrido[4,3-b]indol-2-yl and 5,7,8,9-tetrahydro-6H-pyrrolo[2,3-b:4,5-c']dipyridin-6-yl, 2,3,4,5-tetrahydro-1H-pyrido[4,3-b]-7azaindol-2-yl, 2,3-dihydro-1H-spiro[isoquinoline-4,4'-piperidin-2-yl], benzofuro[3,2-c]-1,2,3,4-tetrahydropyrid-2-yl.

The term "halo" refers to fluoro, chloro, bromo and iodo.

Where optional substituents are chosen from "up to three" groups it is to be understood that this definition includes all substituents being chosen from one of the specified groups or the substituents being chosen from two or more of the specified groups. An analogous convention applies to substituents chosen from "1 or 2" groups.

Certain compounds of formula (I) are capable of existing in stereoisomeric forms. It will be understood that the invention encompasses all geometric and optical isomers of the compounds of formula (I) and mixtures thereof including racemates.

It is to be understood that certain compounds of Formula I defined above may exhibit the phenomenon of tautomerism. In particular, tautomerism may affect any heterocyclic groups that bear 1 or 2 oxo substituents. It is to be understood that the present invention includes in its definition any such tautomeric form, or a mixture thereof, which possesses the above-mentioned activity and is not to be limited merely to any one tautomeric form utilised within the formulae drawings or named in the Examples.

It is also to be understood that certain compounds of formula (I) and salts thereof can exist in solvated as well as unsolvated forms such as, for example, hydrated forms. It is to be understood that the invention encompasses all such solvated forms.

A suitable pharmaceutically-acceptable salt of a compound of the Formula (I) is, for example, an acid-addition salt of a compound of the Formula (I), for example an acid-addition salt with an inorganic or organic acid such as hydrochloric, hydrobromic, sulphuric, trifluoroacetic, citric, para-toluenesulphonic, methanesulphonic, tartaric or maleic acid; or, for example, a salt of a compound of the Formula (I) which is sufficiently acidic, for example an alkali or alkaline earth metal salt such as a calcium or magnesium salt, or an ammonium salt. A further suitable pharmaceutically acceptable salt of a compound of the Formula (I) is, for example, a salt formed within the human or animal body after administration of a compound of the Formula (I).

The compounds of the invention may be administered in the form of a pro-drug that is a compound that is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the Formula (I) and in vivo cleavable amide derivatives that may be formed at a carboxy group or an amino group in a compound of the Formula (I).

Accordingly, the present invention includes those compounds of the Formula (I) as defined hereinbefore when made available by organic synthesis and when made available within the human or animal body by way of cleavage of a pro-drug thereof. Accordingly, the present invention includes those compounds of the Formula (I) that are produced by organic synthetic means and also such compounds that are produced in the human or animal body by way of metabolism of a precursor compound, that is a compound of the Formula (I) may be a synthetically-produced compound or a metabolically-produced compound.

A suitable pharmaceutically-acceptable pro-drug of a compound of the Formula (I) is one that is based on reasonable medical judgement as being suitable for administration to the human or animal body without undesirable pharmacological activities and without undue toxicity.

Various forms of pro-drug have been described, for example in the following documents:—
a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically-acceptable pro-drug of a compound of the Formula (I) that possesses a carboxy group is, for example, an in vivo cleavable ester thereof. An in vivo cleavable ester of a compound of the Formula (I) containing a carboxy group is, for example, a pharmaceutically-acceptable ester, which is cleaved in the human or animal body to produce the parent acid. Suitable pharmaceutically-acceptable esters for carboxy include (1-6C)alkyl esters such as methyl, ethyl and tert-butyl, (1-6C)alkoxymethyl esters such as methoxymethyl esters, (1-6C)alkanoyloxymethyl esters such as pivaloyloxymethyl esters, 3-phthalidyl esters, (3-8C) cycloalkylcarbonyloxy-(1-6C)alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and (1-6C)alkoxycarbonyloxy-(1-6C)alkyl esters such as methoxycarbonyloxymethyl and 1-methoxycarbonyloxyethyl esters.

A suitable pharmaceutically-acceptable pro-drug of a compound of the Formula (I) that possesses a hydroxy group is, for example, an in vivo cleavable ester or ether thereof. An in vivo cleavable ester or ether of a compound of the Formula (I) containing a hydroxy group is, for example, a pharmaceutically-acceptable ester or ether, which is cleaved in the human or animal body to produce the parent hydroxy compound. Suitable pharmaceutically-acceptable ester forming groups for a hydroxy group include inorganic esters such as phosphate esters (including phosphoramidic cyclic esters). Further suitable pharmaceutically-acceptable ester forming groups for a hydroxy group include (1-10C)alkanoyl groups such as acetyl, benzoyl, phenylacetyl and substituted benzoyl and phenylacetyl groups, (1-10C)alkoxycarbonyl groups such as ethoxycarbonyl, N,N-[di-(1-4C)alkyl]carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(1-4C)alkylpiperazin-1-ylmethyl. Suitable pharmaceutically-acceptable ether forming groups for a hydroxy group include α-acyloxyalkyl groups such as acetoxymethyl and pivaloyloxymethyl groups.

A suitable pharmaceutically-acceptable pro-drug of a compound of the Formula (I) that possesses an amino group is, for example, an in vivo cleavable amide derivative thereof. Suitable pharmaceutically-acceptable amides from an amino group include, for example an amide formed with (1-10C) alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(1-4C)alkylpiperazin-1-ylmethyl.

The in vivo effects of a compound of the Formula (I) may be exerted in part by one or more metabolites that are formed within the human or animal body after administration of a compound of the Formula (I). As stated hereinbefore, the in vivo effects of a compound of the Formula (I) may also be exerted by way of metabolism of a precursor compound (a pro-drug).

Particular novel compounds of the invention include, for example, compounds of the Formula (I), or pharmaceutically-acceptable salts thereof, wherein, unless otherwise stated, each of A, R, $R^1$ and $R^2$ has any of the meanings defined hereinbefore or hereinafter:—

Conveniently A is a 5-7-membered aliphatic ring optionally containing a double bond and optionally comprising an oxygen atom as a ring member and optionally being substituted by 1, 2 or 3 substituents independently selected from halogen and $C_{3-4}$carbocyclyl. A double bond can be present in any suitable position of the ring A. An oxygen atom can be present in any suitable position of the ring A, in addition to a double bond if desired.

Conveniently, A is a 5-7-membered aliphatic ring optionally being substituted by 1, 2 or 3 substituents independently selected from halogen and $C_{3-4}$-carbocyclyl. More conveniently, A is selected from any one of cyclopentane, norpinane, cycloheptane and cyclohexane. More conveniently, A is cyclohexane.

Conveniently, R is hydrogen or $C_{1-4}$alkyl.
More conveniently, R is hydrogen, methyl, ethyl or propyl.
More conveniently, R is hydrogen.

Conveniently, R¹ and R² together with the nitrogen atom to which they are attached form a 5- to 6-membered monocyclic saturated or partially saturated heterocyclic ring, which ring shares two atoms with a second saturated or unsaturated ring so as to form a bicyclic ring system, which bicyclic ring system shares one or two atoms with a third saturated or unsaturated ring so as to form a tricyclic ring system containing a total of up to 18 atoms, which tricyclic ring system can optionally contain up to three heteroatoms each independently selected from O, S or N atoms and can optionally be substituted by up to three substituents as defined hereinbefore or hereinafter.

Conveniently, the tricyclic ring system formed by R¹ and R² together with the nitrogen atom to which they are attached contains up to 15 atoms.

Conveniently the tricyclic ring system formed by R¹ and R² together with the nitrogen atom to which they are attached can optionally contain up to three heteroatoms each independently selected from O or N atoms and can optionally be substituted by up to three substituents as defined hereinbefore or hereinafter. More conveniently, the tricyclic ring system can optionally be substituted by 1 or 2 substituents as defined hereinbefore or hereinafter.

Conveniently the tricyclic ring system formed by R¹ and R² together with the nitrogen atom to which they are attached can optionally contain up to three heteroatoms each independently selected from O, S or N atoms and can optionally be substituted by up to three substituents independently selected from $C_{1-6}$ alkyl, $C_{2-6}$alkenyl, $C_{2-6}$alkynyl, cyano, halogen, $COOR^3$, $COR^3$, $NO_2$, $OR^3$, $SO_2R^3$, $SR^3$, $CONR^4R^5$, $NR^4R^5$, wherein the $C_{1-6}$ alkyl, $C_{2-6}$alkenyl and $C_{2-6}$alkynyl groups can be optionally substituted further by 1 or 2 substituents independently selected from halogen, $NR^4R^5$, $SO_2R^3CONR^4R^5$, cyano, $OR^3$, $SO_2NR^4R^5$, $NSO_2R^3$, $NR^8COR^9$ or $C_{3-4}$carbocyclyl.

Conveniently, R¹ and R² together with the nitrogen atom to which they are attached form any one of a 1,3,4,5-tetrahydro-2H-pyrido[4,3-b]indolyl, 5,7,8,9-tetrahydro-6H-pyrrolo[2,3-b:4,5-c']dipyridinyl ring, 2,3,4,5-tetrahydro-1H-pyrido[4,3-b]-7azaindolyl, 2,3-dihydro-1H-spiro[isoquinoline-4,4'-piperidinyl], benzofuro[3,2-c]-1,2,3,4-tetrahydropyridyl, 5,6,7,8-tetrahydrofuro[2,3-b:4,5-c']dipyridine, wherein any of the rings can optionally be substituted by 1, 2 or 3 substituent groups as defined hereinbefore or hereinafter.

Conveniently, R³ is hydrogen, $C_{3-7}$carbocyclyl or $C_{1-6}$ alkyl optionally substituted with $NR^6R^7$.

Conveniently, R⁴ is hydrogen or $C_{1-6}$alkyl optionally substituted with halogen, cyano, $CONR^5R^6$, $NR^6R^7$, $SO_2NR^6R^7$, $NSO_2R^3$ or $SO_2R^3$.

More conveniently, R⁴ is hydrogen or $C_{1-6}$ alkyl optionally substituted with halogen.

Conveniently, R⁵ is hydrogen or $C_{1-6}$alkyl.

Conveniently, R⁶ and R⁷ are independently hydrogen or $C_{1-6}$alkyl.

It is to be understood that convenient compounds of the invention include each exemplified compound, each selected independently and pharmaceutically acceptable salts, in vivo hydrolysable esters thereof.

Each of the following groups of compounds, and any combination of compounds within each group, and pharmaceutically acceptable salts, in vivo hydrolysable esters thereof, represents an independent aspect of the invention:

(1R,2R)-N-(1-cyanocyclopropyl)-2-[(8-fluoro-1,3,4,5-tetrahydro-2H-pyrido[4,3-b]indol-2-yl)carbonyl]cyclohexanecarboxamide (1R,2R)-2-[(8-chloro-1,3,4,5-tetrahydro-2H-pyrido[4,3-b]indol-2-yl)carbonyl]-N-(1-cyanocyclopropyl)cyclohexanecarboxamide (1R,2R)-N-(1-cyanocyclopropyl)-2-[(6-fluoro-1,3,4,5-tetrahydro-2H-pyrido[4,3-b]indol-2-yl)carbonyl]cyclohexanecarboxamide (1R,2R)-N-(1-cyanocyclopropyl)-2-(1,3,4,5-tetrahydro-2H-pyrido[4,3-b]indol-2-ylcarbonyl)cyclohexanecarboxamide (1R,2R)-2-[(8-bromo-1,3,4,5-tetrahydro-2H-pyrido[4,3-b]indol-2-yl)carbonyl]-N-(1-cyanocyclopropyl)cyclohexanecarboxamide (1R,2R)-N-(1-cyanocyclopropyl)-2-[(6-methyl-1,3,4,5-tetrahydro-2H-pyrido[4,3-b]indol-2-yl)carbonyl]cyclohexanecarboxamide (1R,2R)-N-(1-cyanocyclopropyl)-2-{[8-(trifluoromethyl)-1,3,4,5-tetrahydro-2H-pyrido[4,3-b]indol-2-yl]carbonyl}cyclohexanecarboxamide (1R,2R)-N-(1-cyanocyclopropyl)-2-[(8-methoxy-1,3,4,5-tetrahydro-2H-pyrido[4,3-b]indol-2-yl)carbonyl]cyclohexanecarboxamide (1R,2R)-N-(1-cyanocyclopropyl)-2-[(8-isopropyl-1,3,4,5-tetrahydro-2H-pyrido[4,3-b]indol-2-yl)carbonyl]cyclohexanecarboxamide (1R,2R)-N-(1-cyanocyclopropyl)-2-[(9-fluoro-1,3,4,5-tetrahydro-2H-pyrido[4,3-b]indol-2-yl)carbonyl]cyclohexanecarboxamide (1R,2R)-N-(1-cyanocyclopropyl)-2-[(7-fluoro-1,3,4,5-tetrahydro-2H-pyrido[4,3-b]indol-2-yl)carbonyl]cyclohexanecarboxamide (1R,2R)-N-(1-cyanocyclopropyl)-2-[(8-fluoro-5-methyl-1,3,4,5-tetrahydro-2H-pyrido[4,3-b]indol-2-yl)carbonyl]cyclohexanecarboxamide (1R,2R)-2-[(6-bromo-1,3,4,5-tetrahydro-2H-pyrido[4,3-b]indol-2-yl)carbonyl]-N-(1-cyanocyclopropyl)cyclohexanecarboxamide (1R,2R)-N-(1-Cyanocyclopropyl)-2-[1,3,4,5-tetrahydro-1H-pyrido[4,3-β]-7-azaindol-2-yl)carbonyl]cyclohexanecarboxamide (1R,2R)-N-(1-cyanocyclopropyl)-2-({8-[(dimethylamino)methyl]-1,3,4,5-tetrahydro-2H-pyrido[4,3-b]indol-2-yl}carbonyl)cyclohexanecarboxamide (1R,2R)-N-(1-cyanocyclopropyl)-2-{[8-(methylsulfonyl)-1,3,4,5-tetrahydro-2H-pyrido[4,3-b]indol-2-yl]carbonyl}cyclohexanecarboxamide (1R,2R)-N-(1-cyanocyclopropyl)-2-[(6-methoxy-1,3,4,5-tetrahydro-2H-pyrido[4,3-b]indol-2-yl)carbonyl]cyclohexanecarboxamide (1R,2R)-N-(1-cyanocyclopropyl)-2-(1H-spiro[isoquinoline-4,4'-piperidin]-2(3H)-ylcarbonyl)cyclohexanecarboxamide (1R,2R)-2-[(6-chloro-1,3,4,5-tetrahydro-2H-pyrido[4,3-b]indol-2-yl)carbonyl]-N-(1-cyanocyclopropyl)cyclohexanecarboxamide (1R,2R)-N-(1-cyanocyclopropyl)-2-[(6-cyano-1,3,4,5-tetrahydro-2H-pyrido[4,3-b]indol-2-yl)carbonyl]cyclohexanecarboxamide (1R,2R)-N-(1-cyanocyclopropyl)-2-[(9-methyl-5,7,8,9-tetrahydro-6H-pyrrolo[2,3-b:4,5-c']dipyridin-6-yl)carbonyl]cyclohexanecarboxamide (1R,2R)-N-(1-cyanocyclopropyl)-2-{[6-(methylthio)-1,3,4,5-tetrahydro-2H-pyrido[4,3-b]indol-2-yl]carbonyl}cyclohexanecarboxamide (1R,2R)-N-(1-cyanocyclopropyl)-2-[(benzofuro[3,2-c]-1,2,3,4-tetrahydropyridyl)carbonyl]cyclohexanecarboxamide (1R,2R)-N-(1-cyanocyclopropyl)-2-{[6-(trifluoromethoxy)-1,3,4,5-tetrahydro-2H-pyrido[4,3-b]indol-2-yl]carbonyl}cyclohexanecarboxamide (1R,2R)-N-(1-cyanocyclopropyl)-2-[(6-ethoxy-1,3,4,5-tetrahydro-2H-pyrido[4,3-b]indol-2-yl)carbonyl]cyclohexanecarboxamide (1R,2R)-N-(1-cyanocyclopropyl)-2-[(5-methoxycarbonylmethyl-1,3,4,5-tetrahydro-2H-pyrido[4,3-b]indol-2-yl)carbonyl]cyclohexanecarboxamide (1R,2R)-N-(1-cyanocyclopropyl)-2-[(5-hydroxycarbonylmethyl-1,3,4,5-tetrahydro-2H-pyrido[4,3-b]indol-2-yl)carbonyl]cyclohexanecarboxamide (1R,2R)-N-(1-cyanocyclopropyl)-2-[(5-cyclopropylmethyl-1,3,4,5-tetrahydro-2H-pyrido[4,3-b]indol-2-yl)carbonyl]cyclohexanecarboxamide (1R,2R)-N-(1-cyanocyclopropyl)-2-[(5-methoxyethyl-1,3,4,5-tetrahydro-2H-pyrido[4,3-b]indol-2-yl)carbonyl]cyclohexanecarboxamide (1R,2R)-N-(1-cyanocyclopropyl)-2-{[6-(trifluoromethyl)-1,3,4,5-tetrahydro-2H-pyrido[4,3-b]indol-2-yl]carbonyl}cyclohexanecarboxamide.

(1R,2R)-N-(1-cyanocyclopropyl)-2-{[6-(methylsulfonyl)-1,3,4,5-tetrahydro-2H-pyrido[4,3-b]indol-2-yl]carbonyl}cyclohexanecarboxamide (1R,2R)-2-{[6-(benzyloxy)-1,3,4,5-tetrahydro-2H-pyrido[4,3-b]indol-2-yl]carbonyl}-N-(1-cyanocyclopropyl)cyclohexanecarboxamide (1R,2R)-N-(1-cyanocyclopropyl)-2-[(6-hydroxy-1,3,4,5-tetrahydro-2H-pyrido[4,3-b]indol-2-yl)carbonyl]cyclohexanecarboxamide.

(1R,2R)-N-(1-cyanocyclopropyl)-2-[(6-propoxy-1,3,4,5-tetrahydro-2H-pyrido[4,3-b]indol-2-yl)carbonyl]cyclohexanecarboxamide (1R,2R)-N-(1-cyanocyclopropyl)-2-{[6-(cyanomethoxy)-1,3,4,5-tetrahydro-2H-pyrido[4,3-b]indol-2-yl]carbonyl}cyclohexanecarboxamide (1R,2R)-N-(1-cyanocyclopropyl)-2-(6-(2-(dimethylamino)ethoxy)-2,3,4,5-tetrahydro-1H-pyrido[4,3-b]indole-2-carbonyl)cyclohexanecarboxamide (1R,2R)-N-(1-cyanocyclopropyl)-2-(6-(2-morpholinoethoxy)-2,3,4,5-tetrahydro-1H-pyrido[4,3-b]indole-2-carbonyl)cyclohexanecarboxamide (1R,2R)-N-(1-cyanocyclopropyl)-2-(6-(2-(pyrrolidin-1-yl)ethoxy)-2,3,4,5-tetrahydro-1H-pyrido[4,3-b]indole-2-carbonyl)cyclohexanecarboxamide (1R,2R)-N-(1-cyanocyclopropyl)-2-(6-(2-(piperidin-1-yl)ethoxy)-2,3,4,5-tetrahydro-1H-pyrido[4,3-b]indole-2-carbonyl)cyclohexanecarboxamide (1R,2R)-N-(1-cyanocyclopropyl)-2-[(5-methanesulphonyl-1,3,4,5-tetrahydro-2H-pyrido[4,3-b]indol-2-yl)carbonyl]cyclohexanecarboxamide (1R,2R)-2-(7,8-Dihydro-5H-furo[2,3-b:4,5-c']dipyridine-6-carbonyl)-cyclohexanecarboxylic acid (1-cyano-cyclopropyl)-amide (1R,2R)-2-(7-Methanesulfonyl-1,3,4,5-tetrahydro-pyrido[4,3-b]indole-2-carbonyl)-cyclohexanecarboxylic acid (1-cyano-cyclopropyl)-amide (1R,2R)-2-(9-Methanesulfonyl-1,3,4,5-tetrahydro-pyrido[4,3-b]indole-2-carbonyl)-cyclohexanecarboxylic acid (1-cyano-cyclopropyl)-amide (1R,2R)-N-(1-cyanocyclopropyl)-2-(2,2-difluoro-7,8,9,10-tetrahydro-6H-[1,3]dioxolo[4,5-g]pyrido[4,3-b]indole-7-carbonyl)cyclohexanecarboxamide (1R,2R)-N-(1-cyanocyclopropyl)-2-(8-fluoro-6-methoxy-2,3,4,5-tetrahydro-1H-pyrido[4,3-b]indole-2-carbonyl)cyclohexanecarboxamide Compounds of formula (I) can be prepared by any of the following routes:

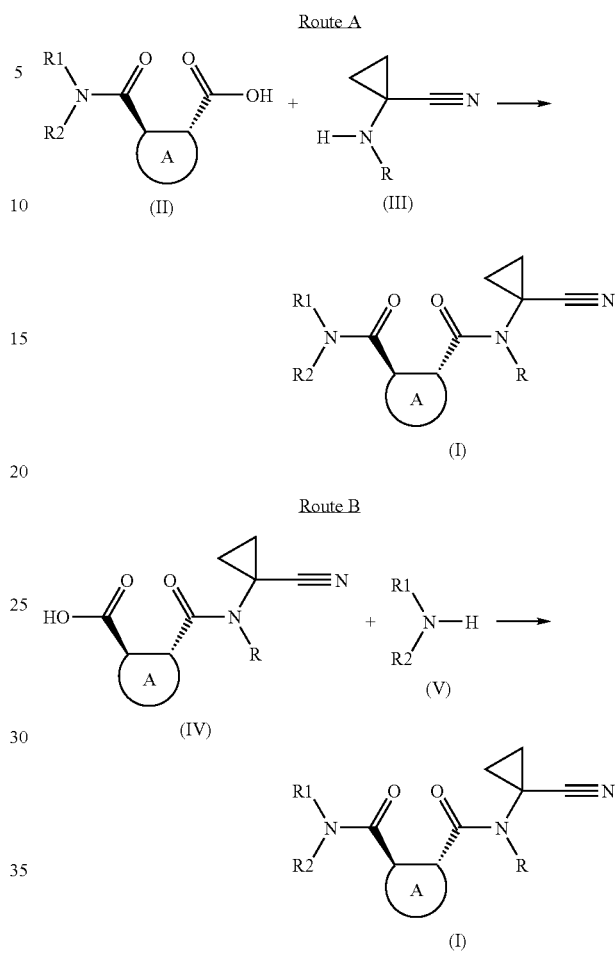

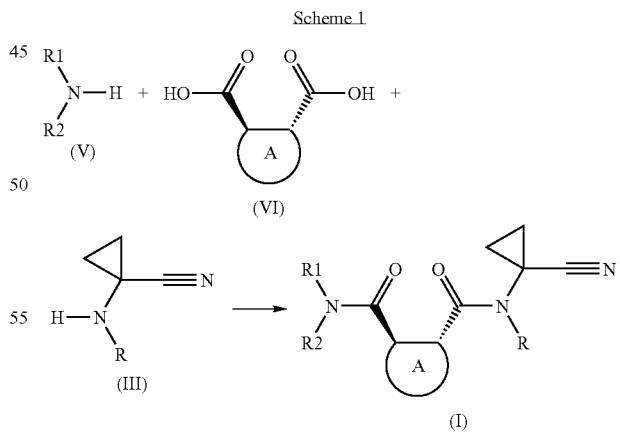

These routes are further illustrated by the following schemes:

Compounds of the type (I) can be synthesised by combining three building blocks as outlined above. A secondary amine of the type represented by generic structure (V) coupled with a single enantiomer of cyclic 1,2-diacid of the type (VI), then an appropriately substituted 1-aminocyclopropylcarbonitrile (III) is coupled to the remaining acid.

Scheme 2

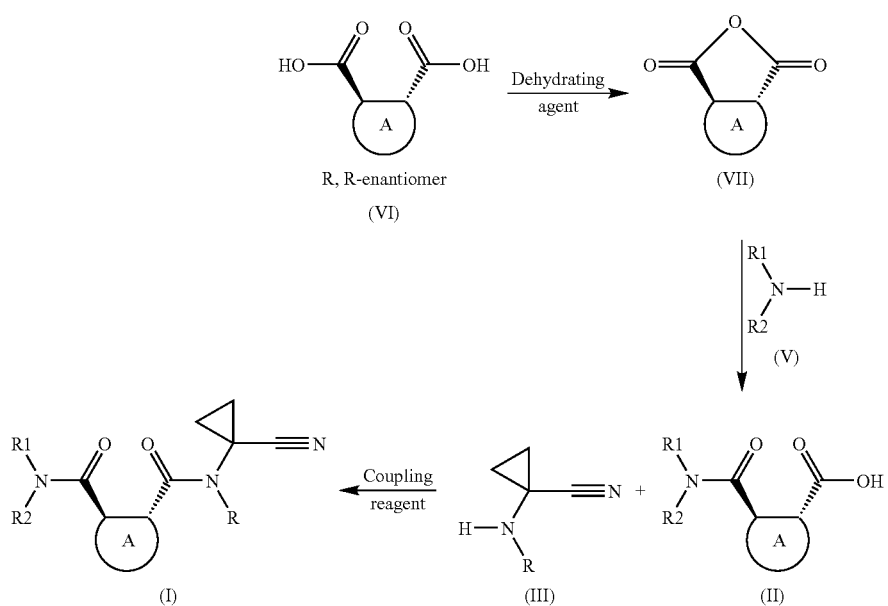

In more detail the chiral cyclic 1,2-diacid (VI) can be dehydrated with a suitable reagent such as acetic anhydride, acetyl chloride, dicyclohexylcarbodiimide (DCC), thionyl-chloride and the such like, preferably acetic anhydride at a temperature between room temperature and 100° C., then removal of excess dehydrating agent yields a bi-cyclic-anhydride of the type (VII). The anhydride (VII) is reactive towards secondary amines of the type (V) in the presence or absence of a suitable base such as triethylamine, diethylisopropylamine, 1,8-diazabicyclo[5.4.0]undec-7-ene (DBU), and the such like or ionic bases such as potassium carbonate, in a suitable aprotic solvent such as dichloromethane (DCM), tetrahydrofuran (THF), diethylether, dimethylformamide (DMF), dimethylacetamide (DMA), tert-butylmethylether (TBME), toluene. The subsequent acid is combined with an appropriately substituted 1-aminocyclopropylcarbonitrile by the use of a coupling agent such as O-(7-azabenzotriazol-1-yl)-N,N,N',N'-tetramethyluronium hexafluorophosphate (HATU), dicyclohexylcarbodiimide (DCC)/hydroxylbenzotriazole (HOBt), 1-benzotriazolyoxy-tris-dimethylamino-phosphonium hexafluorophosphate (BOP), benzotriazoly-oxy-tris-pyrrolidino-phosphonium hexafluorophosphate (PyBOP), N,N-dimethylaminoethylcyclohexylcarbodiimide (EDC), 4-(4,6-dimethoxy-1,3,5-triazin-2-yl)-4-methylmorpholinium chloride (DMTMM), trichloroacetyl chloride, by the formation of an active ester in the presence of a suitable bases triethylamine, diethylisopropylamine, DBU, and the such like or ionic bases such as potassium carbonate, in the presence or absence of an activating base such as N,N-dimethyl-4-amino-pyridine (DMAP) in a suitable solvent dichloromethane (DCM), tetrahydrofuran (THF), diethylether, dimethylformamide (DMF), dimethylacetamide (DMA), tert-butylmethylether (TBME), toluene at a temperature between 0° C. and 60° C. to yield compounds of type (1). A combination of HATU or PyBOP in either DMF or DCM at a temperature between room temperature and 35° C. is preferred.

The chiral cyclic 1,2-diacid of the type (VI) can be produced by methods as shown in the literature— WO2004000825, Eur. J. Org. Chem. 2002, 2948-2952, which include chiral resolution, chiral separation by chromatographic methods, de-symmetrisation using esterase enzymes, such as pig liver esterase as generalised below.

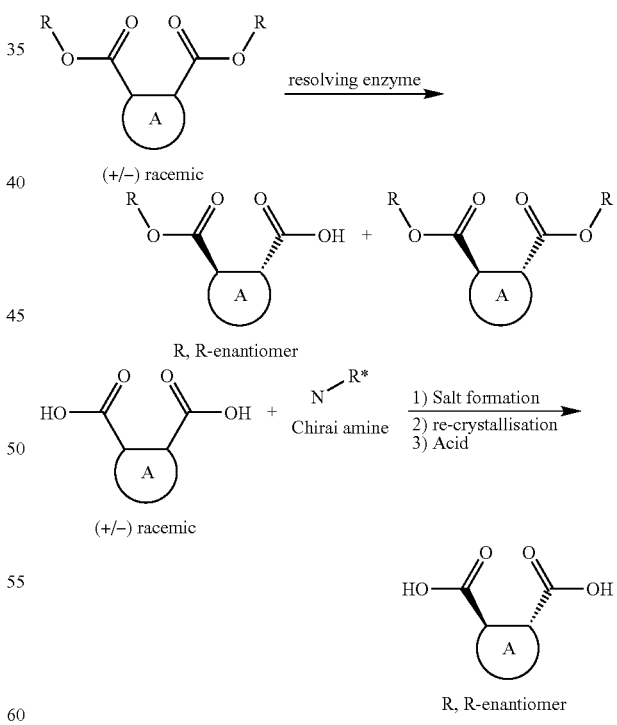

The preferred R,R-cyclohexyl-1,2-dicarboxylic acid can be produced by a resolution of commercially available racemic diacid by a resolution process using chiral amines bases to form diastereomeric salts and recrystallisation of the single enantiomers, as outlined by Eur. J. Org. Chem. 2002, 2948-2952.

Scheme 3

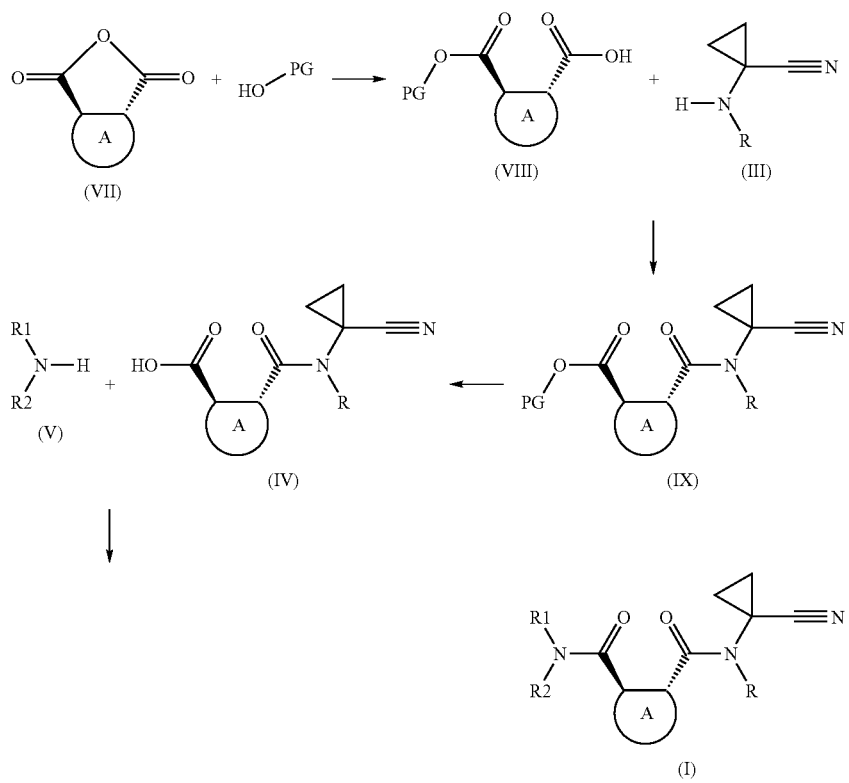

An alternative synthesis of compounds of the type (I) can be made by the route outlined in scheme 3 above. The previously described chiral 1,2-diacid can be reacted with a suitable alcohol such as benzyl alcohol, substituted benzyl alcohol (for example 4-methoxybenzyl alcohol), ethanol, methanol, propan-1-ol, isopropanol, butan-1-ol, at room temperature to 50° C. in a suitable unreactive solvent such as THF, DCM, DMF and the such like to yield an ester-acid of the type (VIII). The reaction with benzyl and substituted benzyl alcohols is preferred. The ester group is now represented by the group PG, as this is formally a protecting group masking the acid. Descriptions of suitable protecting groups in organic synthesis can be found in Green and Wuts *Protective groups in Organic synthesis*, 1991, John Wiley. In a similar manner to that described above a free acid of the type (VIII) can be coupled with an appropriately substituted 1-aminocyclopropylcarbonitrile (III) by the use of a coupling agent such as HATU, PyBOP, EDC, DCC/HOBt, BOP, PyBOP, EDC, DMTMM, trichloroacetyl chloride, by the formation of an active ester in the presence of a suitable bases triethylamine, diethylisopropylamine, DBU and the such like, or suitable ionic bases such as potassium carbonate, in an appropriate solvent dichloromethane (DCM), tetrahydrofuran (THF), diethylether, dimethylformamide (DMF), dimethylacetamide (DMA), tert-butylmethylether (TBME), toluene at a temperature between 0° C. and 100° C. to yield compounds of the type (IX) alternative method would be by conversion to an acid chloride with a suitable reagent such as oxalylchloride, thionyl chloride, and the such like, then addition of the secondary amine (V) in the presence of a bases as list above. A combination of HATU or PyBOP in either DMF or DCM between room temperature and 50° C. is preferred. The protecting group can be removed from compounds of the type (IX) to reveal an acid of the type (IV) by the methods described in Green and Wuts, *Protective groups in Organic synthesis*, 1991, John Wiley. In the preferred case of benzyl group (PG=CH$_2$-phenyl) this can be removed by treatment with hydrogen gas and a suitable catalyst such as palladium on carbon (5 to 10% loading), palladium hydroxide, and the such like or by transferred hydrogenation using such systems as palladium (II) acetate and ammonium formate in a suitable solvent such as methanol, ethanol, ethylacetate and the such like, and heating between 0° C. and 100° C. The appropriate secondary amine (V) (HNR1R2) can then be coupled with acids of type (IV) by the use of a coupling agent such as HATU, PyBOP, EDC, DCC/HOBt, BOP, PyBOP, EDC, DMTMM, by the formation of an active ester in the presence of a suitable bases triethylamine, diethylisopropylamine, DBU and the such like, or suitable ionic bases such as potassium carbonate, in an appropriate solvent dichloromethane (DCM), tetrahydrofuran (THF), diethylether, dimethylformamide (DMF), dimethylacetamide (DMA), tert-butylmethylether (TBME), toluene at a temperature between 0° C. and 100° C. to yield compounds of the type (I). A combination of HATU or PyBOP in either DMF or DCM between room temperature and 50° C. is preferred.

Many of the secondary amines (HNR1R2) used in the synthesis of examples below are from commercially available sources or from routes described previously in the literature. In general terms the compounds can be made by the routes described below.

Scheme 4

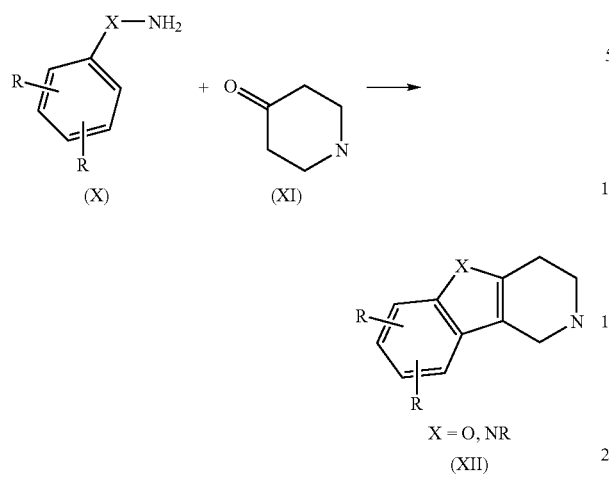

X = O, NR (XII)

In general tricyclic compounds of the type (XII) can be synthesised by a Fischer indole or equivalent [3,3] sigmatropic rearrangement reaction with piperidone (XI) (scheme 4). A suitably substituted aromatic compound (X) is condensed with piperidone to form and intermediate hydrozone by mixing in a suitable inert solvent such as dichloromethane, methanol, ethanol and the such like, in the presence or absence of an acid, such as hydrochloric acid, sulphuric or TFA. The intermediate hydrozone can be isolated and characterised or taken directly on to the cyclisation step, by either heating in an appropriate high boiling point solvent such as toluene, nBuOH, or xylene, acetic acid, and possibly with microwave technology. The reaction can also be driven by the presence of a strong acid such as poly phosphoric acid, hydrochloric acid, sulphuric acid, or by a Lewis acid such as zinc chloride, boron trifluoride etherate and the such like, usually in combination with heating between 50° C. and 200° C. depending on the solvent. In this manner tricyclic compounds can be isolated directly.

Scheme 5

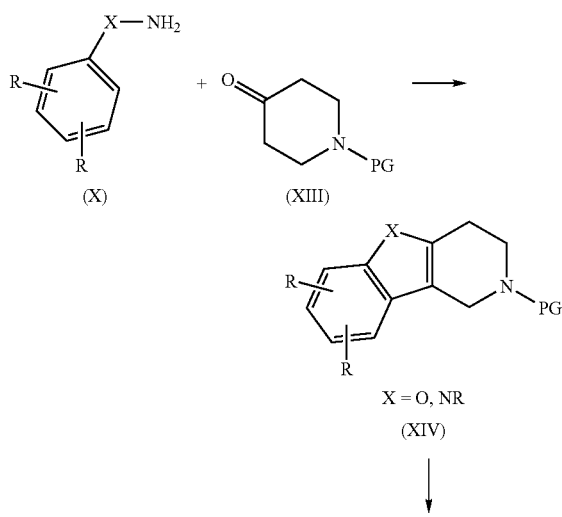

X = O, NR (XIV)

↓

-continued

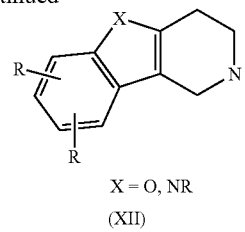

X = O, NR (XII)

In certain cases the piperidone nitrogen atom requires protection for the cyclisation reaction to occur. Appropriate protecting groups, methods of attachment, and removal can be found in Greene and Wut Green and Wuts *Protective groups in Organic synthesis,* 1991, John Wiley. For example benzyl carbamate, tert-butyl carbamate, trifluoroacetyl and benzyl, which are represented above in scheme 5 as the group PG. The synthesis would use the conditions described above for the cyclisation to give compounds of the type (XIV) and then subsequently removal of the protecting group to give the require secondary amine (XII).

According to a further feature of the invention there is provided a compound of the formula (I), or a pharmaceutically acceptable salt thereof, for use as a therapeutic agent.

According to a further feature of the invention there is provided a compound of the formula (I), or a pharmaceutically acceptable salt thereof, for use as a therapeutic agent, where it is desirable to have inhibition of Cathepsin K.

According to a further feature of the present invention there is provided a method for producing inhibition of a cysteine protease in a warm blooded animal, such as man, in need of such treatment, which comprises administering to said animal an effective amount of a compound of the present invention, or a pharmaceutically acceptable salt thereof.

The invention also provides a compound of the formula (I), or a pharmaceutically acceptable salt thereof, for use as a medicament; and the use of a compound of the formula (I) of the present invention, or a pharmaceutically acceptable salt thereof, in the manufacture of a medicament for use in the inhibition of a cysteine protease in a warm blooded animal, such as man. In particular the compounds of the invention are useful in the treatment of inflammation and immune disorders such as, but not limited to, osteoporosis, rheumatoid arthritis, osteoarthritis, metastatic bone disease, osteolytic bone disease and bone related neuropathic pain.

In particular the invention provides the use of a compound of the formula (I) of the present invention, or a pharmaceutically acceptable salt thereof, in the manufacture of a medicament for use in the inhibition of Cathepsin K in a warm blooded animal, such as man. In order to use a compound of the formula (I) or a pharmaceutically acceptable salt thereof for the therapeutic treatment of mammals including humans, in particular in the inhibition of a cysteine protease, it is normally formulated in accordance with standard pharmaceutical practice as a pharmaceutical composition.

Therefore in another aspect the present invention provides a pharmaceutical composition, which comprises a compound of the formula (I) or a pharmaceutically acceptable salt thereof and a pharmaceutically acceptable diluent or carrier.

The pharmaceutical compositions of this invention may be administered in standard manner for the disease condition that it is desired to treat, for example by oral, rectal or parenteral administration. For these purposes the compounds of this invention may be formulated by means known in the art into the form of, for example, tablets, capsules, aqueous or oily solutions or suspensions, (lipid) emulsions, dispersible powders, suppositories, ointments, creams, drops and sterile injectable aqueous or oily solutions or suspensions.

A suitable pharmaceutical composition of this invention is one suitable for oral administration in unit dosage form, for example a tablet or capsule which contains between 1 mg and 1 g of the compound of this invention.

In another aspect a pharmaceutical composition of the invention is one suitable for intravenous, subcutaneous, intramuscular or intra-articular injection.

Each patient may receive, for example, an intravenous, subcutaneous or intramuscular dose of 0.01 mgkg$^{-1}$ to 100 mgkg$^{-1}$ of the compound, preferably in the range of 0.1 mgkg$^{-1}$ to 20 mgkg$^{-1}$ of this invention, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose, the composition being administered 1 to 4 times per day.

The invention further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for the treatment of one or more of the conditions listed.

In particular, for the treatment of (but not restricted to) osteoporosis, rheumatoid arthritis, osteoarthritis, metastatic bone disease, osteolytic bone disease and bone related neuropathic pain, the compounds of the invention may be combined with agents listed below.

Non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The present invention still further relates to the combination of a compound of the invention, or a pharmaceutically acceptable salt thereof, together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 17, and interleukin antagonists or inhibitors such as anakinra; tumour necrosis factor alpha (TNF-α) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

In addition the invention relates to a combination of a compound of the invention, or a pharmaceutically acceptable salt thereof, with a monoclonal antibody targeting B-Lymphocytes (such as CD20 (rituximab), MRA-aIL16R and T-Lymphocytes, CTLA4-Ig, HuMax Il-15).

The present invention still further relates to the combination of a compound of the invention, or a pharmaceutically acceptable salt thereof, with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and CX$_3$CR1 for the C—X$_3$—C family.

The present invention further relates to the combination of a compound of the invention, or a pharmaceutically acceptable salt thereof, with an inhibitor of matrix metalloprotease (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a compound of the invention, or a pharmaceutically acceptable salt thereof, and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAYx1005.

The present invention further relates to the combination of a compound of the invention, or a pharmaceutically acceptable salt thereof, and a receptor antagonist for leukotrienes (LT) B4, LTC4, LTD4, and LTE4. selected from the group consisting of the phenothiazin-3-1s such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAYx7195.

The present invention still further relates to the combination of a compound of the invention, or a pharmaceutically acceptable salt thereof, and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention, or a pharmaceutically acceptable salt thereof, and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention, or a pharmaceutically acceptable salt thereof, and a proton pump inhibitor (such as omeprazole) or a gastroprotective histamine type 2 receptor antagonist.

The present invention further relates to the combination of a compound of the invention, or a pharmaceutically acceptable salt thereof, and an antagonist of the histamine type 4 receptor.

The present invention still further relates to the combination of a compound of the invention, or a pharmaceutically acceptable salt thereof, and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention, or a pharmaceutically acceptable salt thereof, and an anticholinergic agents including muscarinic receptor (M1, M2, and M3) antagonist such as atropine, hyoscine, glycopyrrrolate, ipratropium bromide, tiotropium bromide, oxitropium bromide, pirenzepine or telenzepine.

The present invention still further relates to the combination of a compound of the invention, or a pharmaceutically acceptable salt thereof, and a beta-adrenoceptor agonist (including beta receptor subtypes 1-4) such as isoprenaline, salbutamol, formoterol, salmeterol, terbutaline, orciprenaline, bitolterol mesylate, or pirbuterol, or a chiral enantiomer thereof.

The present invention further relates to the combination of a compound of the invention, or a pharmaceutically acceptable salt thereof, and a chromone, such as sodium cromoglycate or nedocromil sodium.

The present invention still further relates to the combination of a compound of the invention, or a pharmaceutically acceptable salt thereof, with a glucocorticoid, such as flunisolide, triamcinolone acetonide, beclomethasone dipropionate, budesonide, fluticasone propionate, ciclesonide or mometasone furoate.

The present invention further relates to the combination of a compound of the invention, or a pharmaceutically acceptable salt thereof, with an agent that modulates a nuclear hormone receptor such as PPARs.

The present invention still further relates to the combination of a compound of the invention, or a pharmaceutically acceptable salt thereof, together with an immunoglobulin (Ig) or Ig preparation or an antagonist or antibody modulating Ig function such as anti-IgE (for example omalizumab).

The present invention further relates to the combination of a compound of the invention, or a pharmaceutically acceptable salt thereof, and another systemic or topically-applied anti-inflammatory agent, such as thalidomide or a derivative thereof, a retinoid, dithranol or calcipotriol.

The present invention still further relates to the combination of a compound of the invention, or a pharmaceutically acceptable salt thereof, and combinations of aminosalicylates and sulfapyridine such as sulfasalazine, mesalazine, balsalazide, and olsalazine; and immunomodulatory agents such as the thiopurines, and corticosteroids such as budesonide.

The present invention further relates to the combination of a compound of the invention, or a pharmaceutically acceptable salt thereof, together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention, or a pharmaceutically acceptable salt thereof, and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a compound of the invention, or a pharmaceutically acceptable salt thereof, and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention, or a pharmaceutically acceptable salt thereof, and an agent for the treatment of acute or chronic pain, such as a centrally or peripherally-acting analgesic (for example an opioid or derivative thereof), carbamazepine, phenyloin, sodium valproate, amitryptiline or other anti-depressant agent-s, paracetamol, or a non-steroidal anti-inflammatory agent.

The present invention further relates to the combination of a compound of the invention, or a pharmaceutically acceptable salt thereof, together with a parenterally or topically-applied (including inhaled) local anaesthetic agent such as lignocaine or a derivative thereof.

A compound of the present invention, or a pharmaceutically acceptable salt thereof, can also be used in combination with an anti-osteoporosis agent including a hormonal agent such as raloxifene, or a biphosphonate such as alendronate.

The present invention still further relates to the combination of a compound of the invention, or a pharmaceutically acceptable salt thereof, together with a: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Gefitinib or Imatinib mesylate), a to serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-B.sub1.- or B.sub2.-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin NK.sub1. or NK.sub3. receptor antagonist such as NKP-608C, SB-233412 (talnetant) or D-4418; (xx) elastase inhibitor such as UT-77 or ZD-0892; (xxi) TNF-alpha converting enzyme inhibitor (TACE); (xxii) induced nitric oxide synthase (iNOS) inhibitor; (xxiii) chemoattractant receptor-homologous molecule expressed on TH2 cells, (such as a CRTH2 antagonist); (xxiv) inhibitor of P38; (xxv) agent modulating the function of Toll-like receptors (TLR), (xxvi) agent modulating the activity of purinergic receptors such as P2×7; or (xxvii) inhibitor of transcription factor activation such as NFkB, API, or STATS.

A compound of the invention, or a pharmaceutically acceptable salt thereof, can also be used in combination with an existing therapeutic agent for the treatment of cancer, for example suitable agents include:

(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);

(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;

(iii) an agent which inhibits cancer cell invasion (for example a metalloproteinase inhibitor like marimastat or an inhibitor of urokinase plasminogen activator receptor function);

(iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3- chloro-4-fluorophenyl)-7-methoxy-6-(3-morpholinopropoxy)quinazolin-4-amine (gefitinib, AZD 1839), N-(3- ethynylphenyl)-6,7-bis (2-methoxyethoxy)quinazolin-4-amine (erlotinib, OSI-774) or 6-acrylamido-N-(3-chloro-4-fluorophenyl)-7-(3- morpholinopropoxy)quinazolin-4-amine (Cl 1033)), an inhibitor of the platelet-derived growth factor family, or an inhibitor of the hepatocyte growth factor family;

(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin);

(vi) a vascular damaging agent such as combretastatin A4, or a compound disclosed in WO 99/02166, WO 00/40529, WO 00/41669, WO 01/92224, WO 02/04434 or WO 02/08213;

(vii) an agent used in antisense therapy, for example one directed to one of the targets listed above, such as ISIS 2503, an anti-ras antisense;

(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

The invention will now be illustrated by the following Examples, in which standard techniques known to the skilled chemist and techniques analogous to those described by these Examples were used as appropriate:

1 H NMR spectra were recorded using a Bruker DPX300 FT spectrometer or via Flow NMR process using an AVANCE 500 FT spectrometer, and using d6-dimethylsulphoxide (d6-DMSO) or deuterated chloroform ($CDCl_3$) with the data expressed as chemical shifts in ppm from internal standard TMS on the δ scale and with multiplicity (b=broad, s=singlet, d=doublets, t=triplet, q=quartet, qn=quintet, sx=sextet, h=heptet), and integration.

Low resolution mass spectra were obtained using a Waters liquid chromatography mass spectrometry system, where purity was determined by UV absorption at a wavelength of 254 nm, and the mass ion was determined by electrospray ionisation (Micromass instrument). The reverse phase column used was a 4.6 mm×50 mm Phenomenex Synergi Max-RP 80 Å and the solvent system was water containing 0.1% formic acid and acetonitrile unless otherwise stated. A typical run was 5.5 minutes with a 4.0 minute gradient from 0-95% acetonitrile.

Microwave reactions were performed in a Smith Synthesiser (300 Kwatts) on either the normal or high setting using appropriate tubes recommended by the manufacturer.

Purification by column chromatography was typically performed using silica gel (Merck 7734 grade) and solvent mixtures and gradients are recorded herein. Purification by reverse phase high performance chromatography was typically performed using a Perkin Elmer instrument using UV detection at 254 nm and a C18 1500×21.2 mm Phenomenex column 100 Å. Acidic conditions (0.1 to 0.5% formic acid) or basic conditions (ammonia to pH 10) were used with gradiant solvent mixtures of acetonitrile and water.

Scx columns were supplied from International Sorbent Technology and used as directed in this specification.

High purity and dry solvents were supplied from Aldrich and used as delivered.

The following abbreviations are used herein:

| | |
|---|---|
| BOP | 1-benzotriazolyoxy-tris-dimethylamino-phosphonium hexafluorophosphate |
| PyBOP | benzotriazolyoxy-tris-pyrrolidino-phosphonium hexafluorophosphate |
| EDC | N,N-dimethylaminoethylcyclohexylcarbodiimide] |
| DMTMM | 4-(4,6-dimethoxy-1,3,5-t5riazin-2-yl)-4-methylmorpholinium chloride |
| HATU | O-(7-azabenzotriazol-1-yl)-N,N,N',N'-tetramethyluronium hexafluorophosphate |
| NMP | 1-methyl-2-pyrrolidinone |
| DMAP | N,N-dimethyl-4-amino-pyridine |
| DIPEA | di-iso-propylethylamine |
| HPLC | high performance liquid chromatography |
| TBAF | tetra-butylammonium fluoride |
| LCMS | liquid Chromatraphy/Mass Spectrometry |

| | |
|---|---|
| DMF | di-methylformamide |
| TFA | trifluoroacetic acid |
| NaHMDS | sodium hexamethyldisilylamide |
| DMA | dimethylacetamide |
| DEAD | diethylazodicarboxylate |
| mCPBA | meta-chloroperbenzioc acid |
| DMSO | dimethylsulphoxide |
| DBU | 1,8-diazabicyclo[5.4.0]undec-7-ene |
| DCM | dichloromethane |
| Reagent 10 | 1.0M Hydrochloric acid in methanol |

EXAMPLE 1

(1R,2R)-N-(1-cyanocyclopropyl)-2-[(8-fluoro-1,3,4,5-tetrahydro-2H-pyrido[4,3-b]indol-2-yl)carbonyl]cyclohexanecarboxamide

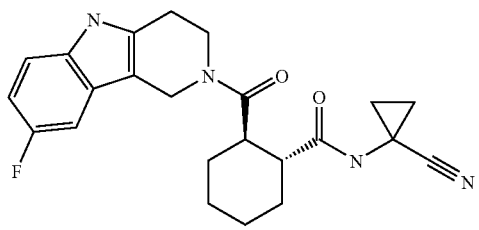

(1R,2R)-Cyclohexane-1,2-dicarboxylic acid (150 mg, 0.87 mmol) was suspended in acetic anhydride (2 mL) and stirred at 80° C. for 1 hour. The mixture was cooled, concentrated in vacuo, azeotroped once with toluene and dried under vacuum to give (3aR,7aR)-hexahydro-2-benzofuran-1,3-dione as a white solid. It was taken up in DMF (5 mL), 8-fluoro-2,3,4,5-tetrahydropyrido[4,3-B]indole (166 mg, 0.87 mmol) was added and the solution stirred at room temperature for 3 hours. 1-Aminocyclopropanecarbonitrile hydrochloride (114 mg, 0.96 mmol) was added followed by triethylamine (0.36 mL, 2.61 mmol) and benzotriazol-1-yloxytripyrrolidinophosphonium hexafluorophosphate (PyBOP, 499 mg, 0.96 mmol) and the mixture stirred overnight. DMF was removed in vacuo and the residue partitioned between DCM (2×30 mL) and 50% brine (10 mL). The combined organics were treated with saturated aqueous sodium bicarbonate (10 mL) and brine (10 mL), dried (magnesium sulphate), concentrated in vacuo and adsorbed onto silica for purification by flash chromatography (0-80% ethyl acetate/isohexane). To purify further, the sample was triturated twice with anhydrous diethyl ether (2×5 mL), filtered and dried under vacuum. This gave (1R,2R)-N-(1-cyanocyclopropyl)-2-[(8-fluoro-1,3,4,5-tetrahydro-2H-pyrido[4,3-b]indol-2-yl)carbonyl]cyclohexanecarboxamide as a white solid (24.0 mg, 7%).

MS (+ve ESI): 408.9 (M+H)$^+$ $^1$H NMR (400 MHz, DMSO) δ 0.8-1.1 (m, 2H), 1.3 (m, 6H), 1.75 (m, 4H), 2.4 (m, 1H), 2.7-3.0 (m, 3H), 3.8 (m, 2H), 4.5-4.7 (m, 2H), 9.9 (m, 1H), 7.2 (m, 1H), 7.3 (s, 1H), 8.65 (s, 1H), 11.0 (s, 1H)

EXAMPLE 2

(1R,2R)-2-[(8-chloro-1,3,4,5-tetrahydro-2H-pyrido[4,3-b]indol-2-yl)carbonyl]-N-(1-cyanocyclopropyl)cyclohexanecarboxamide

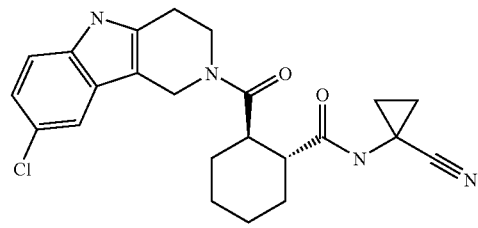

Following example 1, but starting with 8-chloro-2,3,4,5-tetrahydro-1-pyrido[4,3-b]indole (91.0 mg, 0.44 mmol) and purification by silica gel chromatography (elution with 0-100% ethyl acetate/isohexane) furnished the desired compound as a white solid (62.0 mg, 17% yield).

MS (−ve ESI): 426 (M+H)$^+$ $^1$H NMR (400 MHz, DMSO) δ 0.8-1.1 (m, 2H), 1.3 (m, 6H), 1.75 (m, 4H), 2.4 (m, 1H), 2.7-3.0 (m, 3H), 3.8 (m, 2H), 4.5-4.7 (m, 2H), 7.0 (m, 1H), 7.2 (m, 1H), 7.5 (m, 1H), 8.6 (m, 1H), 11.1 (s, 1H)

EXAMPLE 3

(1R,2R)-N-(1-cyanocyclopropyl)-2-[(6-fluoro-1,3,4,5-tetrahydro-2H-pyrido[4,3-b]indol-2-yl)carbonyl]cyclohexanecarboxamide

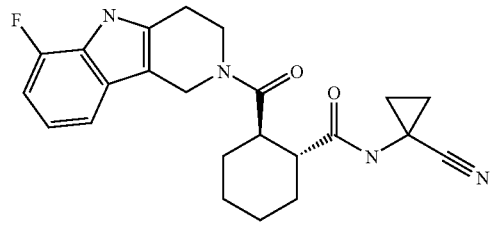

Following Example 1, but starting with 6-fluoro-2,3,4,5-tetrahydro-1H-pyrido[4,3-b]indole (166 mg, 0.87 mmol) furnished the desired compound as a white solid (119 mg, 34% yield).

MS (−ve ESI): 410 (M+H)$^+$ $^1$H NMR (400 MHz, DMSO) δ 0.8-1.1 (m, 2H), 1.3 (m, 6H), 1.75 (m, 4H), 2.4 (m, 1H), 2.7-3.0 (m, 3H), 3.8 (m, 2H), 4.5-4.7 (m, 2H), 6.85 (m, 1H), 7.3 (m, 2H), 8.5 (m, 1H), 11.0 (s, 1H)

EXAMPLE 4

(1R,2R)-N-(1-cyanocyclopropyl)-2-(1,3,4,5-tetrahydro-2H-pyrido[4,3-b]indol-2-ylcarbonyl)cyclohexanecarboxamide

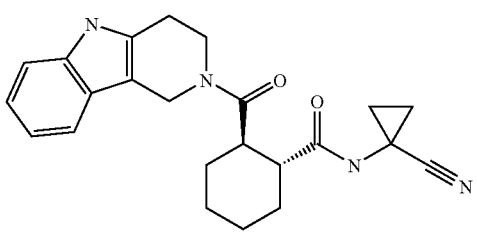

Following Example 1, but starting with 2,3,4,5-tetrahydro-1H-pyrido[4,3-b]indole (149 mg, 0.87 mmol) furnished the desired compound as a white solid (109 mg, 32% yield).

MS (−ve ESI): 392 (M+H)+

$^1$H NMR (400 MHz, DMSO) δ 0.8-1.1 (m, 2H), 1.3 (m, 6H), 1.75 (m, 4H), 2.4 (m, 1H), 2.7-3.0 (m, 3H), 3.8 (m, 2H), 4.5-4.7 (m, 2H), 7.0 (m, 2H), 7.4 (m, 2H), 8.5 (m, 1H), 11.0 (s, 1H)

EXAMPLE 5

(1R,2R)-2-[(8-bromo-1,3,4,5-tetrahydro-2H-pyrido[4,3-b]indol-2-yl)carbonyl]-N-(1-cyanocyclopropyl)cyclohexanecarboxamide

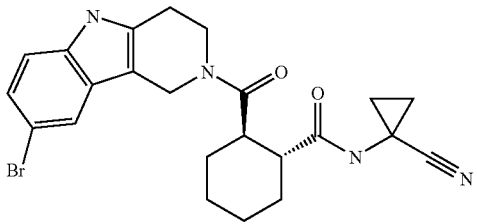

Following Example 1, but starting with 8-bromo-2,3,4,5-tetrahydro-1H-pyrido[4,3-b]indole (106 mg, 0.42 mmol) furnished the desired compound as an off-white solid (23.0 mg, 12% yield).

MS (−ve ESI): 470 (M+H)+

$^1$H NMR (400 MHz, DMSO) δ 0.8-1.1 (m, 2H), 1.3 (m, 6H), 1.75 (m, 4H), 2.4 (m, 1H), 2.7-3.0 (m, 3H), 3.8 (m, 2H), 4.5-4.7 (m, 2H), 7.1 (m, 1H), 7.3 (m, 1H), 7.6 (m, 1H), 8.65 (s, 1H), 11.0 (s, 1H)

EXAMPLE 6

(1R,2R)-N-(1-cyanocyclopropyl)-2-[(6-methyl-1,3,4,5-tetrahydro-2H-pyrido[4,3-b]indol-2-yl)carbonyl]cyclohexanecarboxamide

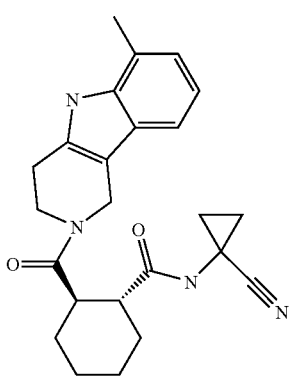

Following Example 1, but starting with 6-chloro-2,3,4,5-tetrahydro-1H-pyrido[4,3-b]indole (206 mg, 1.00 mmol) furnished the desired compound as a white foam (179 mg, 42% yield).

MS (+ve ESI): 425 (M+H)+

$^1$H NMR (400.132 MHz, CDCl$_3$) δ 0.85-1.96 (11H, m), 2.62 (1H, t), 2.87 (2H, m), 3.03 (2H, m), 3.61-4.40 (2H, m), 4.67-4.90 (2H, m), 6.63 (1H, d), 7.04 (1H, m), 7.16 (1H, t), 7.35 (1H, m), 8.16 (1H, m)

EXAMPLE 7

(1R,2R)-N-(1-cyanocyclopropyl)-2-{[8-(trifluoromethyl)-1,3,4,5-tetrahydro-2H-pyrido[4,3-b]indol-2-yl]carbonyl}cyclohexanecarboxamide

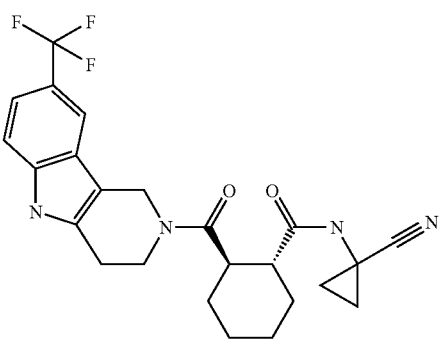

Following Example 1, but starting with 8-(trifluoromethyl)-2,3,4,5-tetrahydro-1H-pyrido[4,3-b]indole (240 mg, 1.00 mmol) furnished the desired compound as a yellow gum (249 mg, 54% yield).

MS (+ve ESI): 459 (M+H)+

$^1$H NMR (400.132 MHz, CDCl$_3$) δ 0.83-1.96 (12H, m), 2.59-3.10 (4H, m), 3.72-4.21 (2H, m), 4.52-5.06 (2H, m), 6.81 (1H, d), 7.33 (1H, m), 7.39 (1H, s), 7.70 (1H, d), 8.45 (1H, d)

8-(trifluoromethyl)-1,3,4,5-tetrahydro-2H-pyrido[4,3-b]indole was prepared in the following manner:—

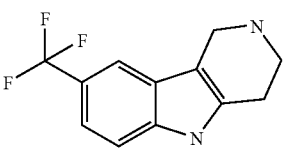

Following the above example but starting with (4-trifluoromethyl)phenylhydrazine hydrochloride (1.36 g, 10 mmol) furnished the desired compound as an off white solid (1.60 mg, 66% yield).

MS (+ve ESI): 240 (M+H)+

$^1$H NMR (400.132 MHz, DMSO) δ 2.75 (2H, t), 3.08 (2H, t), 3.94 (2H, s), 7.34 (1H, d), 7.50 (1H, d), 7.75 (1H, s), 11.30 (1H, s)

EXAMPLE 8

(1R,2R)-N-(1-cyanocyclopropyl)-2-[(8-methoxy-1,3,4,5-tetrahydro-2H-pyrido[4,3-b]indol-2-yl)carbonyl] cyclohexanecarboxamide

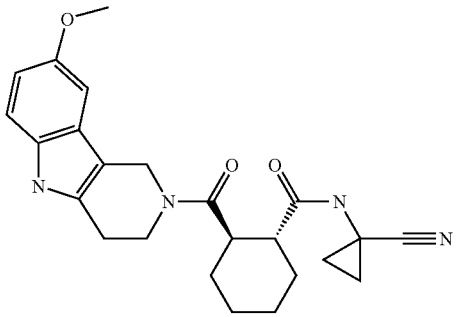

Following Example 1, but starting with 8-methoxy-2,3,4,5-tetrahydro-1H-pyrido[4,3-b]indole (202 mg, 1 mmol) furnished the desired compound as a yellow solid (192 mg, 46% yield).

MS (+ve ESI): 421 (M+H)$^+$ $^1$H NMR (400.132 MHz, CDCl$_3$) δ 0.82-1.91 (13H, m), 2.63 (1H, m), 2.82 (1H, m), 3.00 (1H, m), 3.61 and 4.38 (1H, m), 3.86 (3H, d), 3.86 (1H, m), 4.76 (2H, m), 6.68 (1H, d), 6.81 (1H, m), 6.90 (1H, m), 7.19 (1H, m), 7.82 (1H, d)

EXAMPLES 9 AND 10

(1R,2R)-N-(1-cyanocyclopropyl)-2-[(9-fluoro-1,3,4,5-tetrahydro-2H-pyrido[4,3-b]indol-2-yl)carbonyl] cyclohexanecarboxamide

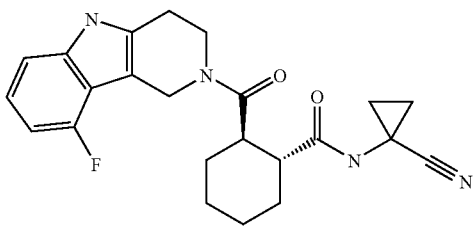

(1R,2R)-N-(1-cyanocyclopropyl)-2-[(7-fluoro-1,3,4,5-tetrahydro-2H-pyrido[4,3-b]indol-2-yl)carbonyl] cyclohexanecarboxamide

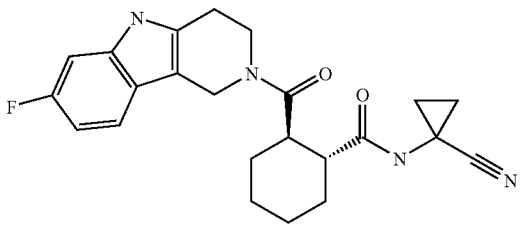

Following Example 1, but starting with a mixture of 1H-pyrido[4,3-b]indole-9-fluoro-2,3,4,5-tetrahydro and 1H-pyrido[4,3-b]indole-7-fluoro-2,3,4,5-tetrahydro (30:70) (390 mg, 2.05 mmol) and heating the Pybop reaction mixture at 60° C. for 18 of hours furnished the desired compound as a mixture of isomers. Purification with column chromatography (0-80% ethyl acetate/isohexane) furnished (1R,2R)-N-(1-cyanocyclopropyl)-2-[(9-fluoro-1,3,4,5-tetrahydro-2H-pyrido[4,3-b]indol-2-yl)carbonyl]cyclohexanecarboxamide as a yellow solid (34.0 mg, 5% yield) and (1R,2R)-N-(1-cyanocyclopropyl)-2-[(7-fluoro-1,3,4,5-tetrahydro-2H-pyrido[4,3-b]indol-2-yl)carbonyl]cyclohexanecarboxamide as a yellow solid (66.0 mg, 8% yield).

(1R,2R)-N-(1-cyanocyclopropyl)-2-[(9-fluoro-1,3,4,5-tetrahydro-2H-pyrido[4,3-b]indol-2-yl)carbonyl] cyclohexanecarboxamide MS (+ve ESI): 409 (M+H)$^+$ $^1$H NMR (400.132 MHz, DMSO) δ 0.8-1.1 (m, 2H), 1.3 (m, 6H), 1.75 (m, 4H), 2.4 (m, 1H), 2.7-3.0 (m, 3H), 3.8 (m, 2H), 4.5-4.7 (m, 2H), 6.7 (m, 1H), 7.0 (m, 1H), 7.1 (s, 1H), 8.7 (s, 1H), 11.2 (s, 1H)

(1R,2R)-N-(1-cyanocyclopropyl)-2-[(7-fluoro-1,3,4,5-tetrahydro-2H-pyrido[4,3-b]indol-2-yl)carbonyl] cyclohexanecarboxamide MS (+ve ESI): 409 (M+H)$^+$ $^1$H NMR (400.132 MHz, DMSO) δ 0.8-1.1 (m, 2H), 1.3 (m, 6H), 1.75 (m, 4H), 2.4 (m, 1H), 2.7-3.0 (m, 3H), 3.8 (m, 2H), 4.5-4.7 (m, 2H), 6.8 (m, 1H), 7.05 (m, 1H), 7.4 (m, 1H), 8.7 (s, 1H), 11.0 (s, 1H)

1H-pyrido[4,3-b]indole-9-fluoro-2,3,4,5-tetrahydro and 1H-pyrido[4,3-b]indole-7-fluoro-2,3,4,5-tetrahydro used as a starting material was prepared as follows:

Piperidin-4-one hydrochloride (3.37 g, 24.8 mmol) was dissolved in ethanol (80 mL). Water (3 drops) was added followed by 3-fluorophenylhydrazine hydrochloride (4.04 g, 24.8 mmol) and the reaction mixture heated at reflux for 1 hour. The mixture was allowed to cool to room temperature and hydrogen chloride gas was bubbled through the solution for approximately 15 minutes. Refluxing was recommenced for 1.5 hours. The suspension was cooled to room temperature overnight, cooled to 0° C. and the resultant filtered and washed with ethanol (c.f. 30 mL). The residue was taken up in water (30 mL), made basic with 2M aqueous sodium hydroxide and the resulting precipitate filtered off and washed with water to afforded the desired compounds as an off white solid consisting of a mixture of isomers (9-fluoro-2,3,4,5-tetrahydropyrido[4,3-B]indole: 7-fluoro-2,3,4,5-tetrahydropyrido[4,3-B]indole (30:70)) (1.76 g, 37% yield). The isomers were inseparable by column chromatography and the mixture was used directly in the next step.

EXAMPLE 11

(1R,2R)-N-(1-cyanocyclopropyl)-2-[(8-isopropyl-1,3,4,5-tetrahydro-2H-pyrido[4,3-b]indol-2-yl)carbonyl]cyclohexanecarboxamide

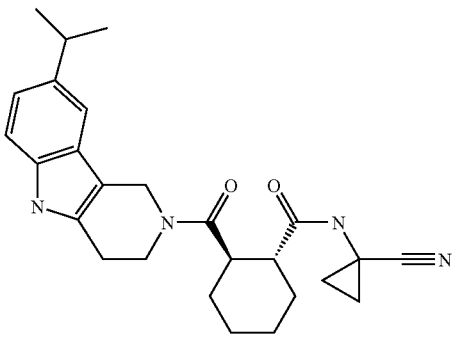

Following Example 1, but starting with 8-isopropyl-2,3,4,5-tetrahydro-1H-pyrido[4,3-b]indole (214 mg, 1 mmol) furnished the desired compound as a yellow solid (180 mg, 42% yield).

MS (+ve ESI): 433 (M+H)$^+$ $^1$H NMR (400.132 MHz, CDCl$_3$) δ 0.83-1.92 (19H, m), 2.58-3.09 (5H, m), 3.59 and 4.40 (1H, m), 3.88 (1H, m), 4.65-4.92 (2H, m), 7.05 (1H, t), 7.23 (1H, t), 7.29 (1H, d), 7.85 (1H, d)

8-isopropyl-2,3,4,5-tetrahydro-1H-pyrido[4,3-b]indole

Following Examples 9 and 10 but starting with 4-isopropylphenylhydrazine hydrochloride (1.86 g, 10 mmol) furnished the desired compound as an off-white solid (1.50 g, 71% yield).

MS (+ve ESI): 215 (M+H)$^+$ $^1$H NMR (400.132 MHz, CDCl$_3$) δ 1.29 (6H, d), 2.74 (2H, t), 2.99 (1H, m), 3.22 (2H, t), 4.07 (2H, s), 7.02 (1H, m), 7.22 (2H, m), 7.69 (1H, s)

EXAMPLE 12

(1R,2R)-N-(1-cyanocyclopropyl)-2-[(8-fluoro-5-methyl-1,3,4,5-tetrahydro-2H-pyrido[4,3-b]indol-2-yl)carbonyl]cyclohexanecarboxamide

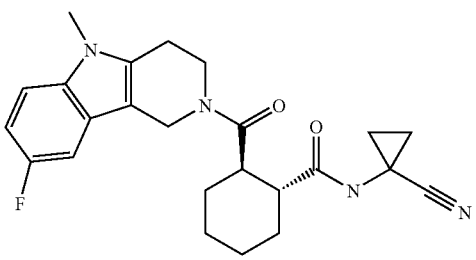

Following Example 1, but starting with 8-fluoro-5-methyl-2,3,4,5-tetrahydro-1H-pyrido[4,3-b]indole (250 mg, 1.04 mmol) and heating the Pybop reaction mixture at 60° C. overnight furnished the desired compound as a yellow solid (76.0 mg, 17% yield).

MS (+ve ESI): 423 (M+H)$^+$ $^1$H NMR (400.132 MHz, DMSO) δ 0.8-1.1 (m, 2H), 1.3 (m, 6H), 1.75 (m, 4H), 2.4 (m, 1H), 2.7-3.0 (m, 3H), 3.65 (d, 3H), 3.9 (m, 2H), 4.5-4.75 (m, 2H), 6.9 (m, 1H), 7.3 (m, 2H), 8.5 (m, 1H)

8-fluoro-5-methyl-2,3,4,5-tetrahydro-1H-pyrido[4,3-b]indole hydrochloride used as a starting material was prepared as follows:

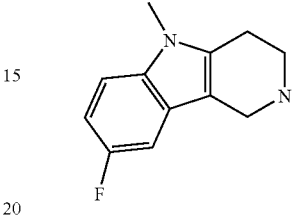

tert-Butyl-8-fluoro-5-methyl-1,3,4,5-tetrahydro-2H-pyrido[4,3-b]indole-2-carboxylate[4] (340 mg, 1.12 mmol) was dissolved in methanol (10 mL). 4N Hydrogen chloride in 1,4-dioxan (1 mL) was added and the solution stirred at room temperature overnight. The reaction mixture was concentrated in vacuo, azeotroped once with toluene and dried under vacuum to furnish the desired compound as a brown solid (260 mg, 97% yield).

[4] Ruediger, Edward H.; Deon, Daniel H.; Kadow, John F. Preparation of tetrahydrocarbolines for treatment of HIV infection and AIDS. U.S. Pat. Appl. Publ. (2005), 12 pp. CODEN: USXXCO US 2005267130 A120051201 CAN 144:22907 AN 2005:1262744 CAPLUS $^1$H NMR (400.132 MHz, DMSO) δ 3.05 (t, 2H), 3.45 (t, 2H), 3.65 (s, 3H), 4.25 (s, 2H), 7.0 (t, 1H), 7.3 (d, 1H), 7.5 (m, 1H), 9.7 (s, 1H)

EXAMPLE 13

(1R,2R)-2-[(6-bromo-1,3,4,5-tetrahydro-2H-pyrido[4,3-b]indol-2-yl)carbonyl]-N-(1-cyanocyclopropyl)cyclohexanecarboxamide

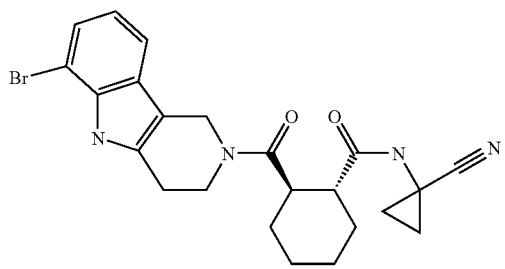

Following Example 1, but starting with 6-bromo-2,3,4,5-tetrahydro-1H-pyrido[4,3-b]indole (251 mg, 1.0 mmol) and heating the Pybop reaction mixture at 60° C. overnight furnished the desired compound as a white foam (306 mg, 65% yield).

MS (+ve ESI): 469 (M+H)$^+$ $^1$H NMR (400.132 MHz, CDCl$_3$) δ 0.83-1.96 (13H, m), 2.62 (1H, t), 2.87 (1H, m), 3.03 (1H, m), 3.61-4.39 (2H, m), 4.77 (2H, m), 6.68 (1H, d), 6.99 (1H, m), 7.31 (1H, t), 7.38 (1H, t), 8.12 (1H, s)

6-bromo-2,3,4,5-tetrahydro-1H-pyrido[4,3-b]indole used as a starting material was prepared as follows:

Following Examples 9 and 10 but starting with (2-bromophenyl)hydrazine (2.24 g, 10 mmol) furnished the desired compound as an off-white solid (716 mg, 29% yield)

MS (+ve ESI): 251 (M+H)⁺

¹H NMR (400.132 MHz, DMSO) δ 2.70 (2H, t), 3.01 (2H, t), 3.84 (2H, s), 6.88 (1H, t), 7.20 (1H, d), 7.33 (1H, d), 10.88 (1H, s)

EXAMPLE 14

(1R,2R)-N-(1-Cyanocyclopropyl)-2-[1,3,4,5-tetrahydro-1H-pyrido[4,3-B]-7-azaindol-2-yl)carbonyl]cyclohexanecarboxamide

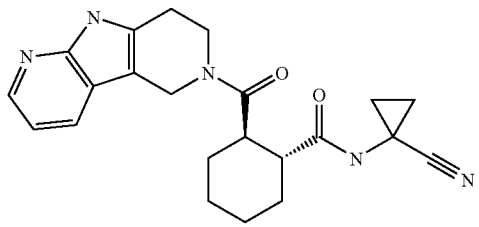

Following Example 1, but starting with 2,3,4,5-tetrahydro-1H-pyrido[4,3-b]-7-azaindole (200 mg, 1.15 mmol) and heating the Pybop reaction mixture at 60° C. overnight furnished the desired compound as an off white solid (40.0 mg, 9% yield).

MS (+ve ESI): 392 (M+H)⁺

¹H NMR (400.132 MHz, DMSO) δ 0.8-1.1 (m, 2H), 1.3 (m, 6H), 1.75 (m, 4H), 2.4 (m, 1H), 2.7-3.0 (m, 3H), 3.8 (m, 2H), 4.5-4.7 (m, 2H), 7.0 (m, 1H), 7.85 (m, 1H), 8.13 (m, 1H), 8.65 (s, 1H), 11.4 (s, 1H)

2,3,4,5-tetrahydro-1H-pyrido[4,3-b]-7azaindole used as a starting material was prepared as follows:

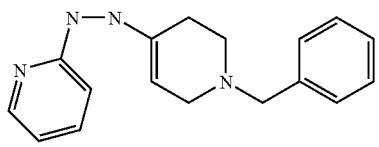

a) 2-Hydrazinopyridine dihydrochloride (5 g, 27.5 mmol) and 1-benzylpiperidin-4-one (6.18 g, 27.5 mmol) were suspended in ethanol (70 mL). Acetic acid (2 mL) was added and the mixture stirred at reflux for 2 hours, cooled to room temperature and concentrated in vacuo. The residue was partitioned between 2N aqueous sodium hydroxide (10 mL) and dichloromethane (2×30 mL) and combined organics were dried (sodium sulphate), concentrated in vacuo and adsorbed onto silica for purification by chromatography eluting with 0-15% methanol/dichloromethane. This gave 1-benzylpiperidin-4-one pyridin-2-ylhydrazone as a pale yellow gum which was used crude in the next reaction (7.70 g, 100% yield).

¹H NMR (400.132 MHz, DMSO) δ 2.3 (t, 2H), 2.4 (t, 2H), 2.6 (m, 2H), 3.5 (m, 2H), 6.7 (m, 1H), 7.05 (d, 1H), 7.35 (m, 5H), 7.55 (t, 1H), 8.05 (d, 1H), 9.4 (s, 1H)

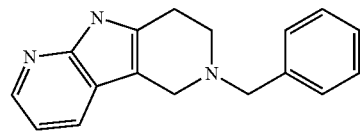

b) Polyphosphoric acid (60 g) was added to 1-benzylpiperidin-4-one pyridin-2-ylhydrazone (7.69 g, 27.5 mmol) and the mixture stirred gently at 150° C. for 24 hours. The mixture was cooled to room temperature and ice (50 g) was added to break up the polyphosphoric acid gum. The reaction mixture was made basic with 2M aqueous sodium hydroxide and extracted with ethyl acetate (3×300 mL). The combined organic extracts were treated with brine (90 mL), dried (sodium sulphate), concentrated in vacuo and adsorbed onto silica for purification by chromatography eluting with 0-10% methanol/dichloromethane. The mustard coloured solid obtained (3.80 g) was shown by NMR not to be pure and was thus triturated with a small volume of dichloromethane, filtered and dried to furnish the desired compound as a sand coloured solid (3.00 g, 42% yield).

¹H NMR (400.132 MHz, DMSO) δ 2.8 (s, 4H), 3.6 (s, 2H), 3.75 (s, 2H), 6.95 (m, 1H), 7.35 (m, 5H), 7.7 (d, 1H), 8.1 (s, 1H), 11.35 (s, 1H)

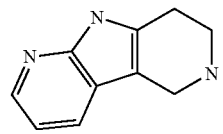

c) 2,3,4,5-Tetrahydro-1-benzyl-pyrido[4,3-B]-7-azaindole (2.90 g, 11.0 mmol), ammonium formate (2.78 g, 44.0 mmol) and 20% palladium hydroxide on carbon (290 mg) were suspended in ethanol (200 mL) and stirred under reflux. After 1 hour, more ammonium formate (695 mg, 1 equivalent) was added and refluxing continued for 1 hour. The catalyst was filtered off through celite, washed with a small volume of dichloromethane and the combined filtrate concentrated in vacuo and dried under vacuum to furnish the desired compound as an off white solid (1.90 g, 100% yield).

¹H NMR (400.132 MHz, DMSO) δ 2.7 (t, 2H), 3.05 (t, 2H), 3.85 (s, 2H), 6.9 (m, 1H), 7.7 (d, 1H), 8.05 (m, 1H), 11.2 (s, 1H)

EXAMPLE 15

(1R,2R)-N-(1-cyanocyclopropyl)-2-({8-[(dimethylamino)methyl]-1,3,4,5-tetrahydro-2H-pyrido[4,3-b]indol-2-yl}carbonyl)cyclohexanecarboxamide

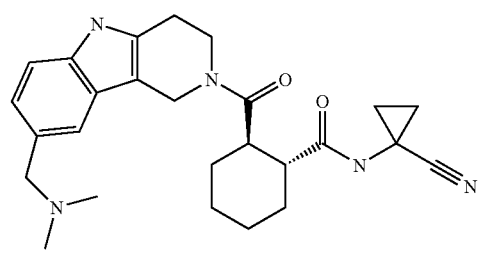

Following Example 1, but starting with N,N-dimethyl-1-(2,3,4,5-tetrahydro-1H-pyrido[4,3-b]indol-8-yl)methanamine (330 mg, 1.44 mmol) and heating the Pybop reaction mixture at 60° C. overnight furnished the desired compound as an off white solid (102 mg, 16% yield).

MS (+ve ESI): 448 (M+H)+

1H NMR (400.132 MHz, DMSO) δ 0.8-1.1 (m, 2H), 1.3 (m, 6H), 1.75 (m, 4H), 2.7 (m, 8H), 3.0 (m, 2H), 3.85 (m, 2H), 4.3 (m, 2H), 4.4-4.9 (m, 2H), 7.1 (m, 1H), 7.35 (m, 1H), 7.6 (m, 1H), 8.65 (m, 1H), 11.1 (s, 1H)

N,N-dimethyl-1-(2,3,4,5-tetrahydro-1H-pyrido[4,3-b]indol-8-yl)methanamine

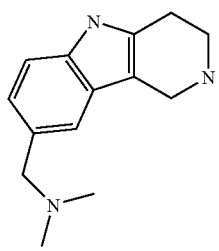

Following Example 13 but starting with dimethylaminomethylphenylhydrazine hydrochloride[5] (3.90 g, 5.36 mmol). The residue was purified by silica gel chromatography. Eluting with 100% dichloromethane then increased polarity to 5% aqueous ammonia in 50% ethanol/dichloromethane furnished the desired compound as a light brown gum (450 mg, 37% yield).

[5] J. Moron, etc, J. Heterocyclic Chemistry, 1992, 29(6), 1573-1576

1H NMR (400.132 MHz, DMSO) δ 2.1 (s, 6H), 2.7 (m, 3H), 3.2 (m, 3H), 3.85 (s, 2H), 6.90 (d, 1H), 7.2 (m, 2H), 10.6 (s, 1H)

EXAMPLE 16

(1R,2R)-N-(1-cyanocyclopropyl)-2-{[8-(methylsulfonyl)-1,3,4,5-tetrahydro-2H-pyrido[4,3-b]indol-2-yl]carbonyl}cyclohexanecarboxamide

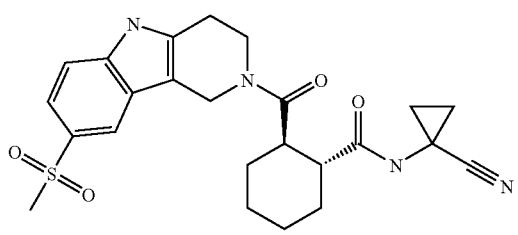

Following Example 1, but starting with 8-(methylsulfonyl)-2,3,4,5-tetrahydro-1H-pyrido[4,3-b]indole (200 mg, 0.80 mmol) and heating the Pybop reaction mixture at 60° C. overnight furnished the desired compound as an off white solid (156 mg, 42% yield).

MS (+ve ESI): 469 (M+H)+

1H NMR (400.132 MHz, DMSO) δ 0.8-1.1 (m, 2H), 1.3 (m, 6H), 1.75 (m, 4H), 2.4 (m, 1H), 2.7-3.0 (m, 3H), 3.15 (m, 3H), 3.85 (m, 2H), 4.4-4.9 (m, 2H), 7.45 (m, 1H), 7.55 (m, 1H), 8.1 (m, 1H), 8.65 (s, 1H), 11.5 (s, 1H)

8-(Methylsulfonyl)-1,3,4,5-tetrahydro-2H-pyrido[4,3-b]indole was prepared in the following manner:—

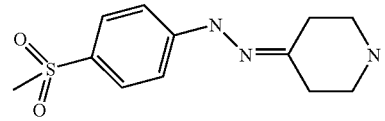

4-(Methylsulphonyl)phenylhydrazine (1.00 g, 5.37 mmol) was suspended in ethanol (30 mL). Water (3 drops) was added followed by 4-piperidone dihydrochloride (925 mg, 5.37 mmol) and acetic acid (1 mL) and the mixture stirred under reflux for 1 hour. It was allowed to cool to room temperature and concentrated in vacuo, azeotroped once with toluene and dried under vacuum. This gave 4-methylsulfonyl-N-(4-piperidylidene amino)aniline hydrochloride as a yellow solid (1.57 g, 96%).

MS (+ve ESI): 268 (M+H)+

1H NMR (400 MHz, DMSO) δ 2.7 (m, 4H), 3.3 (s, 3H), 3.6 (m, 4H), 7.25 (d, 2H), 7.7 (d, 2H).

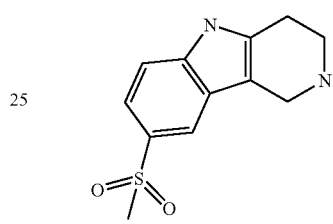

4-Methylsulfonyl-N-(4-piperidylideneamino)aniline hydrochloride (1.56 g, 5.13 mmol) was suspended in acetic acid (30 mL) and stirred at room temperature under argon. Boron trifluoride diethyl etherate (1.26 mL, 10.3 mmol) was added in one portion and the yellow suspension stirred at 90° C. for 2 hours resulting in a deep red solution. It was cooled to room temperature and acetic acid removed in vacuo. The residue was partitioned between 2N aqueous sodium hydroxide (30 mL) and dichloromethane (2×100 mL). Combined organics were dried (sodium sulphate), concentrated in vacuo and adsorbed onto silica for purification by flash silica chromatography (100% DCM to 5% aqueous ammoniin 50% ethanol/DCM). This gave 8-methanesulphonyl-2,3,4,5-tetrahydropyrido[4,3-b]indole as a pale yellow foam (560 mg, 44%).

1H NMR (400 MHz, DMSO) δ 2.7 (m, 2H), 3.05 (m, 2H), 3.15 (s, 3H), 3.9 (s, 2H), 7.5 (m, 2H), 7.95 (s, 1H), 11.4 (s, 1H).

EXAMPLE 17

(1R,2R)-N-(1-cyanocyclopropyl)-2-[(6-methoxy-1,3,4,5-tetrahydro-2H-pyrido[4,3-b]indol-2-yl)carbonyl]cyclohexanecarboxamide

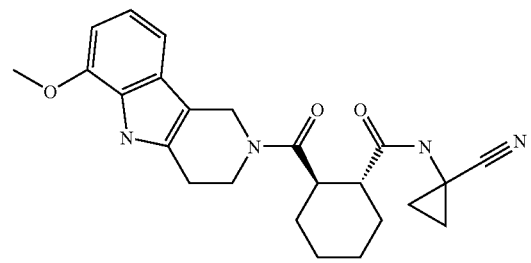

Following Example 1, but starting with 6-methoxy-2,3,4,5-tetrahydro-1H-pyrido[4,3-b]indole (202 mg, 1 mmol) furnished the desired compound as a yellow gum (271 mg, 65% yield).

MS (+ve ESI): 421 (M+H)+

¹H NMR (400.132 MHz, CDCl₃) δ 0.82-1.97 (12H, m), 2.59-3.08 (4H, m), 3.56 (1H, m), 3.86 (1H, m), 3.94 (3H, d), 4.42 (0H, m), 4.65-4.90 (2H, m), 6.64 (1H, t) 6.89 (1H, s), 7.04 (2H, m), 8.17 (1H, d)

6-methoxy-2,3,4,5-tetrahydro-1H-pyrido[4,3-b]indole used as a starting material was prepared as follows:

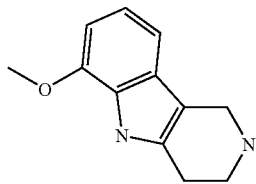

As for Example 13 but starting with 2-methoxyphenylhydrazine hydrochloride (1.38 g, 10 mmol) furnished the desired compound as a brown solid (712 mg, 35% yield) which was used directly in the next step.

¹H NMR (400.132 MHz, DMSO) δ 2.65 (2H, t), 3.01 (2H, t), 3.83 (2H, s), 3.89 (3H, s), 6.59 (1H, d), 6.84 (1H, t), 6.91 (1H, d), 10.71 (1H, s)

EXAMPLE 18

(1R,2R)-N-(1-cyanocyclopropyl)-2-(1H-spiro[isoquinolin-4,4'-piperidin]-2(3H)-ylcarbonyl)cyclohexanecarboxamide

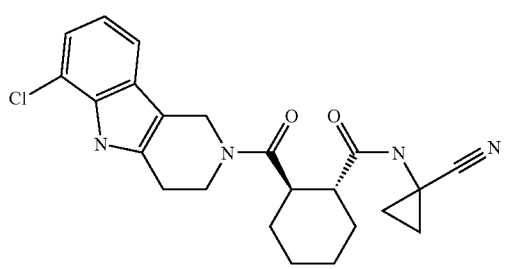

To a solution of tert-butyl 2-[((1R,2R)-2-{[(1-cyanocyclopropyl)amino]carbonyl}cyclohexyl)carbonyl]-2,3-dihydro-1H,1'H-spiro[isoquinoline-4,4'-piperidine]-1'-carboxylate (100 mg, 0.19 mmol) in DCM (20 mL) was added TFA (22 mg, 0.19 mmol) dropwise and the reaction mixture stirred for 4 hours. The reaction mixture was concentrated in-vacuo and the residue purified by basic HPLC (the compound was diluted with Acetonitrile/H₂O; filtered; pH adjusted to >9 with NH₃, injected onto a Waters 100 mm×19 mm XBridge C18 5μ column; flow 16 mLs/min; Solvent A=0.1% NH₃/Water, Solvent B=CH₃CN; λ=230 nm) to furnish the desired compound as a white solid (58.0 mg, 73% yield).

MS (+ve ESI): 421 (M+H)+ hu 1H NMR (400.13 MHz, CDCl₃) δ1.04-1.13 (1H, m), 1.15-1.21 (1H, m), 1.31-1.62 (6H, m), 1.86-1.92 (6H, m), 2.03-2.11 (1H, m), 2.61 (1H, m), 2.88-3.11 (5H, m), 3.48-4.34 (2H, m), 4.75-4.79 (2H, m), 7.06 (1H, s), 7.11 (1H, m), 7.19 (1H, m), 7.26 (1H, d), 7.45 (1H, m)

tert-butyl 2-[((1R,2R)-2-{[(1-cyanocyclopropyl)amino]carbonyl}cyclohexyl)carbonyl]-2,3-dihydro-1H,1'H-spiro[isoquinoline-4,4'-piperidine]-1'-carboxylate

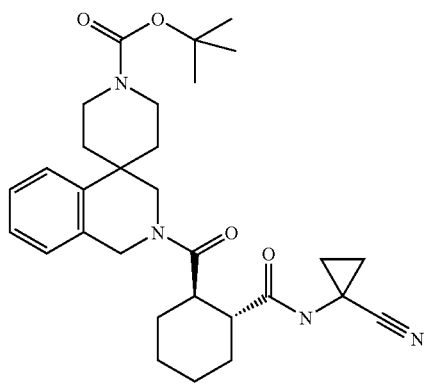

Following Example 1, but starting with tert-butyl 2,3-dihydro-1H,1'H-spiro[isoquinoline-4,4'-piperidine]-1'-carboxylate (655 mg, 1.93 mmol) furnished the desired compound as a colourless oil (285 mg, 30% yield).

MS (−ve ESI): 519 (M−H)+

EXAMPLE 19

(1R,2R)-2-[(6-chloro-1,3,4,5-tetrahydro-2H-pyrido[4,3-b]indol-2-yl)carbonyl]-N-(1-cyanocyclopropyl)cyclohexanecarboxamide Following Example 1 but starting with 6-chloro-2,3,4,5-tetrahydro-1H-pyrido[4,3-b]indole (206 mg, 1.9 mmol) furnished the desired compound as a white foam (179 mg, 42% yield).

MS (+ve ESI): 425 (M+H)+

¹H NMR (400.13 MHz, CDCl₃) δ 0.85-1.96 (11H, m), 2.62 (1H, t), 2.87 (2H, m), 3.03 (2H, m), 3.61-4.40 (2H, m), 4.67-4.90 (2H, m), 6.63 (1H, d), 7.04 (1H, m), 7.16 (1H, t), 7.35 (1H, m), 8.16 (1H, m)

6-chloro-2,3,4,5-tetrahydro-1H-pyrido[4,3-b]indole

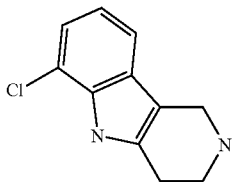

Following Example 13 but starting with (2-chlorophenyl)hydrazine hydrochloride (1.79 g, 10 mmol) furnished the desired compound as an off white solid (592 mg, 29% yield).
MS (+ve ESI): 207 (M+H)$^+$
$^1$H NMR (400.13 MHz, DMSO) δ 2.70 (2H, m), 3.02 (2H, m), 3.85 (2H, m), 6.93 (1H, m), 7.07 (1H, m), 7.23-7.38 (1H, m), 11.00 (1H, s)

EXAMPLE 20

(1R,2R)-N-(1-cyanocyclopropyl)-2-[(6-cyano-1,3,4,5-tetrahydro-2H-pyrido[4,3-b]indol-2-yl)carbonyl]cyclohexanecarboxamide

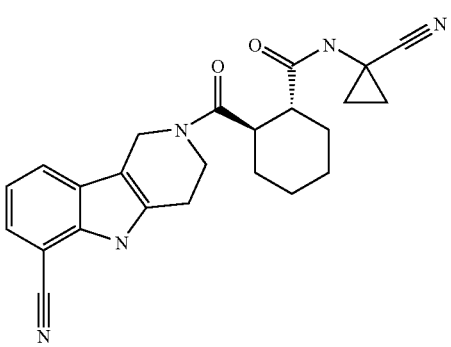

Following Example 1, but starting with 2,3,4,5-tetrahydro-1H-pyrido[4,3-b]indole-6-carbonitrile [WO 2004/056324] (198 mg, 1.00 mmol) furnished the desired compound as a white solid (247 mg, 59% yield).
MS (+ve ESI) 416 (M+H)$^+$
1H NMR (400.132 MHz, DMSO) 0.69-1.04 (m, 2H), 1.11-1.46 (m, 6H), 1.60-1.88 (m, 4H), 2.40-2.48 (m, 1H), 2.55-3.07 (m, 3H), 3.68-3.94 (m, 2H), 4.61 (q, 1H), 4.78 (s, 1H), 7.09-7.19 (m, 1H), 7.53 (t, 1H), 7.85 (q, 1H), 8.71 (d, 1H), 11.86 (s, 1H)

EXAMPLE 21

(1R,2R)-N-(1-cyanocyclopropyl)-2-[(9-methyl-5,7,8,9-tetrahydro-6H-pyrrolo[2,3-b:4,5-c']dipyridin-6-yl)carbonyl]cyclohexanecarboxamide

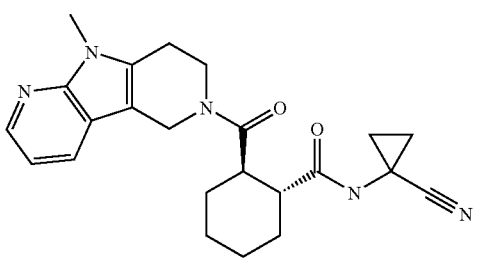

(1R,2R)-N-(1-Cyanocyclopropyl)-2-[1,3,4,5-tetrahydro-1H-pyrido[4,3-B]-7-azaindol-2-yl)carbonyl]cyclohexanecarboxamide (Example 14, 80.0 mg, 0.20 mmol) was dissolved in DMF (5 mL) and stirred at room temperature under argon. Iodomethane (0.012 mL) was added followed by sodium hydride (9.0 mg, 0.20 mmol). After 1 hour, the reaction was quenched with brine (10 mL) and partitioned with ethyl acetate (3×30 mL). Combined organic extracts were dried (sodium sulphate), concentrated in vacuo and adsorbed onto silica for purification by flash chromatography (0-5% methanol/dichloromethane). This gave (1R,2R)-N-(1-cyanocyclopropyl)-2-[1,3,4,5-tetrahydro-1H-pyrido[4,3-B]-7-N-methylazaindol-2-yl)carbonyl]cyclohexanecarboxamide as a white solid (42.0 mg, 52%).
MS (+ve ESI): 406 (M+H)$^+$
1H NMR (400 MHz, DMSO) δ 0.8-1.1 (m, 2H), 1.3 (m, 6H), 1.75 (m, 4H), 2.4 (m, 1H), 2.65-3.2 (m, 3H), 3.65 (m, 3H), 3.9 (m, 2H), 4.5-4.75 (m, 2H), 7.0 (m, 1H), 7.85 (m, 1H), 8.15 (m, 1H), 8.65 (s, 1H).

EXAMPLE 22

(1R,2R)-N-(1-cyanocyclopropyl)-2-{[6-(methylthio)-1,3,4,5-tetrahydro-2H-pyrido[4,3-b]indol-2-yl]carbonyl}cyclohexanecarboxamide

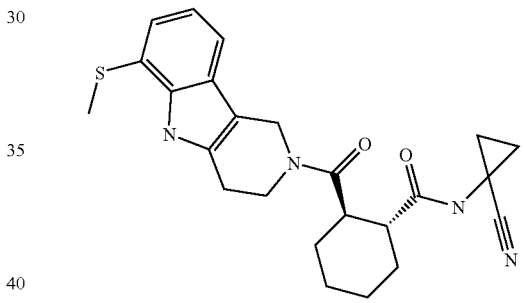

Following Example 1, but starting with 6-methylsulfanyl-2,3,4,5-tetrahydro-1H-pyrido[4,3-b]indole (510 mg, 2.00 mmol) furnished the desired compound as a white solid (224 mg, 24% yield).
MS (+ve ESI): 454 (M+H)$^+$
$^1$H NMR (400.132 MHz, DMSO) δ 0.70-1.05 (m, 2H), 1.22-1.54 (m, 4H), 2.31-2.47 (m, 1H), 2.65-2.75 (m, 1H), 2.85 (t, 2H), 2.91-3.07 (m, 2H), 3.20 (t, 1H), 3.34 (s, 3H), 3.48-3.93 (m, 4H), 4.48-4.75 (m, 2H), 6.97 (q, 1H), 7.05 (q, 1H), 7.36 (q, 1H), 8.69 (s, 2H), 10.94 (s, 1H)

6-methylsulfanyl-2,3,4,5-tetrahydro-1H-pyrido[4,3-b]indole was synthesised in the following manner:

[2-(methylthio)phenyl]hydrazine

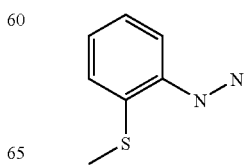

A partial solution of the 2-methylmercapto aniline (10.0 mL, 80.0 mmol) in conc. hydrochloric acid (100 mL) and trifluoroacetic acid (60 mL) was cooled to ca 0° C. and maintained there during the addition of a solution of the sodium nitrite (6.63 g, 96.0 mmol) in water (22 mL) over 30 min. The reaction was stirred at the same temp for a further 1 h when tin chloride (30.3 g, 160 mmol) in hydrochloric acid (50 mL) was added over 15 min. The reaction was allowed to warm with stirring overnight. The resulting solid was filtered off, washed with IPA and dried (17.8 g)

MS (+ve ESI) 454 (M+H)+

1H NMR (400.132 MHz, DMSO) ☐ 2.43 (s, 3H), 7.03 (q, 2H), 7.21-7.28 (m, 1H), 7.35 (d, 1H), 7.74 (s, 1H), 10.23 (s, 2H)

6-(methylthio)-2,3,4,5-tetrahydro-1H-pyrido[4,3-b]indole

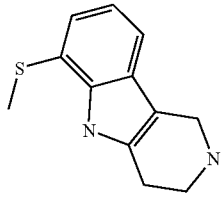

The 2-(methylthio)phenyl hydrazine (5.32 g, 30.0 mmol) and 4-piperidone (4.07 g, 30.0 mmol) were partially dissolved in the ethanol (75 mL) and heated initially to reflux for 1 h. A heavy precipitate formed from the almost clear solution. The reaction was then treated with the conc hydrochloric acid (2.5 mL) and diluted with further ethanol (25 mL) to assist stirring and heating continued for a further 4 h. After cooling to RT overnight the solid was filtered washing isopropanol (25 mL). Obtained 7.70 g MS (+ve ESI): 454 (M+H)+

¹H NMR (400.132 MHz, DMSO) δ 1.90 (t, 2H), 2.98 (s, 2H), 3.04 (t, 1H), 3.39 (s, 3H), 4.27 (s, 1H), 7.02 (t, 1H), 7.10 (d, 1H), 7.30-7.46 (m, 1H), 9.15 (s, 1H), 9.61 (s, 1H), 11.17 (s, 1H).

EXAMPLE 23

(1R,2R)-N-(1-cyanocyclopropyl)-2-[(benzofuro[3,2-c]-1,2,3,4-tetrahydropyridyl)carbonyl]cyclohexanecarboxamide

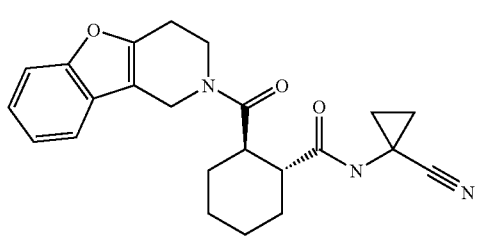

Following Example 1, but starting with benzofuro[3,2-c]-1,2,3,4-tetrahydropyridine (562 mg, 3.24 mmol) furnished the desired compound as a white solid (331 mg, 26% yield).

MS (+ve ESI): 392 (M+H)+

¹H NMR (400 MHz, DMSO) δ 0.8-1.1 (m, 2H), 1.3 (m, 6H), 1.75 (m, 4H), 2.4 (m, 1H), 2.65-3.2 (m, 3H), 3.8 (m, 2H), 4.5-4.8 (m, 2H), 7.25 (m, 2H), 7.6 (m, 2H), 8.75 (m, 1H).

Benzofuro[3,2-c]-1,2,3,4-tetrahydropyridine used as a starting material was prepared as follows:

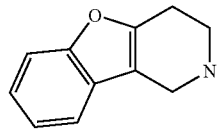

O-Phenylhydroxylamine hydrochloride (2.00 g, 13.7 mmol) and 4-piperidone hydrochloride (1.87 g, 13.7 mmol) were suspended in ethanol (15 mL). Concentrated hydrochloric acid (5 mL) was added and the mixture stirred at reflux for 3 hours. It was allowed to cool to room temperature then chilled in an ice bath and the resulting precipitate filtered and washed with a small volume of cold ethanol. It was then slurried in water (20 mL) and extracted with DCM (3×30 mL). The combined organics were washed with brine (20 mL), dried (sodium sulphate), concentrated in vacuo and adsorbed onto silica for purification by flash chromatography (100% DCM to 5% methanolic ammonia in 50% ethanol/dichloromethane). This gave benzofuro[3,2-c]-1,2,3,4-tetrahydropyridine as a white solid (1.28 g, 54%).

MS (+ve ESI): 392 (M+H)+

1H NMR (400 MHz, DMSO) δ 2.7 (t, 2H), 3.05 (t, 2H), 3.8 (s, 2H), 6.9 (m, 1H), 7.2 (m, 2H), 7.5 (m, 2H).

EXAMPLE 24

(1R,2R)-N-(1-cyanocyclopropyl)-2-{[6-(trifluoromethoxy)-1,3,4,5-tetrahydro-2H-pyrido[4,3-b]indol-2-yl]carbonyl}cyclohexanecarboxamide

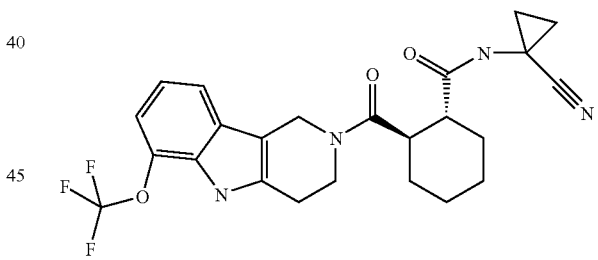

6-Trifluoromethoxy-2,3,4,5-tetrahydro-1H-pyrido[4,3-b]indole (232 mg, 0.79 mmol) and (3aR,7aR)-hexahydro-2-benzofuran-1,3-dione (122 mg, 0.79 mmol) in DCM (15 mL) under argon was treated with diisopropylethylamine (550 uL, 3.16 mmol) and stirred 1 h. The solvent was largely evaporated and replaced with DMF (5 mL) before addition of aminocyclopropanecarbonitrile hydrochloride (140 mg, 1.19 mmol), HATU (451 mg, 1.19 mmol) and further diisopropylethylamine (550 uL, 3.16 mmol). The reaction was stirred overnight. Reaction mixture was split into two and diluted with aqueous acetonitrile purifying by preparative HPLC (2 injections) (Formic Acid Float peaks method CH₃CN/H²O gradient). The product fractions were combined and evaporated to give white powder (121 mg, 32%).

MS (+ve ESI): 475 (M+H)+

¹H NMR (400.132 MHz, DMSO) ☐ 0.68-1.05 (m, 2H), 1.11-1.47 (m, 6H), 1.58-1.87 (m, 4H), 2.64-3.09 (m, 4H), 3.66-3.94 (m, 2H), 4.60 (q, 1H), 4.76 (s, 1H), 6.98-7.09 (m, 2H), 7.41-7.57 (m, 1H), 8.71 (s, 1H), 11.50 (s, 1H)

6-Trifluoromethoxy-2,3,4,5-tetrahydro-1H-pyrido[4,3-b]indole was prepared in the following manner.

[2-(trifluoromethoxy)phenyl]hydrazine hydrochloride

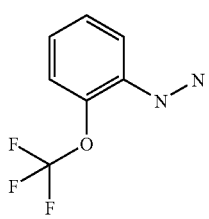

2-(Trifluoromethoxy)aniline (2.00 mL, 15.0 mmol) was cooled and conc hydrochloric acid (10 mL) added. After recooling to 0° C. a solution of the sodium nitrite (1.25 g, 18.0 mmol) in water (10 mL) was added dropwise. The reaction was stirred at the same temp for 30 min when tin chloride (8.53 g 45.0 mmol) in hydrochloric acid (10 mL) was added dropwise again keeping temp ca 0° C. The reaction was stored in a fridge overnight and then recooled to 0° C. The resulting solid was filtered off, washed with saturated NaCl (10 mL) and then ether:hexane 1:2 before drying to give a solid (2.36 g, 69%)

MS (+ve ESI): 193 (M+H)$^+$

1H NMR (400.132 MHz, DMSO) δ 7.04 (t, 1H), 7.25 (d, 1H), 7.30-7.39 (m, 2H), 8.34 (s, 1H), 10.26 (s, 2H)

6-(trifluoromethoxy)-2,3,4,5-tetrahydro-1H-pyrido [4,3-b]indole

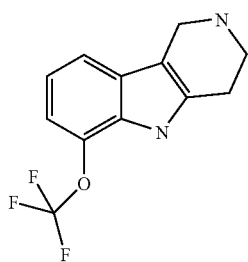

2-(methylthio)phenyl hydrazine (442 mg, 2.30 mmol) and 4-piperidone (312 mg, 2.30 mmol) were partially dissolved in the ethanol (5 mL) and heated initially to reflux for 1 h. A heavy precipitate formed from the almost clear solution. The reaction was then treated with conc hydrochloric acid (1 mL) and diluted with further ethanol (5 mL) to assist stirring and heating continued for a further 4 h. After cooling to room temperature overnight the solid was filtered and washed with isopropanol (25 mL), material used crude.

MS (+ve ESI): 219 (M+H)$^+$

EXAMPLE 25

(1R,2R)-N-(1-cyanocyclopropyl)-2-[(6-ethoxy-1,3,4,5-tetrahydro-2H-pyrido[4,3-b]indol-2-yl)carbonyl]cyclohexanecarboxamide

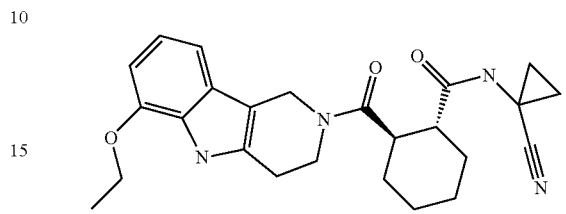

Following Example 24 but starting 6-ethoxy-2,3,4,5-tetrahydro-1H-pyrido[4,3-b]indole (253 mg, 1.00 mmol) furnished the desired compound as a white solid (261 mg, 60% yield).

MS (+ve ESI): 435 (M+H)$^+$

1H NMR (400.132 MHz, DMSO) δ 0.73-1.03 (m, 2H), 1.11-1.44 (m, 9H), 1.60-1.85 (m, 4H), 2.41-2.50 (m, 1H), 2.54-3.06 (m, 3H), 3.63-3.94 (m, 2H), 4.17 (q, 2H), 4.55 (q, 1H), 4.70 (s, 1H), 6.62 (t, 1H), 6.83-6.92 (m, 1H), 7.02 (q, 1H), 8.69 (s, 1H), 10.87 (s, 1H).

6-ethoxy-2,3,4,5-tetrahydro-1H-pyrido[4,3-b]indole was synthesised in the following manner:

(2-ethoxyphenyl)hydrazine

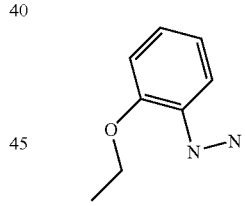

2-phenetidine (6.53 mL, 50.0 mmol) was cooled and conc hydrochloric acid (80 mL) added. After recooling to 0° C. a solution of the sodium nitrite (4.14 g, 60.0 mmol) in water (20 mL) was added dropwise. The reaction was stirred at the same temp for 30 min when tin chloride (33.9 g 150 mmol) in hydrochloric acid (40 mL) was added dropwise again keeping temp ca 0° C. The resulting solid was filtered off, washed with sat NaCl and then ether:hexane 1:2 before suspending in ice/water and ether and basified with 10M NaOH. The ether layer was separated from the aqueous and suspended solid material. After combining with a further extract the ether was dried and evaporated to give a yellow crystalline solid 10. (9.71 g, 69%)

MS (+ve ESI): 177 (M+H)$^+$

1H NMR (400.132 MHz, DMSO) δ 1.33 (t, 3H), 3.93 (s, 1H), 3.98 (q, 2H), 5.85 (s, 1H), 6.58 (t, 1H), 6.76-6.83 (m, 1H), 7.00 (d, 1H)

6-Ethoxy-2,3,4,5-tetrahydro-1H-pyrido[4,3-b]indole

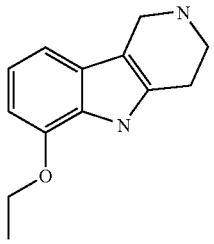

(2-ethoxyphenyl)-hydrazine (1.22 g 8.00 mmol) and 4-piperidone hydrochloride (1.09 g 8.00 mmol) in ethanol (20 mL) were heated to reflux for 1 h. The 4M HCl (1 mL) in dioxane was added (immediate darkening) and heating continued for 4 h. The reaction was cooled to RT. The solvent was evaporated and the residue triturated with ether (c.f. 10 mL) to give a dark brown solid. The solid was slurried with the minimum of water, filtered and dried (MgSO4). This was repeated to give an off white solid (1.19 g, 59%). Material used without further purification.

MS (+ve ESI): 177 (M+H)+

$^1$H NMR (400.132 MHz, DMSO) δ 1.42 (t, 3H), 3.00 (t, 1H), 3.44 (q, 2H), 4.18 (q, 2H), 4.26 (s, 1H), 6.67 (d, 1H), 6.91 (t, 1H), 7.03 (d, 1H), 9.38 (s, 1H), 11.12 (s, 1H).

EXAMPLE 26

(1R,2R)-N-(1-cyanocyclopropyl)-2-[(5-methoxycarbonylmethyl-1,3,4,5-tetrahydro-2H-pyrido[4,3-b]indol-2-yl)carbonyl]cyclohexanecarboxamide

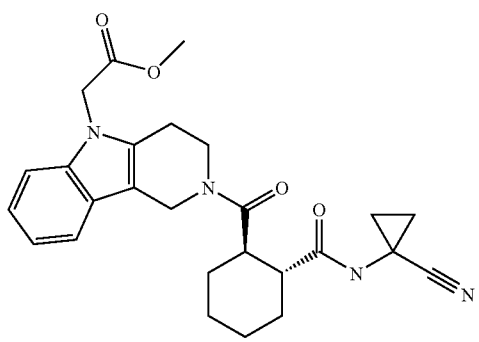

Following Example 24, but starting 5-methoxycarbonylmethyl-2,3,4,5-tetrahydro-1H-pyrido[4,3-b]indole hydrochloride (305 mg, 1.09 mmol) furnished the desired compound as a straw coloured solid (199 mg, 40% yield).

MS (+ve ESI): 463 (M+H)+

1H NMR (400 MHz, DMSO) δ 0.8-1.1 (m, 2H), 1.3 (m, 6H), 1.75 (m, 4H), 2.4 (m, 1H), 2.65-3.1 (m, 3H), 3.7 (m, 3H), 3.9 (m, 2H), 4.5-4.85 (m, 2H), 5.05 (m, 2H), 7.1 (m, 2H), 7.35-7.6 (m, 2H), 8.7 (s, 1H).

5-methoxycarbonylmethyl-2,3,4,5-tetrahydro-1H-pyrido[4,3-b]indole hydrochloride was synthesised in the following manner.

tert-butyl 5-methoxycarbonylmethyl-1,3,4,5-tetrahydro-2H-pyrido[4,3-b]indole-2-carboxylate

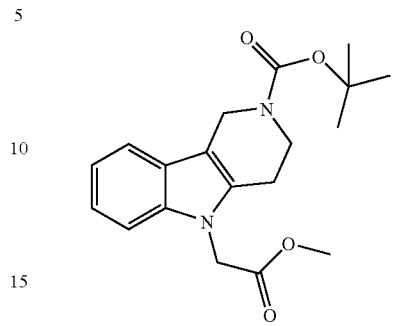

N-boc-2,3,4,5-tetrahydro-1H-pyrido[4,3-b]indole (450 mg, 1.65 mmol) was dissolved in DMF (7 mL) and stirred at room temperature. The vessel was flushed with argon and sodium hydride (67.0 mg, 1.65 mmol) was added. After 30 minutes, methyl bromoacetate (253 mg, 1.65 mmol) in DMF (2 mL) was added and the mixture stirred overnight. The solvent was removed in vacuo and the residue partitioned between brine (20 mL) and ethyl acetate (2×40 mL). Combined organics were dried (sodium sulphate), concentrated in vacuo and adsorbed onto silica for purification by flash chromatography (0-40% ethyl acetate/isohexane). This gave tert-butyl 5-methoxycarbonylmethyl-1,3,4,5-tetrahydro-2H-pyrido[4,3-b]indole-2-carboxylate as a pale yellow foam (387 mg, 68%).

MS (+ve ESI): 245.2 (M+H)+

1H NMR (400 MHz, DMSO) δ 1.45 (s, 9H), 2.7 (m, 2H), 3.7 (s, 3H), 3.75 (t, 2H), 4.55 (s, 2H), 5.05 (s, 2H), 7.1 (m, 2H), 7.4 (m, 2H).

5-methoxycarbonylmethyl-2,3,4,5-tetrahydro-1H-pyrido[4,3-b]indole hydrochloride

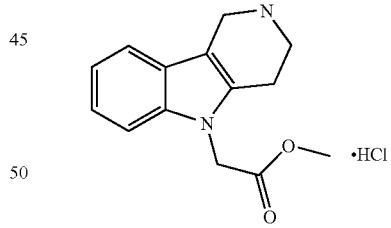

tert-Butyl 5-methoxycarbonylmethyl-1,3,4,5-tetrahydro-2H-pyrido[4,3-b]indole-2-carboxylate (377 mg, 1.09 mmol) was dissolved in methanol (15 mL). 4N HCl in 1,4-dioxan (1.5 mL) was added and the mixture stirred at room temperature overnight. The solution was concentrated in vacuo, azeotroped once with toluene and dried under vacuum to give 5-methoxycarbonylmethyl-2,3,4,5-tetrahydro-1H-pyrido[4,3-b]indole hydrochloride as an off white solid (314 mg, 100% assuming HCl salt).

MS (+ve ESI): 245.2 (M+H)+

1H NMR (400 MHz, DMSO) δ 3.0 (t, 2H), 3.5 (m, 2H), 3.7 (s, 3H), 4.3 (s, 2H), 5.15 (s, 2H), 7.05 (t, 1H), 7.15 (t, 1H), 7.4 (d, 1H), 7.5 (d, 1H), 9.5 (m, 2H).

EXAMPLE 27

(1R,2R)-N-(1-cyanocyclopropyl)-2-[(5-hydroxycarbonylmethyl-1,3,4,5-tetrahydro-2H-pyrido[4,3-b]indol-2-yl)carbonyl]cyclohexanecarboxamide

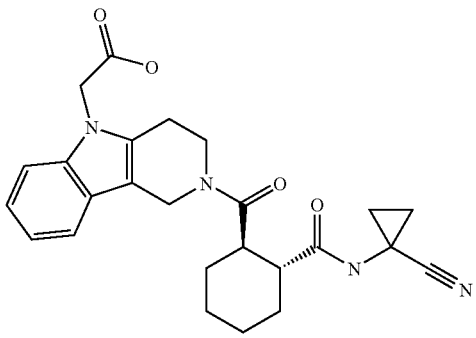

(1R,2R)-N-(1-cyanocyclopropyl)-2-[(5-methoxycarbonylmethyl-1,3,4,5-tetrahydro-2H-pyrido[4,3-b]indol-2-yl)carbonyl]cyclohexanecarboxamide (150 mg, 0.32 mmol) and lithium iodide (520 mg, 3.89 mmol) were suspended in pyridine (5 mL) in a capped microwave vessel. This was heated in a microwave at 150° C. for one hour (absorbance: N). Pyridine was removed in vacuo and the residue azeotroped once with toluene. It was taken up in 50% brine (20 mL), acidified with acetic acid and partitioned with ethyl acetate (2×80 mL). Combined organics were dried (magnesium sulphate), concentrated in vacuo, azeotroped once with toluene and adsorbed onto silica for purification by flash chromatography (0-20% methanol/DCM). This gave (1R,2R)-N-(1-cyanocyclopropyl)-2-[(5-hydroxycarbonylmethyl-1,3,4,5-tetrahydro-2H-pyrido[4,3-b]indol-2-yl)carbonyl]cyclohexanecarboxamide as a pale yellow solid (84.0 mg, 59%).

MS (+ve ESI): 449 (M+H)+

1H NMR (400 MHz, DMSO) δ 0.8-1.1 (m, 2H), 1.3 (m, 6H), 1.75 (m, 4H), 2.4 (m, 1H), 2.65-3.1 (m, 3H), 3.7-4.0 (m, 2H), 4.5-4.85 (m, 4H), 7.1 (m, 2H), 7.25 (m, 1H), 7.4-7.55 (m, 1H), 8.8 (s, 1H).

EXAMPLE 28

(1R,2R)-N-(1-cyanocyclopropyl)-2-[(5-cyclopropylmethyl-1,3,4,5-tetrahydro-2H-pyrido[4,3-b]indol-2-yl)carbonyl]cyclohexanecarboxamide

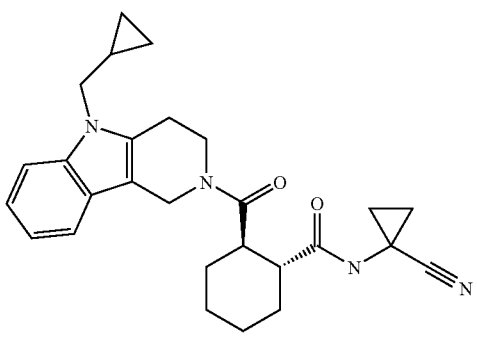

Following Example 24, but starting 5-cyclopropylmethyl-2,3,4,5-tetrahydro-1H-pyrido[4,3-b]indole hydrochloride (365 mg, 1.39 mmol) furnished the desired compound as a brittle white solid (199 mg, 40% yield).

MS (+ve ESI): 445 (M+H)+

1H NMR (400 MHz, DMSO) δ 0.35 (m, 2H), 0.45 (m, 2H), 0.75-1.0 (m, 2H), 1.15-1.4 (m, 7H), 1.75 (m, 4H), 2.4 (m, 1H), 2.75-3.1 (m, 3H), 3.7-4.0 (m, 4H), 4.55-4.75 (m, 2H), 7.05 (m, 2H), 7.5 (m, 2H), 8.7 (s, 1H).

5-Cyclopropylmethyl-2,3,4,5-tetrahydro-1H-pyrido[4,3-b]indole hydrochloride was synthesised in the following manner.

tert-Butyl 5-cyclopropylmethyl-1,3,4,5-tetrahydro-2H-pyrido[4,3-b]indole-2-carboxylate

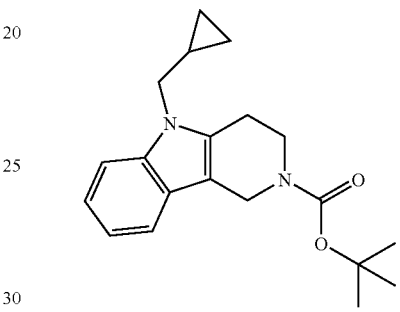

N-boc-2,3,4,5-tetrahydro-1H-pyrido[4,3-b]indole (450 mg, 1.65 mmol) was dissolved in DMF (7 mL) and stirred at room temperature. The vessel was flushed with argon and sodium hydride (67 mg, 1.65 mmol) was added. After 30 minutes, cyclopropylmethyl bormide (0.16 mL, 1.65 mmol) in DMF (2 mL) was added and the mixture stirred overnight. The solvent was removed in vacuo and the residue partitioned between brine (20 mL) and ethyl acetate (2×40 mL). Combined organics were dried (sodium sulphate), concentrated in vacuo and adsorbed onto silica for purification by flash chromatography (0-40% ethyl acetate/isohexane). This gave tert-Butyl 5-cyclopropylmethyl-1,3,4,5-tetrahydro-2H-pyrido[4,3-b]indole-2-carboxylate as a pale yellow gum (451 mg, 84%).

MS (+ve ESI): 327 (M+H)+

1H NMR (400 MHz, DMSO) δ 0.0 (m, 2H), 0.1 (m, 2H), 0.8 (m, 1H), 1.1 (s, 9H), 2.5 (t, 2H), 3.4 (t, 2H), 3.65 (d, 2H), 4.2 (s, 2H), 6.65 (t, 1H), 6.75 (t, 1H), 7.1 (m, 2H).

5-cyclopropylmethyl-2,3,4,5-tetrahydro-1H-pyrido[4,3-b]indole hydrochloride

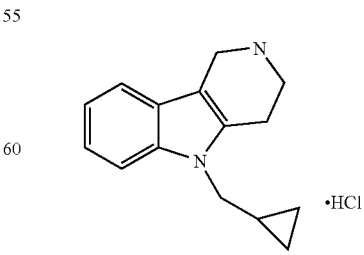

tert-Butyl 5-cyclopropylmethyl-1,3,4,5-tetrahydro-2H-pyrido[4,3-b]indole-2-carboxylate (440 mg, 1.35 mmol) was dissolved in methanol (15 mL). 4N HCl in 1,4-dioxan (1.5 mL) was added and the mixture stirred at room temperature overnight. The solution was concentrated in vacuo, azeotroped once with toluene to give 5-cyclopropylmethyl-2,3,4,5-tetrahydro-1H-pyrido[4,3-b]indole hydrochloride as an off white solid (374 mg, 100% assuming HCl salt).

MS (+ve ESI): 227 (M+H)

1H NMR (400 MHz, DMSO) δ 0.15 (m, 2H), 0.25 (m, 2H), 0.9 (m, 1H), 2.85 (t, 2H), 3.25 (m, 2H), 3.8 (d, 2H), 4.1 (s, 2H), 6.8 (t, 1H), 6.9 (t, 1H), 7.25 (m, 2H), 9.2 (m, 2H).

EXAMPLE 29

(1R,2R)-N-(1-cyanocyclopropyl)-2-[(5-methoxyethyl-1,3,4,5-tetrahydro-2H-pyrido[4,3-b]indol-2-yl)carbonyl]cyclohexanecarboxamide

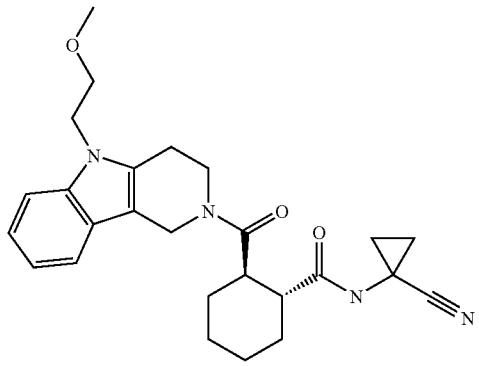

Following Example 24, but starting with 5-methoxyethyl-2,3,4,5-tetrahydro-1H-pyrido[4,3-b]indole hydrochloride (340 mg, 1.27 mmol) furnished the desired compound as a brittle straw coloured solid (148 mg, 26%).

MS (+ve ESI): 449 (M+H)+

1H NMR (400 MHz, DMSO) δ 0.75-1.0 (m, 2H), 1.15-1.4 (m, 6H), 1.75 (m, 4H), 2.4 (m, 1H), 2.75-3.1 (m, 3H), 3.2 (m, 3H), 3.55-4.0 (m, 4H), 4.25 (m, 2H), 4.55-4.8 (m, 2H), 7.05 (m, 2H), 7.5 (m, 2H), 8.7 (s, 1H).

5-methoxyethyl-2,3,4,5-tetrahydro-1H-pyrido[4,3-b]indole hydrochloride was synthesised in the following manner:

tert-Butyl 5-cyclopropylmethyl-1,3,4,5-tetrahydro-2H-pyrido[4,3-b]indole-2-carboxylate

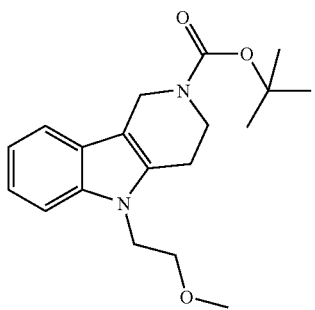

N-boc-2,3,4,5-tetrahydro-1H-pyrido[4,3-b]indole (450 mg, 1.65 mmol) was dissolved in DMF (7 mL) and stirred at room temperature. The vessel was flushed with argon and sodium hydride (67 mg, 1.65 mmol) was added. After 30 minutes, 1-bromo-2-methoxyethane (230 mg, 1.65 mmol) in DMF (2 mL) was added and the mixture stirred overnight. The solvent was removed in vacuo and the residue partitioned between brine (20 mL) and ethyl acetate (2×40 mL). Combined organics were dried (sodium sulphate), concentrated in vacuo and adsorbed onto silica for purification by flash chromatography (0-40% ethyl acetate/isohexane). This gave tert-Butyl 5-(2-methoxy)ethyl-1,3,4,5-tetrahydro-2H-pyrido[4,3-b]indole-2-carboxylate as a pale yellow gum (443 mg, 81%).

MS (+ve ESI): 331 (M+H)+

1H NMR (400 MHz, DMSO) δ 1.45 (s, 9H), 2.8 (t, 2H), 3.2 (s, 3H), 3.55 (t, 2H), 3.75 (t, 2H), 4.25 (t, 2H), 4.55 (s, 2H), 7.0 (t, 1H), 7.1 (t, 1H), 7.4 (m, 2H).

5-methoxyethyl-2,3,4,5-tetrahydro-1H-pyrido[4,3-b]indole hydrochloride

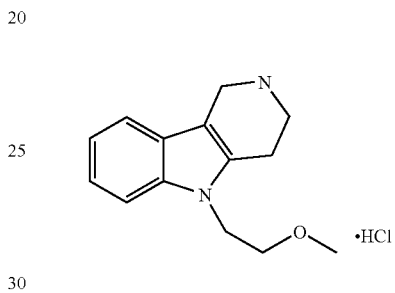

tert-Butyl 5-(2-methoxy)ethyl-1,3,4,5-tetrahydro-2H-pyrido[4,3-b]indole-2-carboxylate (430 mg) was dissolved in methanol (15 mL). 4N HCl in 1,4-dioxan (1.5 mL) was added and the mixture stirred at room temperature overnight. The solution was concentrated in vacuo, azeotroped once with toluene and dried under vacuum. This gave 5-(2-methoxy)ethyl-2,3,4,5-tetrahydro-1H-pyrido[4,3-b]indole hydrochloride as a grey foam (350 mg, 100% assuming HCl salt).

MS (+ve ESI): 331 (M+H)+

1H NMR (400 MHz, DMSO) δ 3.2 (t, 2H), 3.4 (s, 3H), 3.6 (m, 4H), 4.3 (m, 4H), 7.15 (m, 2H), 7.5 (d, 2H), 9.6 (m, 2H).

EXAMPLE 30

(1R,2R)-N-(1-cyanocyclopropyl)-2-{[6-(trifluoromethyl)-1,3,4,5-tetrahydro-2H-pyrido[4,3-b]indol-2-yl]carbonyl}cyclohexanecarboxamide

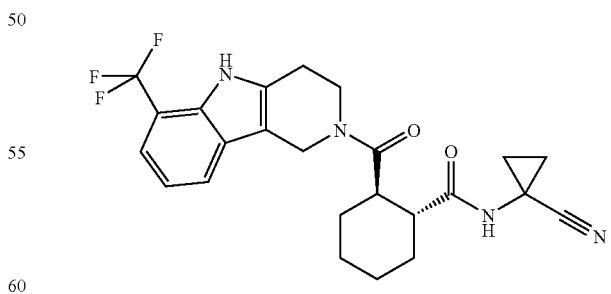

Following Example 24, but starting with 6-(trifluoromethyl)-2,3,4,5-tetrahydro-1H-pyrido[4,3-b]indole (481 mg, 2.00 mmol) furnished the desired compound as a white solid (314 mg, 34%).

1H NMR (400.13 MHz, CDCl3) δ 0.87-1.89 (12H, m), 2.58-2.64 (1H, m), 2.83-3.10 (3H, m), 3.64-3.71 (0.5H, m), 3.87-3.99 (1H, m), 4.35-4.41 (0.5H, m), 4.74-4.77 (1.5H, m), 4.88 (0.5H, d), 6.49 and 6.57 (2×0.5H, 2×s), 7.14-7.21 (1H, m), 7.42 (1H, t), 7.62 (1H, t), 8.29 (1H, d)

6-(Trifluoromethyl)-2,3,4,5-tetrahydro-1H-pyrido[4,3-b]indole was synthesised in the following manner:

6-(Trifluoromethyl)-2,3,4,5-tetrahydro-1H-pyrido[4,3-b]indole

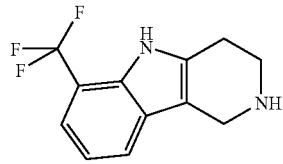

To 4-piperidone.HCl (1.36 g, 10.0 mmol) and 2-trifluoromethylphenylhydrazine.HCl (2.13 g, 10.0 mmol) in acetic acid (50 mL) was added the 1.0 M borontrifluoride etherate (2.46 mL, 20.0 mmol) and the reaction stirred at 90° C. for 8 hours and then allowed to cool. The mixture was concentrated in vacuo and ethanol (ca 20 mL) added and then cooled to 0° C., the solid was filtered off and the mother liquor was concentrated in vacuo and water (adjusted to pH 14 with 2M NaOH) added to the residue. The solid was filtered off and washed with water and dried under high vacuum.

MS (+ve ESI): 240 (M+H)⁺

¹H NMR (400.132 MHz, DMSO) δ 3.07 (2H, t), 3.47 (2H, t), 4.33 (2H, s), 7.19 (1H, t), 7.45 (1H, d), 7.79 (1H, d), 11.52 (1H, s)

EXAMPLE 31

(1R,2R)-N-(1-cyanocyclopropyl)-2-{[6-(methylsulfonyl)-1,3,4,5-tetrahydro-2H-pyrido[4,3-b]indol-2-yl]carbonyl}cyclohexanecarboxamide

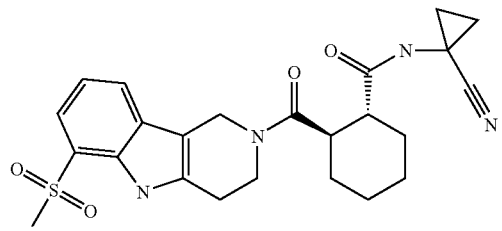

Following Example 24, but starting with 6-methanesulfonyl-2,3,4,5-tetrahydro-1H-pyrido[4,3-b]indole (155 mg, 0.61 mmol) furnished the desired compound as a off white coloured solid (23.4 mg, 8.2%).

MS (+ve ESI): 469 (M+H)⁺

¹H NMR (400.132 MHz, DMSO) δ 0.70-1.08 (m, 2H), 1.09-1.49 (m, 6H), 1.52-1.87 (m, 4H), 2.32-2.47 (m, 1H), 2.54-3.21 (m, 3H), 3.33 (s, 3H), 3.69-3.97 (m, 2H), 4.64 (q, 1H), 4.80 (s, 1H), 7.16-7.25 (m, 1H), 7.56 (t, 1H), 7.87 (q, 1H), 8.71 (d, 1H), 11.24 (d, 1H)

6-methanesulfonyl-2,3,4,5-tetrahydro-1H-pyrido[4,3-b]indole was synthesised in the following manner:

6-methylsulfanyl-1,3,4,5-tetrahydro-pyrido[4,3-b]indole-2-carboxylic acid tert-butyl ester

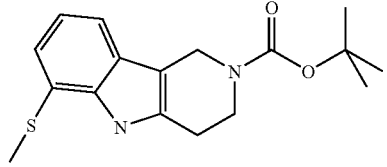

6-methylsulfanyl-2,3,4,5-tetrahydro-1H-pyrido[4,3-b]indole (1.10 g 5.00 mmol) in dry THF (20 mL) was treated with di-t-butyl-dicarbonate (2.40 g, 11.0 mmol) followed by a few crystals of 4-dimethylaminopyridine. The reaction was stirred at 60° C. for 2 hours. Trituration with a little ether gave pure product as a white solid (191 mg). Material used crude MS (+ve ESI): 319 (M-tBu)⁺

¹H NMR (400.132 MHz, DMSO) δ 1.50 (s, 9H), 2.85 (t, 2H), 3.34 (s, 3H), 3.76 (t, 2H), 4.57 (s, 2H), 7.03 (t, 1H), 7.12 (d, 1H), 7.34 (d, 1H), 10.93 (s, 1H)

6-methanesulfonyl-1,3,4,5-tetrahydro-pyrido[4,3-b]indole-2-carboxylic acid tert-butyl ester

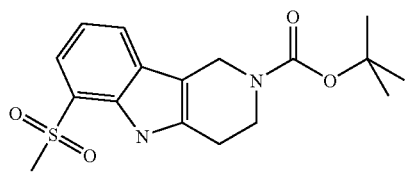

6-methylsulfanyl-1,3,4,5-tetrahydro-pyrido[4,3-b]indole-2-carboxylic acid tert-butyl ester (99.0 mg, 0.31 mmol) in DCM (10 mL) was cooled to >0° C. and the MCPBA (148 mg, 0.62 mmol) in DCM (5 mL) added dropwise over 30 min. The reaction was allowed to warm to RT. The reaction was washed with sat. NaHCO₃ solution (2×20 mL), dried (MgSO₄) and evaporated to give a yellow gum (109 mg, 100%)

MS (+ve ES): 249 (M-tBu)⁺

1H NMR (400.132 MHz, DMSO) 61.45 (s, 9H), 2.86 (t, 2H), 3.26 (s, 3H), 3.72 (t, 2H), 4.58 (s, 2H), 7.20 (t, 1H), 7.56 (d, 1H), 7.80 (d, 1H), 11.17 (s, 1H)

6-methanesulfonyl-2,3,4,5-tetrahydro-1H-pyrido[4,3-b]indole

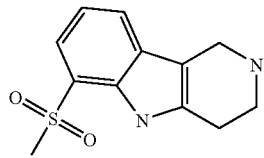

6-methanesulfonyl-1,3,4,5-tetrahydro-pyrido[4,3-b]indole-2-carboxylic acid tert-butyl ester (214 mg, 0.61 mmol) was dissolved in DCM (1 mL) and the 4M HCl in dioxane (1 mL) added. Evolution of gas commenced immediately and the reaction was stirred for 2.5 h when no further evolution was observed but a black solid had separated from the reaction.

LCMS Retention time 0.62 min MS (+ve ESI): 251 (M+H)+

EXAMPLE 32

(1R,2R)-2-{[6-(benzyloxy)-1,3,4,5-tetrahydro-2H-pyrido[4,3-b]indol-2-yl]carbonyl}-N-(1-cyanocyclopropyl)cyclohexanecarboxamide

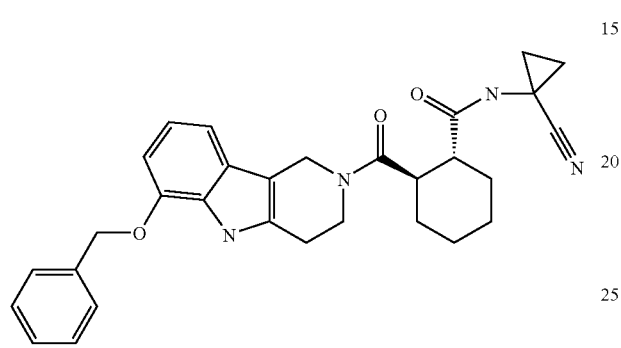

Following Example 24, but starting with 6-benzyloxy-2,3,4,5-tetrahydro-1H-pyrido[4,3-b]indole.HCl (945 mg, 3.00 mmol) furnished the desired compound as a off white coloured solid (822 mg, 55%).

MS (+ve ESI): 497 (M+H)+

$^1$H NMR (400.132 MHz, DMSO) δ 0.72-1.04 (m, 2H), 1.15-1.44 (m, 6H), 1.60-1.86 (m, 4H), 2.42-2.49 (m, 1H), 2.64-3.09 (m, 3H), 3.63-3.96 (m, 2H), 4.56 (q, 1H), 4.71 (s, 1H), 5.25 (s, 2H), 6.73 (t, 1H), 6.88 (quintet, 1H), 7.05 (q, 1H), 7.34 (t, 1H), 7.41 (t, 2H), 7.56 (d, 2H), 8.64 (s, 1H), 10.94 (s, 1H)

6-Benzyloxy-2,3,4,5-tetrahydro-1H-pyrido[4,3-b]indole-.HCl was prepared in the following manner.

(2-Benzyloxyphenyl)-hydrazine

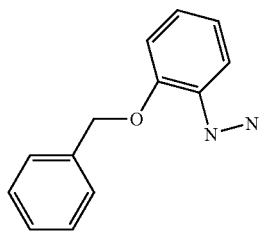

The 2-benzyloxyaniline (4.99 g, 25.0 mmol) partially dissolved in conc hydrochloric acid (15 mL) was cooled to less than 0° C. and a solution of the sodium nitrite (2.07 g, 30.0 mmol) in water (10 mL) was added dropwise. The reaction was stirred at the same temp for 30 min, when tin chloride (16.9 g, 75.0 mmol) in hydrochloric acid (10 mL) was added dropwise again keeping temp ca 0° C. The reaction was stored overnight in the fridge. The aqueous was decanted off the resulting black oily gum and triturated with sat NaCl (cf. 50 mL) and then ether:hexane 1:2 (50 mL) before neutralising with 10M NaOH (aq) with external cooling and extracted into ether (2×100 mL). The combined ether layers were washed with water (100 mL) dried (MgSO4) and evaporated to give a brown oil which crystallised on standing (4.52 g, 84%). Material was used crude without further purification.

$^1$H NMR (400.132 MHz, DMSO) δ 3.95 (s, 2H), 5.09 (s, 2H), 5.96 (s, 1H), 6.58 (t, 1H), 6.79-6.90 (m, 2H), 7.04 (d, 1H), 7.29-7.36 (m, 1H), 7.40 (t, 2H), 7.49 (d, 2H).

6-Benzyloxy-2,3,4,5-tetrahydro-1H-pyrido[4,3-b]indole.HCl

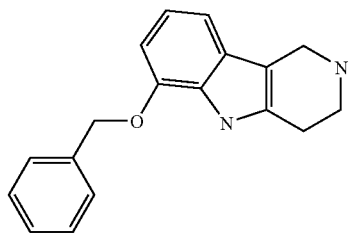

The (2-benzyloxyphenyl)-hydrazine (3.39 g, 15.8 mmol) and 4-piperidone hydrochloride (2.15 g, 15.8 mmol) in ethanol (30 mL) were heated to reflux for 45 min. The 4M HCl in dioxane (1.0M, 6 mL) was added and heating continued. After 30 min a heavy precipitate had formed. The reaction was cooled in an ice bath and the solid was filtered, washed with a little cold isopropyl alcohol then ether (c.f. 5 mL) before drying to give 2.61 g 52.5% white solid.

$^1$H NMR (400.132 MHz, DMSO) δ 3.01 (t, 2H), 3.40-3.49 (m, 2H), 4.27 (s, 2H), 5.27 (s, 2H), 6.78 (d, 1H), 6.92 (t, 1H), 7.31-7.38 (m, 1H), 7.42 (t, 3H), 7.56 (d, 2H), 9.34 (s, 2H), 11.22 (s, 1H)

(2-Benzyloxyphenyl)-hydrazine

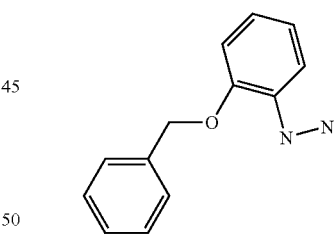

The 2-benzyloxyaniline (4.99 g, 25.0 mmol) partially dissolved in conc hydrochloric acid (15 mL) was cooled to less than 0° C. and a solution of the sodium nitrite (2.07 g, 30.0 mmol) in water (10 mL) was added dropwise. The reaction was stirred at the same temp for 30 min, when tin chloride (16.9 g, 75.0 mmol) in hydrochloric acid (10 mL) was added dropwise again keeping temp ca 0° C. The reaction was stored overnight in the fridge. The aqueous was decanted off the resulting black oily gum and triturated with sat NaCl (cf. 50 mL) and then ether:hexane 1:2 (50 mL) before neutralising with 10M NaOH (aq) with external cooling and extracted into ether (2×100 mL). The combined ether layers were washed with water (100 mL) dried (MgSO$_4$) and evaporated to give a brown oil which crystallised on standing (4.52 g, 84%). Material was used crude without further purification.

¹H NMR (400.132 MHz, DMSO) δ 3.95 (s, 2H), 5.09 (s, 2H), 5.96 (s, 1H), 6.58 (t, 1H), 6.79-6.90 (m, 2H), 7.04 (d, 1H), 7.29-7.36 (m, 1H), 7.40 (t, 2H), 7.49 (d, 2H).

EXAMPLE 33

(1R,2R)-N-(1-cyanocyclopropyl)-2-[(6-hydroxy-1,3,4,5-tetrahydro-2H-pyrido[4,3-b]indol-2-yl)carbonyl]cyclohexanecarboxamide

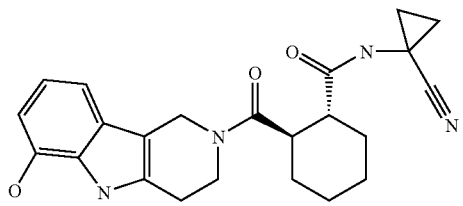

The (1R,2R)-2-(6-Benzyloxy-1,3,4,5-tetrahydro-pyrido[4,3-b]indole-2-carbonyl)-cyclohexanecarboxylic acid (1-cyano-cyclopropyl)-amide in ethyl acetate (15 mL) was hydrogenated over 5% palladium on carbon (10 mg). After an apparent uptake of 5 mL (30 min) the reaction was stopped and a sample taken for LCMS. The catalyst was filtered off and a different batch of catalyst and ethanol (5 mL) were added and the hydrogenation continued. Although there was no further uptake apparent after 3 h the reaction was stopped and LCMS indicated that the reduction had proceeded to the required product. Purified by preparative HPLC (0.5% HCOOH, CH₃CN/H₂O gradient) to give a white powder (34.7 mg, 43%)

MS (+ve ESI): 407 (M+H)⁺

¹H NMR (400.132 MHz, DMSO) δ 0.73-1.07 (m, 2H), 1.10-1.48 (m, 6H), 1.61-1.86 (m, 4H), 2.54-2.58 (m, 1H), 2.64-3.07 (m, 3H), 3.60-3.97 (m, 2H), 4.54 (q, 1H), 4.68 (s, 1H), 6.48 (t, 1H), 6.76 (quintet, 1H), 6.88 (q, 1H), 8.64 (s, 1H), 9.35 (d, 1H), 10.63 (s, 1H).

EXAMPLE 34

(1R,2R)-N-(1-cyanocyclopropyl)-2-[(6-propoxy-1,3,4,5-tetrahydro-2H-pyrido[4,3-b]indol-2-yl)carbonyl]cyclohexanecarboxamide

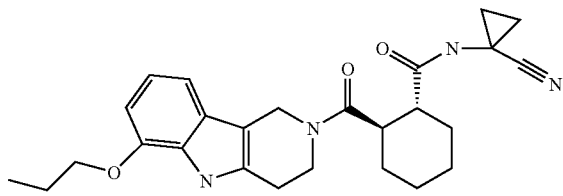

(1R,2R)-2-(6-Hydroxy-1,3,4,5-tetrahydro-pyrido[4,3-b]indole-2-carbonyl)-cyclohexanecarboxylic acid (1-cyano-cyclopropyl)-amide (102 mg, 0.25 mmol), 1-bromopropane (28.0 uL, 0.30 mmol) and potassium carbonate (35.0 mg, 0.25 mmol) in acetone (5 mL) were heated to reflux for 3 h. Added further 1-bromopropane (58.0 uL, 0.60 mmol) and potassium carbonate (70.0 mg, 0.50 mmol) and heated overnight. The reaction darkened significantly and LCMS indicated 60% required product and 40% SM. The reaction was filtered and the liquors evaporated to dryness before redissolving in acetonitrile and purifying by preparative HPLC (0.5% HCOOH, CH₃CN/H₂O gradient) to give a brown glass (21.3 mg, 18%)

MS (+ve ESI): 449 (M+H)⁺

1H NMR (400.132 MHz, DMSO) δ 0.64-1.00 (m, 5H), 1.01-1.34 (m, 6H), 1.47-1.76 (m, 6H), 2.42-2.96 (m, 4H), 3.49-3.84 (m, 2H), 3.94 (t, 2H), 4.43 (q, 1H), 4.58 (s, 1H), 6.49 (t, 1H), 6.70-6.98 (m, 2H), 8.51 (s, 1H), 10.67 (s, 1H).

EXAMPLE 35

(1R,2R)-N-(1-cyanocyclopropyl)-2-{[6-(cyanomethoxy)-1,3,4,5-tetrahydro-2H-pyrido[4,3-b]indol-2-yl]carbonyl}cyclohexanecarboxamide

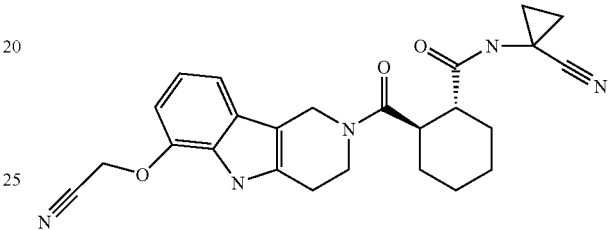

Following Example 34 (1R,2R)-2-(6-hydroxy-1,3,4,5-tetrahydro-pyrido[4,3-b]indole-2-carbonyl)-cyclohexanecarboxylic acid (1-cyano-cyclopropyl)-amide (102 mg, 0.25 mmol), bromoacetonitrile (50 uL, 0.75 mmol) and potassium carbonate (104 mg, 0.75 mmol) in DMF (5 mL) were heated to 80° C. for 1 h when reaction was ca 60% complete. Preparative HPLC (0.5% HCOOH, CH₃CN/H₂O gradient) to give a yellow solid (51.9, 47%).

MS (+ve ESI): 446 (M+H)⁺

¹H NMR (400.132 MHz, DMSO) δ 0.71-1.04 (m, 2H), 1.09-1.47 (m, 6H), 1.59-1.85 (m, 4H), 2.54-2.57 (m, 1H), 2.59-3.28 (m, 3H), 3.62-3.98 (m, 2H), 4.57 (q, 1H), 4.72 (s, 1H), 5.29 (s, 2H), 6.80 (t, 1H), 6.95 (quintet, 1H), 7.18 (q, 1H), 8.70 (s, 1H), 11.14 (s, 1H).

EXAMPLE 36

(1R,2R)-N-(1-cyanocyclopropyl)-2-(6-(2-(dimethylamino)ethoxy)-2,3,4,5-tetrahydro-1H-pyrido[4,3-b]indole-2-carbonyl)cyclohexanecarboxamide

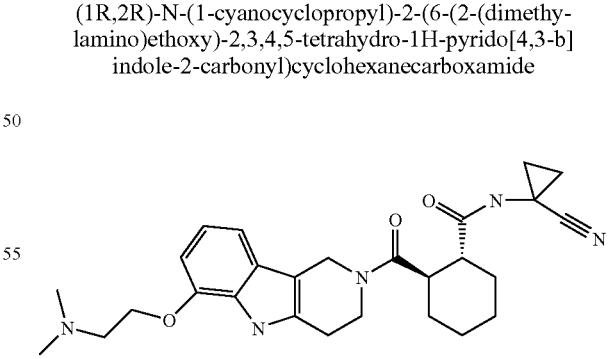

(3aR,7aR)-hexahydroisobenzofuran-1,3-dione (125 mg, 0.81 mmol) was added to N,N-dimethyl-2-(2,3,4,5-tetrahydro-1H-pyrido[4,3-b]indol-6-yloxy)ethanamine (210 mg, 0.81 mmol) in DMF (10 ml) at room temperature under air. The resulting solution was stirred at room temperature for 2 hours. N,N-Diisopropylethylamine (0.535 ml, 3.24 mmol), HATU (462 mg, 1.21 mmol) and 1-amino-1-cyclopropanecarbonitrile HCL (144 mg, 1.21 mmol) were then added to the mixture. The resulting solution was stirred at room temperature for 20 hours. The crude product was purified by preparative HPLC (0.1% NH$_3$, CH$_3$CN/H$_2$O gradient) as eluents to afford as a brown gum (89 mg, 23%).

MS (+ve ESI): 478 (M+H)$^+$ $^1$H NMR (400.13 MHz, CDCl3) δ 0.71-1.52 (4H, m), 1.64-2.00 (8H, m), 2.56-2.60 (1H, m), 2.64 (3H, s), 2.65 (3H, s), 2.91-3.03 (3H, m), 3.11 (2H, t), 3.88-3.90 (1H, m), 4.13 and 4.40 (1H, m), 4.29 (2H, t), 4.73-4.78 (1H, m), 4.78-4.81 (1H, m), 6.53-6.61 (2H, m), 6.93-7.01 (1H, m), 7.09-7.12 (1H, m), 8.59 (1H, s)

N,N-dimethyl-2-(2,3,4,5-tetrahydro-1H-pyrido[4,3-b]indol-6-yloxy)ethanamine was prepared in the following manner.

tert-Butyl 6-(2-(dimethylamino)ethoxy)-3,4-dihydro-1H-pyrido[4,3-b]indole-2(5H)-carboxylate

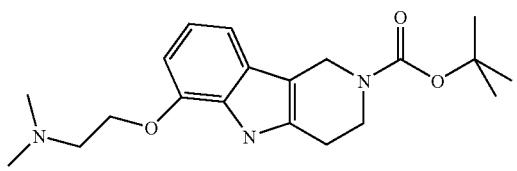

tert-Butyl-6-iodo-3,4-dihydro-1H-pyrido[4,3-b]indole-2(5H)-carboxylate (500 mg, 1.26 mmol), copper(I) iodide (71.7 mg, 0.38 mmol) and tri-potassium orthophosphate (533 mg, 2.51 mmol) were suspended in 2-dimethylaminoethanol (10 ml, 99.40 mmol) and sealed into a microwave tube. The reaction was heated to 150° C. for 1 hour in the microwave reactor and cooled to RT. The reaction mixture was diluted with DCM (100 mL), and washed with 2N NaOH (3×50 mL). The organic layer was dried over Na$_2$SO$_4$, filtered and evaporated to afford crude product. The crude product was purified by preparative HPLC (0.1% NH$_3$, CH$_3$CN/H$_2$O gradient) to afford tert-butyl 6-(2-(dimethylamino)ethoxy)-3,4-dihydro-1H-pyrido[4,3-b]indole-2(5H)-carboxylate (304 mg, 67%) as a yellow gum.

MS (+ve ESI): 360 (M+H)$^+$

N,N-dimethyl-2-(2,3,4,5-tetrahydro-1H-pyrido[4,3-b]indol-6-yloxy)ethanamine

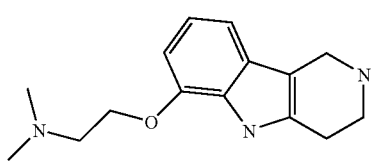

tert-Butyl 6-(2-(dimethylamino)ethoxy)-3,4-dihydro-1H-pyrido[4,3-b]indole-2(5H)-carboxylate (304 mg, 0.85 mmol) was added to methanolic HCl (20 ml, reagent 10) at 0° C. under air. The resulting solution was stirred at room temperature for 19 hours. The solvent was removed under reduced pressure to afford N,N-dimethyl-2-(2,3,4,5-tetrahydro-1H-pyrido[4,3-b]indol-6-yloxy)ethanamine (205 mg, 93%) as a yellow solid.

EXAMPLE 37

(1R,2R)-N-(1-cyanocyclopropyl)-2-(6-(2-morpholinoethoxy)-2,3,4,5-tetrahydro-1H-pyrido[4,3-b]indole-2-carbonyl)cyclohexanecarboxamide

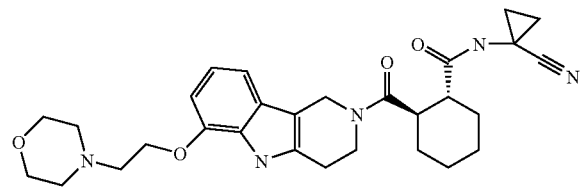

Following on from Example 34, 4-(2-Chloroethyl)morpholine hydrochloride (90 mg, 0.48 mmol) was added to (1R,2R)-N-(1-cyanocyclopropyl)-2-(6-hydroxy-2,3,4,5-tetrahydro-1H-pyrido[4,3-b]indole-2-carbonyl)cyclohexanecarboxamide (131 mg, 0.32 mmol) and potassium carbonate (134 mg, 0.97 mmol) in DMF (5 ml) at 25° C. under air. The resulting solution was stirred at room temperature for 45 hours, to yield after purification a cream solid. (4.00 mg, 2.4%).

MS (+ve ESI): 520 (M+H)$^+$ $^1$H NMR (400.13 MHz, CDCl3) δ 1.05-1.75 (8H, m), 1.83-1.90 (4H, m), 2.61 (4H, t), 2.79-2.84 (2H, m), 2.82 (2H, t), 2.97-2.98 (2H, m), 3.40 and 4.38 (1H, 2×m), 3.61-3.92 (1H, m), 3.75-3.78 (4H, m), 4.24-4.27 (2H, m), 4.73-4.78 (2H, m), 6.42 and 6.53 (1H, 2×s), 6.66 (1H, t), 6.96-7.03 (1H, m), 7.08-7.12 (1H, m), 9.13 (1H, m)

EXAMPLE 38

(1R,2R)-N-(1-cyanocyclopropyl)-2-(6-(2-(pyrrolidin-1-yl)ethoxy)-2,3,4,5-tetrahydro-1H-pyrido[4,3-b]indole-2-carbonyl)cyclohexanecarboxamide

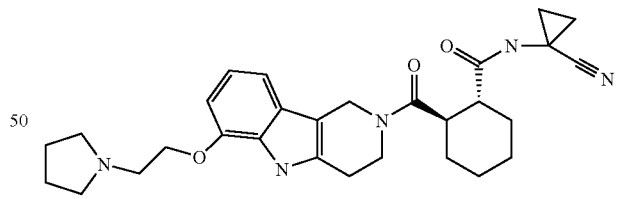

Following on from Example 34, 1-(2-chloroethyl)pyrrolidine hydrochloride (82.0 mg, 0.48 mmol) was added to (1R, 2R)-N-(1-cyanocyclopropyl)-2-(6-hydroxy-2,3,4,5-tetrahydro-1H-pyrido[4,3-b]indole-2-carbonyl)cyclohexanecarboxamide (131 mg, 0.32 mmol) and potassium carbonate (134 mg, 0.97 mmol) in DMF (5 mL) at 25° C. under air. The resulting solution was stirred at room temperature for 45 hours, to yield after purification a cream solid. (6.00 mg, 3.7%).

MS (+ve ESI) 504 (M+H)$^+$ $^1$H NMR (400.13 MHz, CDCl3) δ 1.27-1.88 (13H, m), 1.90-1.92 (2H, m), 2.01-2.05 (1H, m), 2.38 (1H, t) 2.59 (1H, t), 2.71-2.82 (4H, m), 2.86-3.04 (4H, m), 3.85 and 4.41 (1H, 2×m), 3.87-3.89 (1H, m), 4.26 (2H, t), 4.73-4.77 (2H, m), 6.51 and 6.59 (1H, 2×s), 6.64 (1H, t), 6.94-7.01 (1H, m), 7.08-7.11 (1H, m), 10.03 (1H, m).

EXAMPLE 39

(1R,2R)-N-(1-cyanocyclopropyl)-2-(6-(2-(piperidin-1-yl)ethoxy)-2,3,4,5-tetrahydro-1H-pyrido[4,3-b]indole-2-carbonyl)cyclohexanecarboxamide

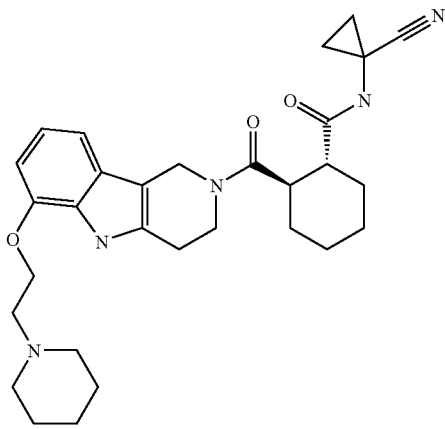

Following on from Example 24, but starting with 6-(2-(piperidin-1-yl)ethoxy)-2,3,4,5-tetrahydro-1H-pyrido[4,3-b]indole (1.00 g, 3.34 mmol) furnished the desired compound as a white solid (356 mg, 21% yield)

MS (+ve ESI): 518 (M+H)+

$^1$H NMR (400.13 MHz, CDCl3) δ 0.86-1.21 (2H, m), 1.27-1.51 (6H, m), 1.64-1.68 (5H, m), 1.72-1.89 (4H, m), 2.63-2.67 (8H, m), 2.70-3.05 (3H, d), 3.55 and 4.45 (2×1H, m), 3.86-3.92 (1H, m), 4.24 (2H, t), 4.70-4.91 (2H, m), 6.66-6.75 (2H, m), 6.95-7.03 (1H, m), 7.12 (1H, t), 9.90-9.96 (1H, m)

6-(2-(Piperidin-1-yl)ethoxy)-2,3,4,5-tetrahydro-1H-pyrido[4,3-b]indole was prepared in the following manner.

tert-Butyl 6-(2-(piperidin-1-yl)ethoxy)-3,4-dihydro-1H-pyrido[4,3-b]indole-2(5H)-carboxylate

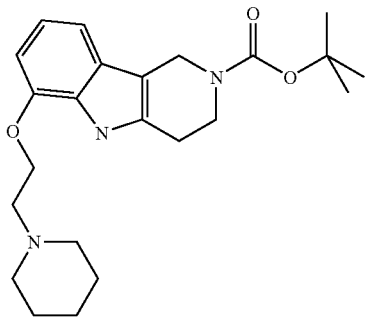

Tri-potassium orthophosphate (1.92 g, 9.04 mmol), tert-butyl 6-iodo-3,4-dihydro-1H-pyrido[4,3-b]indole-2(5H)-carboxylate (1.80 g, 4.52 mmol) and copper(I) iodide (0.430 g, 2.26 mmol) were suspended in 2-(piperidin-1-yl)ethanol (15 ml, large excess) and sealed into a microwave tube after bubbling argon through the solution for 5 minutes. The reaction was heated to 150° C. for 1.5 hours in the microwave reactor and cooled to RT. This reaction was repeat three times and the combined crude reaction mixture worked as follows.

The mixture was diluted with DCM (50 mL) and washed with NaOH (3×30 mL), dried over sodium sulfate and the solvent removed under reduced pressure. The crude product was purified by preparative HPLC (0.1% HCOOH, CH$_3$CN, H$_2$0). Fractions containing the desired compound were evaporated to dryness to afford tert-butyl 6-(2-(piperidin-1-yl)ethoxy)-3,4-dihydro-1H-pyrido[4,3-b]indole-2(5H)-carboxylate (1.33 g, 25% yield) as a yellow gum.

LCMS retention time 1.60 min MS (+ve ESI): 400 (M+H)+

6-(2-(Piperidin-1-yl)ethoxy)-2,3,4,5-tetrahydro-1H-pyrido[4,3-b]indole

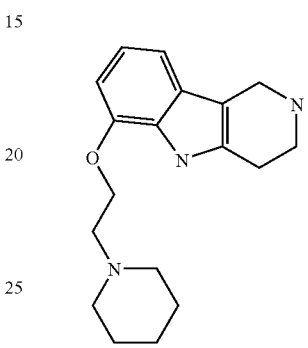

tert-Butyl 6-(2-(piperidin-1-yl)ethoxy)-3,4-dihydro-1H-pyrido[4,3-b]indole-2(5H)-carboxylate (1.33 g, 3.32 mmol) was added to HCl in MeOH (reagent 10, 25 ml) at 25° C. under air. The resulting solution was stirred at room temperature for 3 days. The solvent was removed under reduced pressure to afford (1.00 g, 100%) as a yellow gum. Material was used crude.

LCMS retention time 2.17 min MS (+ve ESI): 300 (M+H)+

EXAMPLE 40

(1R,2R)-N-(1-cyanocyclopropyl)-2-[(5-methanesulphonyl-1,3,4,5-tetrahydro-2H-pyrido[4,3-b]indol-2-yl)carbonyl]cyclohexanecarboxamide

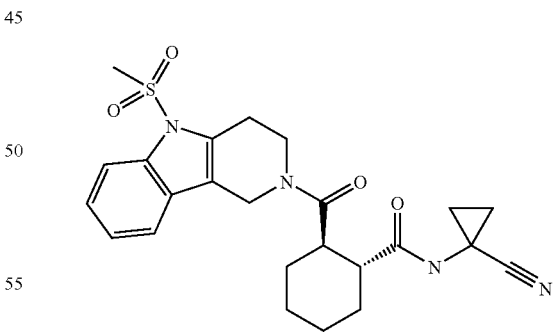

Following Example 24, but starting with 5-methanesulphonyl-2,3,4,5-tetrahydro-1H-pyrido[4,3-b]indole hydrochloride (130 mg, 0.52 mmol) furnished the desired compound as a light brown coloured solid (37 mg, 16%).

MS (+ve ESI): 469 (M+H)+

$^1$H NMR (400 MHz, DMSO) δ 0.8-1.1 (m, 2H), 1.3 (m, 6H), 1.75 (m, 4H), 2.4 (m, 1H), 2.9-3.3 (m, 3H), 3.35 (s, 3H), 3.9 (m, 2H), 4.5-4.8 (m, 2H), 7.3 (m, 2H), 7.65 (m, 1H), 7.9 (d, 1H), 8.7 (s, 1H).

5-Methanesulphonyl-2,3,4,5-tetrahydro-1H-pyrido[4,3-b]indole hydrochloride was prepared in the following manner.

N-Boc-2,3,4,5-tetrahydro-1H-pyrido[4,3-b]indole

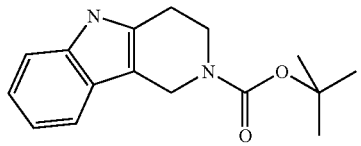

2,3,4,5-Tetrahydro-1H-pyrido[4,3-b]indole hydrochloride (3.64 g, 17.4 mmol) was suspended in dichloromethane (120 mL) and stirred at room temperature under argon. Triethylamine (7.29 mL, 52.3 mmol) was added followed by di-tert-butyl dicarbonate (3.81 g, 17.4 mmol) in DCM (30 mL) and the resulting solution stirred overnight with the argon source removed. DCM was removed in vacuo and the residue partitioned between brine (50 mL) and ethyl acetate (2×100 mL). Combined organics were dried (sodium sulphate) and concentrated in vacuo to give N-boc-2,3,4,5-tetrahydro-1H-pyrido[4,3-b]indole as a pale yellow solid (4.23 g, 89%).

MS (+ve ESI): 271 (M+H)+

$^1$H NMR (400 MHz, DMSO) δ 1.45 (s, 9H), 2.8 (t, 2H), 3.7 (t, 2H), 4.55 (s, 2H), 6.95 (t, 1H), 7.05 (t, 1H), 7.3 (d, 1H), 7.4 (d, 1H), 10.85 (s, 1H).

5-Methanesulphonyl-2,3,4,5-tetrahydro-1H-pyrido[4,3-b]indole

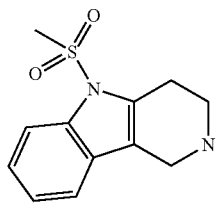

N-Boc-2,3,4,5-tetrahydro-1H-pyrido[4,3-b]indole (800 mg, 2.94 mmol) was dissolved in DMF (20 mL) and stirred at room temperature. The vessel was flushed with argon and sodium hydride (235 mg, 5.87 mmol) was added. After 30 minutes, the reaction was cooled to 0° C. and methanesulphonyl chloride (0.46 mL, 5.87 mmol) was added dropwise over 5 minutes. The mixture was stirred and allowed to warm to room temperature overnight and the solvent removed in vacuo. TLC and LCMS showed that the BOC group was removed during this process. Therefore the residue was partitioned between 2M aqueous sodium hydroxide (30 mL) and dichloromethane (2×100 mL) and combined organics treated with brine (30 mL), dried (sodium sulphate), concentrated in vacuo. Flash column chromatography (silica, eluting with 100% dichloromethane/5% methanolic ammonia in 50% ethanol/dichloromethane) gave 5-methanesulphonyl-2,3,4,5-tetrahydro-1H-pyrido[4,3-b]indole as a pale yellow brittle solid (135 mg, 18%).

MS (+ve ESI): 251 (M+H)+

$^1$H NMR (400 MHz, DMSO) δ 2.85 (t, 2H), 3.1 (t, 2H), 3.35 (s, 3H), 3.9 (s, 2H), 7.25 (m, 2H), 7.5 (d, 1H), 7.9 (d, 1H).

EXAMPLE 41

(1R,2R)-2-(7,8-Dihydro-5H-furo[2,3-b:4,5-c']dipyridine-6-carbonyl)-cyclohexanecarboxylic acid (1-cyano-cyclopropyl)-amide

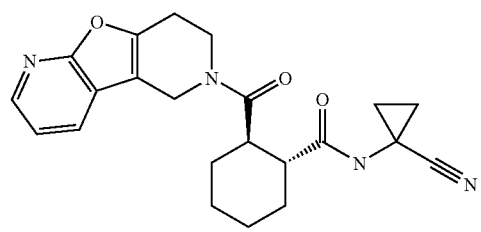

Following Example 24, but starting with 1,5,6,7,8,9a-hexahydro-furo[2,3-b:4,5-c']dipyridine (209 mg, 1.20 mmol) furnished the desired compound as a light brown coloured solid (44.0 mg, 9.3%).

MS (+ve ESI): 393 (M+H)+

$^1$H NMR (500.13 MHz, DMSO-d6) δ 0.93 (2H, d), 1.26-1.43 (6H, m), 1.73-1.86 (4H, m), 2.52-2.56 (2H, m), 2.90 (1H, obs), 3.00-3.07 (1H, m), 3.89-3.98 (2H, m), 4.66-4.71 (2H, m), 7.29-7.32 (1H, m), 8.03 (1H, d), 8.22-8.23 (1H, m), 8.29 (1H, s)

1,5,6,7,8,9a-Hexahydro-furo[2,3-b:4,5-c']dipyridine was prepared in the following manner.

tert-Butyl 4-oxo-3-(2-oxo-1,2-dihydropyridin-3-yl)piperidine-1-carboxylate

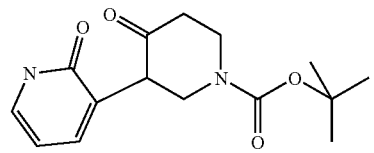

Potassium tert-butoxide (1.22 g, 10.8 mmol) were added to tert-butyl 4-(hydroxyimino)piperidine-1-carboxylate (2.11 g, 9.85 mmol) in DMF (10 mL) at 0° C. under argon. The resulting suspension was stirred for 20 mins. 2-Fluoropyridine (0.85 mL, 9.85 mmol) was added to the reaction mixture and the resulting solution was stirred at 80° C. for 21 hours. The reaction mixture was poured into ice water (100 mL) and extracted with EtOAc (2×50 mL). The organic layers were combined and washed with brine (2×50 mL). The organic layer was dried over Na$_2$SO$_4$, filtered and evaporated to afford crude product. Flash column chromatography (silica, gradient 5 to 100% EtOAc in isohexane) yielded tert-butyl 4-oxo-3-(2-oxo-1,2-dihydropyridin-3-yl)piperidine-1-carboxylate (0.654 g, 23%) as a cream solid.

MS (+ve ESI): 293 (M+H)+

$^1$H NMR (400.13 MHz, CDCl3) δ 1.50 (9H, s), 2.64 (2H, s), 3.41 (1H, s), 3.48 (2H, t), 3.73 (1H, s), 4.26 (2H, s), 6.26 (1H, t), 7.24-7.27 (1H, m), 7.30-7.32 (1H, m)

1,5,6,7,8,9a-Hexahydro-furo[2,3-b:4,5-c']dipyridine

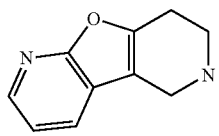

Concentrated Sulfuric acid (1.0 mL, 18.8 mmol) was added to tert-butyl 4-oxo-3-(2-oxo-1,2-dihydropyridin-3-yl)piperidine-1-carboxylate (350 mg, 1.20 mmol). The resulting thick solution was stirred at room temperature overnight. The reaction was heated at 60° C. until reaction complete by LCMS. The reaction was diluted with 90% Acetonitrile 10% Water and solid potassium carbonate was added cautiously to neutral pH (Effervescence), the slurry was filtered and the filtrate evaporated, the resulting residue was used without further purification.

MS (+ve ESI): 175 (M+H)+

EXAMPLE 42

(1R,2R)-2-(7-Methanesulfonyl-1,3,4,5-tetrahydro-pyrido[4,3-b]indole-2-carbonyl)-cyclohexanecarboxylic acid (1-cyano-cyclopropyl)-amide

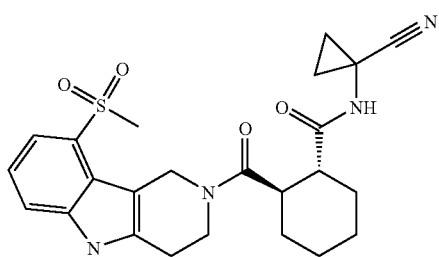

EXAMPLE 43

(1R,2R)-2-(9-Methanesulfonyl-1,3,4,5-tetrahydro-pyrido[4,3-b]indole-2-carbonyl)-cyclohexanecarboxylic acid (1-cyano-cyclopropyl)-amide

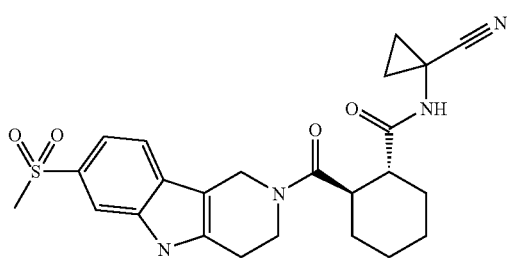

Following on from Example 23, 9-methanesulfonyl-2,3,4,5-tetrahydro-1H-pyrido[4,3-b]indole and 7-methanesulfonyl-2,3,4,5-tetrahydro-1H-pyrido[4,3-b]indole 1:1 mixture (220 mg, 0.88 mmol). The two products were isolated by chiral HPLC (Solvent A=0.1% NH3/Water, Solvent B=CH3CN) (1R,2R)-2-(7-Methanesulfonyl-1,3,4,5-tetrahydro-pyrido[4,3-b]indole-2-carbonyl)-cyclohexanecarboxylic acid (1-cyano-cyclopropyl)-amide as a white solid (65.0 mg, 14%), and (1R,2R)-2-(9-Methanesulfonyl-1,3,4,5-tetrahydro-pyrido[4,3-b]indole-2-carbonyl)-cyclohexanecarboxylic acid (1-cyano-cyclopropyl)-amide as a white solid (56.0 mg, 12%).

EXAMPLE 42

LCMS retention time 1.71 min (+ve ESI): 469 (M+H)+

EXAMPLE 43

LCMS retention time 1.70 (+ve ESI): 469 (M+H)+

The mixture of 9-methanesulfonyl-2,3,4,5-tetrahydro-1H-pyrido[4,3-b]indole and 7-methanesulfonyl-2,3,4,5-tetrahydro-1H-pyrido[4,3-b]indole was prepared in the following manner.

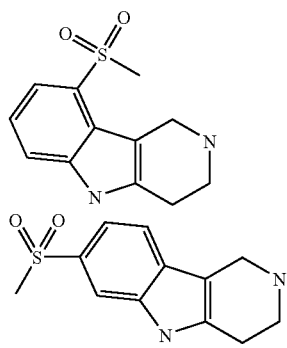

(3-Methanesulfonyl-phenyl)-hydrazine (605 mg, 3.25 mmol) and 4-piperidone hydrochloride (443 mg, 3.25 mmol) were suspended in acetic acid (15 mL) and stirred at room temperature under argon. Boron trifluoride diethyl etherate (0.80 mL, 6.51 mmol) was added in one portion and the yellow suspension stirred at 110° C. for 2 hours resulting in a deep red solution. It was cooled to room temperature and acetic acid removed in vacuo. The residue was partitioned between 2N aqueous sodium hydroxide (30 mL) and dichloromethane (2×100 mL). Combined organics were dried (Na2SO4), concentrated in vacuo. Flash column chromatography (silica, 100% dichloromethane gradiant to 5% aq ammonia in 50% ethanol/dichloromethane) gave the products as a 1:1 mixture (480 mg, 60%).

LCMS retention time 1.34 min (+ve ESI): 251 (M+H)+

EXAMPLE 44

(1R,2R)-N-(1-cyanocyclopropyl)-2-(2,2-difluoro-7,8,9,10-tetrahydro-6H-[1,3]dioxolo[4,5-g]pyrido[4,3-b]indole-7-carbonyl)cyclohexanecarboxamide

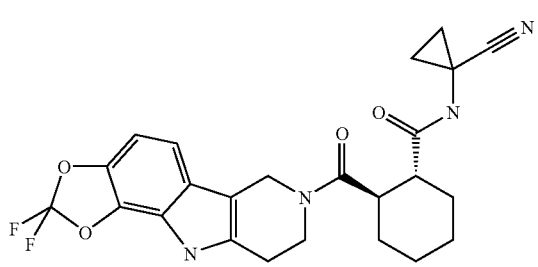

Following on from Example 24, except using 2,2-difluoro-7,8,9,10-tetrahydro-6H-[1,3]dioxolo[4,5-g]pyrido[4,3-b]indole (147 mg, 0.58 mmol) gave the product after purification (1R,2R)-N-(1-cyanocyclopropyl)-2-(2,2-difluoro-7,8,9,10-tetrahydro-6H-[1,3]dioxolo[4,5-g]pyrido[4,3-b]indole-7-carbonyl)cyclohexanecarboxamide (58.0 mg, 21%) as a beige solid.

MS (+ve ESI): 175 (M+H)+

1H NMR (400.132 MHz, DMSO) δ 0.70-1.07 (m, 2H), 1.10-1.56 (m, 6H), 1.55-1.87 (m, 4H), 2.61-3.15 (m, 4H), 3.66-3.96 (m, 2H), 4.58 (q, J=23.0 Hz, 1H), 4.74 (s, 1H), 6.98-7.39 (m, 2H), 8.65 (s, 1H), 11.52 (s, 1H)

2,2-Difluoro-7,8,9,10-tetrahydro-6H-[1,3]dioxolo[4,5-g]pyrido[4,3-b]indole was prepared in the following manner (2,2-Difluoro-1,3-benzodioxol-4-yl)hydrazine

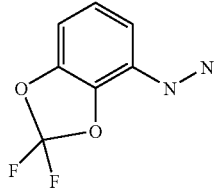

The 2,2-Difluoro-benzo[1,3]dioxol-4-ylamine (1.99 g, 11.5 mmol) was cooled and cone hydrochloric acid (10 mL) added. After recooling to 0° C. or less a solution of the sodium nitrite (873 mg, 12.7 mmol) in water (10 mL) was added dropwise. The reaction was stirred at the same temp for 30 min when tin chloride (6.55 g, 34.5 mmol) in hydrochloric acid (10 mL) was added dropwise again keeping temp ea 0° C. (nb initial additions of SnCl₂ were very exothermic and the initial thick ppt required a large stirrer to keep things moving). The reaction was stored in the fridge overnight at 0° C. The resulting solid was filtered off, washed with sat NaCl (50 mL) and then ether:hexane 1:2 (50 mL) before drying to give a white solid. The solid was treated with 50% aqueous sodium hydroxide (100 mL) and extracted with ether (3×50 mL). The combined extracts were dried and filtered to give a yellow oil which crystallised to long needles on standing (1.28 g, 60%).

MS (+ve ESI): 205 (M+H)+

¹H NMR (400.132 MHz, DMSO) δ 4.15 (s, 2H), 6.57 (d, 1H), 6.89 (d, 1H), 6.99 (t, 1H), 7.07 (s, 1H)

2,2-Difluoro-7,8,9,10-tetrahydro-6H-[1,3]dioxolo[4,5-g]pyrido[4,3-b]indole

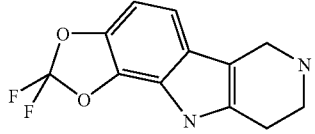

The (2,2-difluoro-benzo[1,3]dioxol-4-yl)-hydrazine (753 mg, 4.00 mmol) and 4-piperidone hydrochloride (543 mg, 4.00 mmol) in ethanol (10 mL) were heated to reflux for 45 min. The 4M HCl in dioxane (2 mL) was added and heating continued for 2 h. A sample was removed and after bubbling HCl gas briefly was heated in the microwave to 110° C. for 10 min. The rest of the material was processed in 5 batches and the combined black reactions filtered, washed with a little water and then precipitation with Et₂O:Hexane 1:2 (c.f. 10 mL) before drying the resulting grey solid (147 mg, 13% yield)

MS (+ve ESI): 253 (M+H)+

¹H NMR (400.132 MHz, DMSO) δ 3.04 (s, 1H), 3.26-3.54 (m, 5H), 4.30 (s, 1H), 7.07-7.40 (m, 2H).

EXAMPLE 45

(1R,2R)-N-(1-cyanocyclopropyl)-2-(8-fluoro-6-methoxy-2,3,4,5-tetrahydro-1H-pyrido[4,3-b]indole-2-carbonyl)cyclohexanecarboxamide

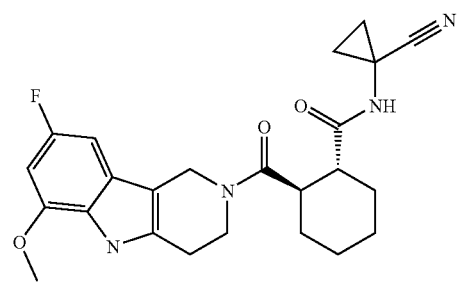

Following on from Example 24, except using 8-fluoro-6-methoxy-2,3,4,5-tetrahydro-1H-pyrido[4,3-b]indole (20.0 mg, 0.09 mmol), yielded the title compound as a white foam (31.6 mg, 79%).

MS (+ve ESI): 439.4 (M+H)+

¹H NMR (400.13 MHz, CDCl3) δ 0.83-0.89 (0.5H, m), 0.98-1.50 (6H, m), 1.62 1.90 (5H, m), 2.56-2.62 (1H, m), 2.75-2.98 (3H, m), 3.62-3.90 (2H, m), 3.92 (3H, d), 4.29-4.35 (0.5H, m), 4.60-4.85 (2H, m), 6.37-6.47 (2H, m), 6.69-6.75 (1H, m), 7.99 (1H, s)

8-Fluoro-6-methoxy-2,3,4,5-tetrahydro-1H-pyrido[4,3-b]indole was prepared in the following manner Diphenylmethanone (4-fluoro-2-methoxyphenyl)hydrazone

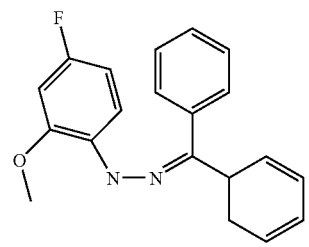

A mixture of 2-chloro-5-fluoroanisole (0.52 ml, 4.10 mmol), benzophenone hydrazone (0.98 g, 5.00 mmol), sodium-tert-butoxide (561 mg, 5.80 mmol), in toluene (8.0 ml) was charged with Pd₂(dba)₃ (77.0 mg, 0.08 mmol) and 2-(di-t-butylphosphino)biphenyl (50.0 mg, 0.17 mmol) and heated to 80° C. under argon. The mixture was stirred overnight and checked with LCMS and TLC. The mixture was allowed to cool to room temperature and the reaction mixture was diluted with EtOAc (20 ml) and filtered. Material was used crude in the next step.

8-Fluoro-6-methoxy-2,3,4,5-tetrahydro-1H-pyrido[4,3-b]indole

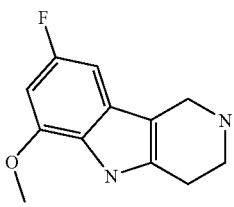

p-Toluenesulfonic acid (129 mg, 0.75 mmol) was added to piperidin-4-one hydrochloride (50.8 mg, 0.37 mmol) and 1-(diphenylmethylene)-2-(4-fluoro-2-methoxyphenyl)hydrazine (80.0 mg, 0.25 mmol) in ethanol (1.25 mL) at 25° C. over a period of 1 min under air. The resulting suspension was stirred at 80° C. for 16 hours. The reaction mixture was diluted with EtOH (20 mL), and EtOAC (100 mL) then washed sequentially with saturated NaHCO₃ (75 mL), saturated NaHCO₃ (75 mL), and saturated brine (75 mL). The organic layer was dried over Na₂SO₄, filtered and evaporated to afford crude product. The crude product was purified by ion exchange chromatography, using an SCX column. The desired product was eluted from the column using 7M NH₃/MeOH and pure fractions were evaporated to dryness to afford crude product. The crude product was purified by preparative HPLC (containing 0.1% NH₃, CH₃CN/H₂O) as eluents. Fractions containing the desired compound were evaporated to dryness to afford 8-fluoro-6-methoxy-2,3,4,5-tetrahydro-1H-pyrido[4,3-b]indole (25.0 mg, 46%) as an off-white solid.

MS (+ve ESI): 221.3 (M+H)+

¹H NMR (400.13 MHz, CDCl3) δ 1.63 (1H, bs), 2.75 (2H, t), 3.21 (2H, t), 3.92 (3H, s), 3.99 (2H, t), 6.39-6.42 (1H, m), 6.67-6.70 (1H, m), 7.99 (1H, s)

Assay for Identification of Cathepsin K Inhibitors

QFRET Technology (Quenched Fluorescent Resonance Energy Transfer) was used to measure the inhibition by test compounds of cathepsin K-mediated cleavage of the synthetic peptide Z-Phe-Arg-AMC. Compounds were screened at twelve concentrations (3.5×10-8-10 uM), on two separate occasions and the mean pIC50 values reported.

0.5 nM [final] rhuman cathepsin K in phosphate buffer was added to a 384-well black microtitre plate containing investigative compounds. The enzyme and compound were pre-incubated at room temperature for 30 minutes before the addition of 50 mM [final] Z-Phe-Arg-AMC synthetic substrate in phosphate buffer. The plates were covered and incubated for 1 h at room temperature, protected from light. Following the incubation the reaction was stopped with 7.5% [final]acetic acid. Relative fluorescence was measured using the Ultra plate reader at a wavelength of 360 nm excitation and 425 nm emission.

Data was corrected for background fluorescence (minimum controls without enzyme). This data was used to plot inhibition curves and calculate pIC50 values by non-linear regression using a variable slope, offset=zero model in Origin 7.5 analysis package. Reproducibility of data was assessed using a quality control statistical analysis package whereby internal variability of the assayed indicated a repeat testing (n=3) if pIC50 SD was >0.345.

The compounds of the Examples have Cat K FRET competitive binding as measured by the assay described above each with a pIC50>6.5. The individual values are set out below.

| Example No | CatK FRET Mean pIC50 |
|---|---|
| 1 | 9.071 |
| 2 | 8.524 |
| 3 | 9.115 |
| 4 | 8.887 |
| 5 | 8.195 |
| 6 | 8.553 |
| 7 | 7.376 |
| 8 | 7.39 |
| 9 | 7.302 |
| 10 | 7.991 |
| 11 | 8.435 |
| 12 | 8.547 |
| 13 | 8.649 |
| 14 | 8.969 |
| 15 | 8.05 |
| 16 | 7.105 |
| 17 | 9.182 |
| 18 | 8.149 |
| 19 | 8.75 |
| 20 | 8.718 |
| 21 | 8.835 |
| 22 | 8.365 |
| 23 | 8.649 |
| 24 | 8.725 |
| 25 | 9.046 |
| 26 | 8.545 |
| 27 | NA |
| 28 | 8.462 |
| 29 | 8.41 |
| 30 | 8.26 |
| 31 | 7.759 |
| 32 | 8.999 |
| 33 | 8.989 |
| 34 | 9.313 |
| 35 | 9.253 |
| 36 | 9.489 |
| 37 | 8.495 |
| 38 | 8.785 |
| 39 | 9.138 |
| 40 | 7.965 |
| 41 | 8.191 |
| 42 | 6.903 |
| 43 | 7.141 |
| 44 | 8.671 |
| 45 | 9.093 |

The invention claimed is:

1. A compound of formula (I)

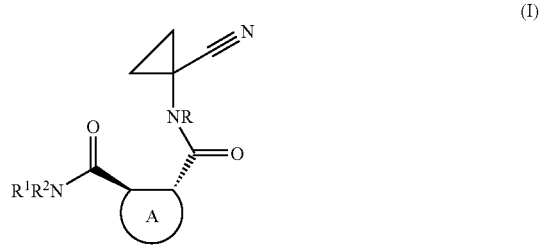

in which:
A is a cyclohexane ring;
R is hydrogen;
R¹ and R² together with the nitrogen atom to which they are attached form a 5- to 7-membered monocyclic saturated or partially unsaturated heterocyclic ring, which ring shares at least one atom with a second monocyclic saturated, partially unsaturated or unsaturated ring so as to form a bicyclic ring system;

which bicyclic ring system shares at least one atom with a third saturated, partially unsaturated or unsaturated ring so as to form a tricyclic ring system comprising up to 19 ring atoms,
and wherein the tricyclic ring system optionally comprise up to five heteroatoms each independently selected from O, S or N atoms, and is optionally substituted by up to three substituents each independently selected from phenyl, benzyl, naphthyl, $C_{1-6}$ alkyl, $C_{2-6}$alkenyl, $C_{2-6}$alkynyl, cyano, halogen, $COOR^3$, $COR^3$, $NO_2$, $OR^3$, $CONR^4R^5$, $NR^4R^5$, $C_{1-2}$alkanesulfonyl-, monocyclic heteroaryl comprising up to 7 ring atoms, and bicyclic heteroaryl comprising up to 12 carbon atoms,
and the tricyclic ring system is optionally substituted on adjacent carbon atoms by a group —O—$C(R^8)_2$—O—, wherein each $R^8$ is hydrogen or a halogen atom, so as to form a 1,3-dioxolo group,
and wherein (i) phenyl, naphthyl, $C_{1-6}$ alkyl, $C_{2-6}$alkenyl, $C_{2-6}$alkynyl and benzyl are optionally further substituted by up to three substituents each independently selected from halogen, $NR^4R^5$, $SO_2R^3$, $CONR^4R^5$, cyano, $OR^3$, $SO_2NR^4R^5$, $NSO_2R^3$, $NR^4COR^5$, and $C_{1-6}$ alkyl itself optionally substituted with up to three substituents independently selected from halogen, cyano, $SO_2R^3$, $NR^4R^5$, $OR^3$, $SO_2NR^4R^5$, $NSO_2R^3$, $NR^4COR^5$ and $CONR^4R^5$,
and (ii) monocyclic or bicyclic heteroaryl are optionally further substituted by up to three substituents each independently selected from halogen, $NR^4R^5$, $SO_2NR^4R^5$, $NSO_2R^3$, $NR^4COR^5$, $CONR^4R^5$, $SO_2R^3$, cyano, $OR^3$, and phenyl itself optionally substituted with up to three halogen groups, $SO_2R^3$, or $C_{1-6}$ alkyl itself optionally substituted with up to three substituents independently selected from halogen, cyano, $SO_2R^3$, $SO_2NR^4R^5$, $NSO_2R^3$, $NR^4COR^5$, $NR^4R^5$, $OR^3$, $C_{3-7}$-carbocyclyl and $CONR^4R^5$;

$R^3$ is selected from hydrogen, $C_{1-6}$ alkyl, $C_{3-7}$carbocyclyl, phenyl, monocyclic heteroaryl, a 4-7 membered monocyclic saturated heterocyclic ring comprising up to three heteroatoms each independently selected from O, S or N atoms, and wherein $C_{1-6}$ alkyl and phenyl and monocyclic heteroaryl can each be optionally substituted by up to three groups independently selected from halogen, cyano, $CONR^4R^5$, $NR^4R^5$, $SO_2NR^4R^5$, $NSO_2R^3$ and $SO_2R^3$;

$R^4$ and $R^5$ are independently hydrogen, $C_{1-6}$ alkyl, $COR^3$, monocyclic heteroaryl comprising up to 7 ring atoms or bicyclic heteroaryl comprising up to 12 ring atoms or together with the nitrogen to which they are attached form a 5- to 7-membered monocyclic saturated heterocyclic ring optionally comprising up to three additional heteroatoms each independently selected from O, S or N atoms and optionally substituted by $C_{1-6}$ alkyl optionally substituted by $NR^6R^7$;

$R^6$ and $R^7$ are independently hydrogen, $C_{1-6}$ alkyl, or together with the nitrogen to which they are attached form a 5- to 7-membered monocyclic saturated heterocyclic ring optionally comprising up to three additional heteroatoms each independently selected from O, S or N atoms;

or a pharmaceutically acceptable salt thereof.

2. The compound or salt according to claim 1, wherein $R^1$ and $R^2$ together with the nitrogen atom to which they are attached form a 5- to 6-membered monocyclic saturated or partially saturated heterocyclic ring, which ring shares two atoms with a second saturated or unsaturated ring so as to form a bicyclic ring system, which bicyclic ring system shares one or two atoms with a third saturated or unsaturated ring so as to form a tricyclic ring system containing a total of up to 15 ring atoms, wherein the tricyclic ring system can optionally contain up to three heteroatoms each independently selected from O, S or N atoms and can optionally be substituted by up to three substituents as defined in claim 1.

3. The compound or salt according to claim 2 and wherein the second ring is a 5-6 membered unsaturated ring comprising one heteroatom selected from N and O, and the third ring is a 6-membered ring optionally comprising one heteroatom selected from N.

4. The compound or salt as claimed in claim 1, wherein the compound is selected from any one of:
- (1R,2R)—N-(1-cyanocyclopropyl)-2-[(8-fluoro-1,3,4,5-tetrahydro-2H-pyrido[4,3-b]indol-2-yl)carbonyl]cyclohexanecarboxamide;
- (1R,2R)-2-[(8-chloro-1,3,4,5-tetrahydro-2H-pyrido[4,3-b]indol-2-yl)carbonyl]-N-(1-cyanocyclopropyl)cyclohexanecarboxamide;
- (1R,2R)—N-(1-cyanocyclopropyl)-2-[(6-fluoro-1,3,4,5-tetrahydro-2H-pyrido[4,3-b]indol-2-yl)carbonyl]cyclohexanecarboxamide;
- (1R,2R)—N-(1-cyanocyclopropyl)-2-(1,3,4,5-tetrahydro-2H-pyrido[4,3-b]indol-2-ylcarbonyl)cyclohexanecarboxamide;
- (1R,2R)-2-[(8-bromo-1,3,4,5-tetrahydro-2H-pyrido[4,3-b]indol-2-yl)carbonyl]-N-(1-cyanocyclopropyl)cyclohexanecarboxamide;
- (1R,2R)—N-(1-cyanocyclopropyl)-2-[(6-methyl-1,3,4,5-tetrahydro-2H-pyrido[4,3-b]indol-2-yl)carbonyl]cyclohexanecarboxamide;
- (1R,2R)—N-(1-cyanocyclopropyl)-2-[8-(trifluoromethyl)-1,3,4,5-tetrahydro-2H-pyrido[4,3-b]indol-2-yl]carbonyl}cyclohexanecarboxamide;
- (1R,2R)—N-(1-cyanocyclopropyl)-2-[(8-methoxy-1,3,4,5-tetrahydro-2H-pyrido[4,3-b]indol-2-yl)carbonyl]cyclohexanecarboxamide;
- (1R,2R)—N-(1-cyanocyclopropyl)-2-[(8-isopropyl-1,3,4,5-tetrahydro-2H-pyrido[4,3-b]indol-2-yl)carbonyl]cyclohexanecarboxamide;
- (1R,2R)—N-(1-cyanocyclopropyl)-2-[(9-fluoro-1,3,4,5-tetrahydro-2H-pyrido[4,3-b]indol-2-yl)carbonyl]cyclohexanecarboxamide;
- (1R,2R)—N-(1-cyanocyclopropyl)-2-[(7-fluoro-1,3,4,5-tetrahydro-2H-pyrido[4,3-b]indol-2-yl)carbonyl]cyclohexanecarboxamide;
- (1R,2R)—N-(1-cyanocyclopropyl)-2-[(8-fluoro-5-methyl-1,3,4,5-tetrahydro-2H-pyrido[4,3-b]indol-2-yl)carbonyl]cyclohexanecarboxamide;
- (1R,2R)-2-[(6-bromo-1,3,4,5-tetrahydro-2H-pyrido[4,3-b]indol-2-yl)carbonyl]-N-(1-cyanocyclopropyl)cyclohexanecarboxamide;
- (1R,2R)—N-(1-Cyanocyclopropyl)-2-[1,3,4,5-tetrahydro-1H-pyrido[4,3-β]-7-azaindol-2-yl)carbonyl]cyclohexanecarboxamide
- (1R,2R)—N-(1-cyanocyclopropyl)-2-({8-[(dimethylamino)methyl]-1,3,4,5-tetrahydro-2H-pyrido[4,3-b]indol-2-yl]carbonyl}cyclohexanecarboxamide;
- (1R,2R)—N-(1-cyanocyclopropyl)-2-[8-(methylsulfonyl)-1,3,4,5-tetrahydro-2H-pyrido[4,3-b]indol-2-yl]carbonyl}cyclohexanecarboxamide;
- (1R,2R)—N-(1-cyanocyclopropyl)-2-[(6-methoxy-1,3,4,5-tetrahydro-2H-pyrido[4,3-b]indol-2-yl)carbonyl]cyclohexanecarboxamide;
- (1R,2R)—N-(1-cyanocyclopropyl)-2-(1H-spiro[isoquinoline-4,4'-piperidin]-2(3H)-ylcarbonyl)cyclohexanecarboxamide;
- (1R,2R)-2-[(6-chloro-1,3,4,5-tetrahydro-2H-pyrido[4,3-b]indol-2-yl)carbonyl]-N-(1-cyanocyclopropyl)cyclohexanecarboxamide;

(1R,2R)—N-(1-cyanocyclopropyl)-2-[(6-cyano-1,3,4,5-tetrahydro-2H-pyrido[4,3-b]indol-2-yl)carbonyl]cyclohexanecarboxamide;

(1R,2R)—N-(1-cyanocyclopropyl)-2-[(9-methyl-5,7,8,9-tetrahydro-6H-pyrrolo[2,3-b:4,5-c']dipyridin-6-yl)carbonyl]cyclohexanecarboxamide;

(1R,2R)—N-(1-cyanocyclopropyl)-2-{[6-(methylthio)-1,3,4,5-tetrahydro-2H-pyrido[4,3-b]indol-2-yl]carbonyl}cyclohexanecarboxamide;

(1R,2R)—N-(1-cyanocyclopropyl)-2-[(benzofuro[3,2-c]-1,2,3,4-tetrahydropyridyl)carbonyl]cyclohexanecarboxamide;

(1R,2R)—N-(1-cyanocyclopropyl)-2-{[6-(trifluoromethoxy)-1,3,4,5-tetrahydro-2H-pyrido[4,3-b]indol-2-yl]carbonyl}cyclohexanecarboxamide;

(1R,2R)—N-(1-cyanocyclopropyl)-2-[(6-ethoxy-1,3,4,5-tetrahydro-2H-pyrido[4,3-b]indol-2-yl)carbonyl]cyclohexanecarboxamide;

(1R,2R)—N-(1-cyanocyclopropyl)-2-[(5-cyclopropylmethyl-1,3,4,5-tetrahydro-2H-pyrido[4,3-b]indol-2-yl)carbonyl]cyclohexanecarboxamide;

(1R,2R)—N-(1-cyanocyclopropyl)-2-[(5-methoxyethyl-1,3,4,5-tetrahydro-2H-pyrido[4,3-b]indol-2-yl)carbonyl]cyclohexanecarboxamide;

(1R,2R)—N-(1-cyanocyclopropyl)-2-{[6-(trifluoromethyl)-1,3,4,5-tetrahydro-2H-pyrido[4,3-b]indol-2-yl]carbonyl}cyclohexanecarboxamide;

(1R,2R)—N-(1-cyanocyclopropyl)-2-{[6-(methylsulfonyl)-1,3,4,5-tetrahydro-2H-pyrido[4,3-b]indol-2-yl]carbonyl}cyclohexanecarboxamide;

(1R,2R)-2-{[6-(benzyloxy)-1,3,4,5-tetrahydro-2H-pyrido[4,3-b]indol-2-yl]carbonyl}-N-(1-cyanocyclopropyl)cyclohexanecarboxamide;

(1R,2R)—N-(1-cyanocyclopropyl)-2-[(6-hydroxy-1,3,4,5-tetrahydro-2H-pyrido[4,3-b]indol-2-yl)carbonyl]cyclohexanecarboxamide;

(1R,2R)—N-(1-cyanocyclopropyl)-2-[(6-propoxy-1,3,4,5-tetrahydro-2H-pyrido[4,3-b]indol-2-yl)carbonyl]cyclohexanecarboxamide;

(1R,2R)—N-(1-cyanocyclopropyl)-2-{[6-(cyanomethoxy)-1,3,4,5-tetrahydro-2H-pyrido[4,3-b]indol-2-yl]carbonyl}cyclohexanecarboxamide;

(1R,2R)—N-(1-cyanocyclopropyl)-2-(6-(2-(dimethylamino)ethoxy)-2,3,4,5-tetrahydro-1H-pyrido[4,3-b]indole-2-carbonyl)cyclohexanecarboxamide;

(1R,2R)—N-(1-cyanocyclopropyl)-2-(6-(2-morpholinoethoxy)-2,3,4,5-tetrahydro-1H-pyrido[4,3-b]indole-2-carbonyl)cyclohexanecarboxamide;

(1R,2R)—N-(1-cyanocyclopropyl)-2-(6-(2-(pyrrolidin-1-yl)ethoxy)-2,3,4,5-tetrahydro-1H-pyrido[4,3-b]indole-2-carbonyl)cyclohexanecarboxamide;

(1R,2R)—N-(1-cyanocyclopropyl)-2-(6-(2-(piperidin-1-yl)ethoxy)-2,3,4,5-tetrahydro-1H-pyrido[4,3-b]indole-2-carbonyl)cyclohexanecarboxamide;

(1R,2R)—N-(1-cyanocyclopropyl)-2-[(5-methanesulphonyl-1,3,4,5-tetrahydro-2H-pyrido[4,3-b]indol-2-yl)carbonyl]cyclohexanecarboxamide;

(1R,2R)-2-(7,8-Dihydro-5H-furo[2,3-b:4,5-c']dipyridine-6-carbonyl)-cyclohexanecarboxylic acid (1-cyano-cyclopropyl)-amide;

(1R,2R)-2-(7-Methanesulfonyl-1,3,4,5-tetrahydro-pyrido[4,3-b]indole-2-carbonyl)-cyclohexanecarboxylic acid (1-cyano-cyclopropyl)-amide;

(1R,2R)-2-(9-Methanesulfonyl-1,3,4,5-tetrahydro-pyrido[4,3-b]indole-2-carbonyl)-cyclohexanecarboxylic acid (1-cyano-cyclopropyl)-amide;

(1R,2R)—N-(1-cyanocyclopropyl)-2-(2,2-difluoro-7,8,9,10-tetrahydro-6H-[1,3]dioxolo[4,5-g]pyrido[4,3-b]indole-7-carbonyl)cyclohexanecarboxamide; and (1R,2R)—N-(1-cyanocyclopropyl)-2-(8-fluoro-6-methoxy-2,3,4,5-tetrahydro-1H-pyrido[4,3-b]indole-2-carbonyl)cyclohexanecarboxamide;

or a pharmaceutically acceptable salt thereof.

5. The compound or salt according to claim 3, wherein $R^1$ and $R^2$ together with the nitrogen atom to which they are attached form any one of a 1,3,4,5-tetrahydro-2H-pyrido[4,3-b]indolyl, 5,7,8,9-tetrahydro-6H-pyrrolo[2,3-b:4,5-c']dipyridinyl ring, 2,3,4,5-tetrahydro-1H-pyrido[4,3-b]-7-azaindolyl, benzofuro[3,2-c]-1,2,3,4-tetrahydropyridyl and 5,6,7,8-tetrahydrofuro[2,3-b:4,5-c']dipyridine.

6. The compound or salt according to claim 4, being (1R,2R)—N-(1-cyanocyclopropyl)-2-[(6-methoxy-1,3,4,5-tetrahydro-2H-pyrido[4,3-b]indol-2-yl)carbonyl]cyclohexanecarboxamide.

7. A pharmaceutical composition which comprises a compound of the formula (I) or a pharmaceutically acceptable salt thereof, as claimed in any one of claims 1, 2, 3, 4, 5, or 6, and a pharmaceutically acceptable diluent or carrier.

8. A process for the preparation of a compound of formula (I) as defined in claim 1 which comprises:

(a) treating a compound of formula (II):

$$\text{(II)}$$

with a compound of formula (III):

$$\text{(III)}$$

wherein A, R, $R^1$ and $R^2$ are as defined in claim 1, or (b) treating a compound of formula (IV):

$$\text{(IV)}$$

with a compound of formula (V):

$$\text{(V)}$$

wherein A, R, $R^1$ and $R^2$ are as defined in claim 1, and optionally after (a) or (b) forming a pharmaceutically acceptable salt.

9. A method for treating osteoporosis or metastatic bone disease in a mammal in need of such treatment, which comprises administering to said mammal an effective amount of a compound, or a pharmaceutically acceptable salt thereof, as claimed in any one of claim 2, 3, 4, 5, or 6.

* * * * *

UNITED STATES PATENT AND TRADEMARK OFFICE
CERTIFICATE OF CORRECTION

| | | |
|---|---|---|
| PATENT NO. | : 8,008,279 B2 | Page 1 of 1 |
| APPLICATION NO. | : 12/145855 | |
| DATED | : August 30, 2011 | |
| INVENTOR(S) | : Alexander Dossetter and Nicola Murdoch Heron | |

It is certified that error appears in the above-identified patent and that said Letters Patent is hereby corrected as shown below:

ON THE TITLE PAGE:

Item (56) References Cited, under Foreign Patent Documents:
insert -- WO2005/000800 01/06/2005 --.

IN THE CLAIMS:

Column 67, claim 1, line 36 (Approx.), "$C_{3-7}$-carbocyclyl" should read -- $C_{3-7}$carbocyclyl --;

Column 68, claim 4, line 31, "2-[8" should read -- 2-{[8 --;

Column 68, claim 4, lines 52-53 (Approx.), "cyclohexanecarboxamide" should read
-- cyclohexanecarboxamide; --;

Column 68, claim 4, line 56 (Approx.), "indol-2-yl]carbonyl}" should read
-- indol-2-yl}carbonyl) --;

Column 68, claim 4, line 57, "2-[8" should read -- 2-{[8 --;

Column 70 claim 9, line 62 (Approx.), "claim 2, 3, 4, 5, 6" should read -- claims 1, 2, 3, 4, 5, 6 --.

Signed and Sealed this
Seventh Day of August, 2012

David J. Kappos
*Director of the United States Patent and Trademark Office*